(12) United States Patent
Ismagilov et al.

(10) Patent No.: US 10,866,184 B2
(45) Date of Patent: Dec. 15, 2020

(54) DEVICES AND METHODS FOR DIRECT VISUAL DETECTION AND READOUT OF SINGLE NUCLEIC ACID MOLECULES

(71) Applicant: CALIFORNIA INSTITUTE OF TECHNOLOGY, Pasadena, CA (US)

(72) Inventors: Rustem F. Ismagilov, Altadena, CA (US); Jesus Rodriguez Manzano, London (GB); Mikhail Karymov, San Jose (CA); David A. Selck, Sterling, VA (US); Stefano Begolo, Inglewood, CA (US); Erik B. Jue, Moorpark, CA (US); Dmitriy V. Zhukov, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 43 days.

(21) Appl. No.: 15/774,004

(22) PCT Filed: Nov. 4, 2016

(86) PCT No.: PCT/US2016/060726
§ 371 (c)(1),
(2) Date: May 5, 2018

(87) PCT Pub. No.: WO2017/079696
PCT Pub. Date: May 11, 2017

(65) Prior Publication Data
US 2018/0321137 A1  Nov. 8, 2018

Related U.S. Application Data

(60) Provisional application No. 62/252,167, filed on Nov. 6, 2015, provisional application No. 62/297,041, filed on Feb. 18, 2016.

(51) Int. Cl.
*G01N 21/25* (2006.01)
*G06K 9/00* (2006.01)
(Continued)

(52) U.S. Cl.
CPC ......... *G01N 21/253* (2013.01); *C12Q 1/6844* (2013.01); *G01J 3/0272* (2013.01);
(Continued)

(58) Field of Classification Search
CPC .......... G01N 21/253; G01N 2201/0221; G01J 3/463; G01J 3/46; G01J 3/50;
(Continued)

(56) References Cited

U.S. PATENT DOCUMENTS

2002/0122590 A1* 9/2002 Kaneda ................ G06K 9/6857
382/181
2005/0042707 A1  2/2005 Brocia
(Continued)

OTHER PUBLICATIONS

PCT International Search Report & Written Opinion, International Application No. PCT/US2016/060726, dated Jan. 31, 2017, 16 Pages.

*Primary Examiner* — Amandeep Saini
(74) *Attorney, Agent, or Firm* — Goodwin Procter LLP

(57) ABSTRACT

The present invention relates to methods, computer readable medium and systems for detecting and counting single nucleic acid molecules confined in nanoliter volumes using an unmodified camera, such as a cell phone camera. In particular, it identifies colorimetric amplification-indicator dyes that are compatible with the spectral sensitivity of standard mobile phones. The invention further provides an optimal ratiometric image-process for a selected dye to achieve a readout that is robust to lighting conditions and
(Continued)

Figure 1:
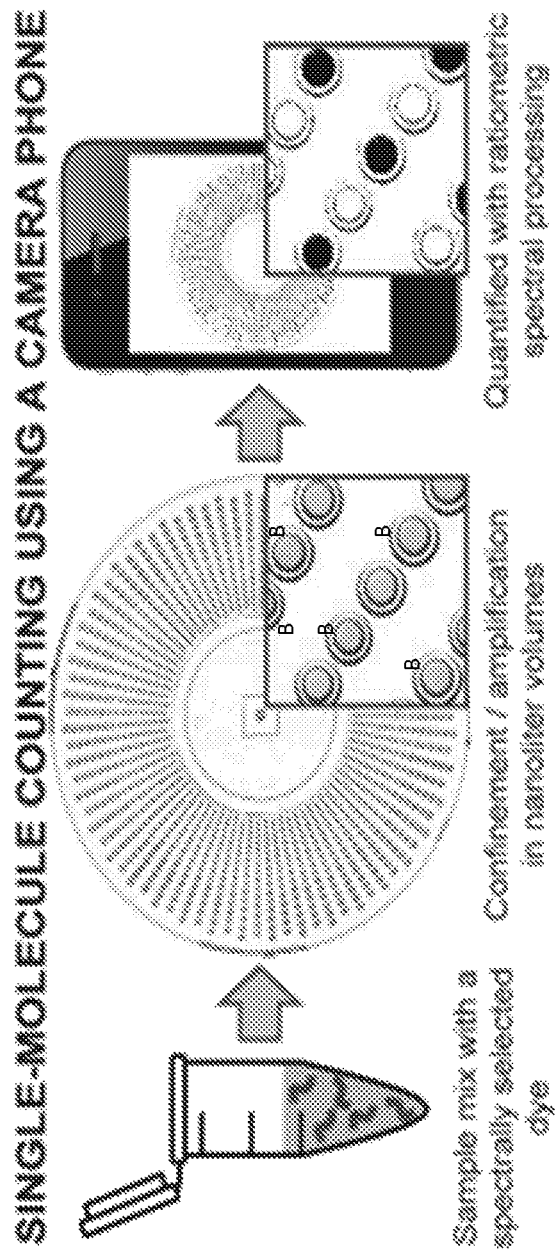

camera hardware and provides unambiguous quantitative results, even for colorblind users.

28 Claims, 32 Drawing Sheets

Specification includes a Sequence Listing.

(51) Int. Cl.
  *G01J 3/46* (2006.01)
  *G06T 7/90* (2017.01)
  *C12Q 1/6844* (2018.01)
  *G01J 3/02* (2006.01)
  *G01J 3/50* (2006.01)

(52) U.S. Cl.
  CPC .............. *G01J 3/46* (2013.01); *G01J 3/463* (2013.01); *G01J 3/50* (2013.01); *G06K 9/00134* (2013.01); *G06T 7/90* (2017.01); *G01J 2003/468* (2013.01); *G01N 2201/0221* (2013.01); *G06T 2207/10012* (2013.01); *G06T 2207/10024* (2013.01); *G06T 2207/10056* (2013.01); *G06T 2207/10064* (2013.01); *G06T 2207/30024* (2013.01)

(58) Field of Classification Search
  CPC ............. G01J 3/0272; G01J 2003/468; C12Q 1/6844; G06T 7/90; G06T 2207/10056; G06T 2207/10012; G06T 2207/10064; G06T 2207/30024; G06T 2207/10024; G06K 9/00134
  USPC ......................................................... 382/133
  See application file for complete search history.

(56) References Cited

U.S. PATENT DOCUMENTS

| | | | |
|---|---|---|---|
| 2010/0220223 A1* | 9/2010 | Tsuruoka | ................ G06T 5/002 348/242 |
| 2012/0197610 A1 | 8/2012 | Kahlman et al. | |
| 2014/0107980 A1 | 4/2014 | Yamashita et al. | |
| 2015/0247190 A1* | 9/2015 | Ismagilov | ........... C12Q 1/6851 506/9 |

* cited by examiner

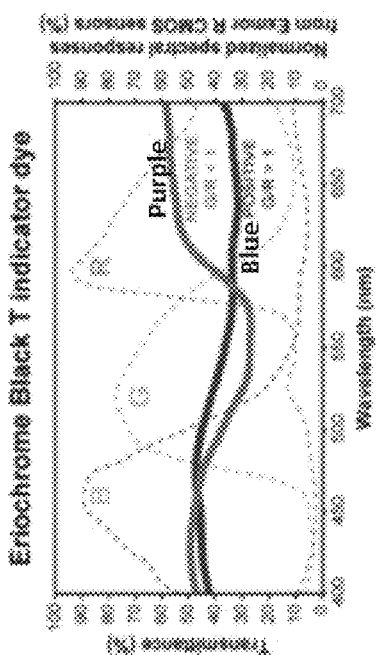
FIG.4A
FIG.4B
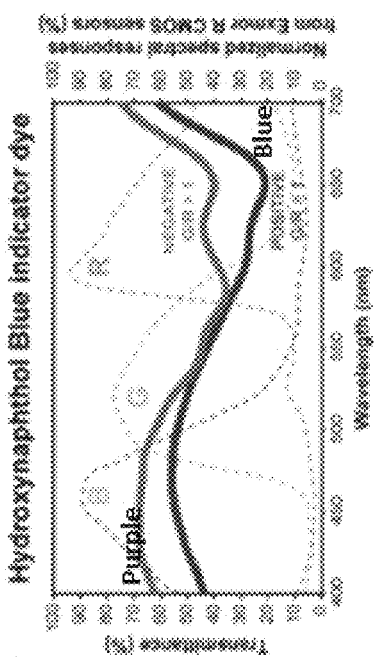
FIG.4C
FIG.4D
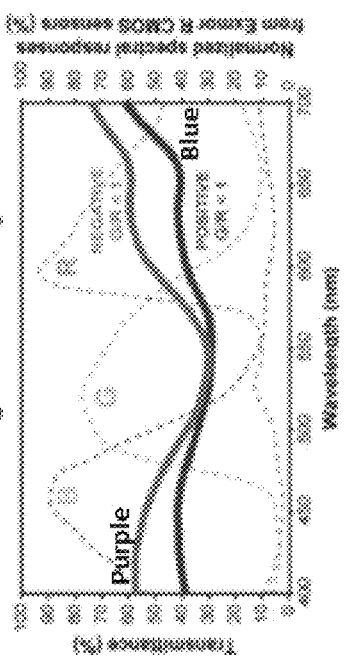
FIG.4E
FIG.4F

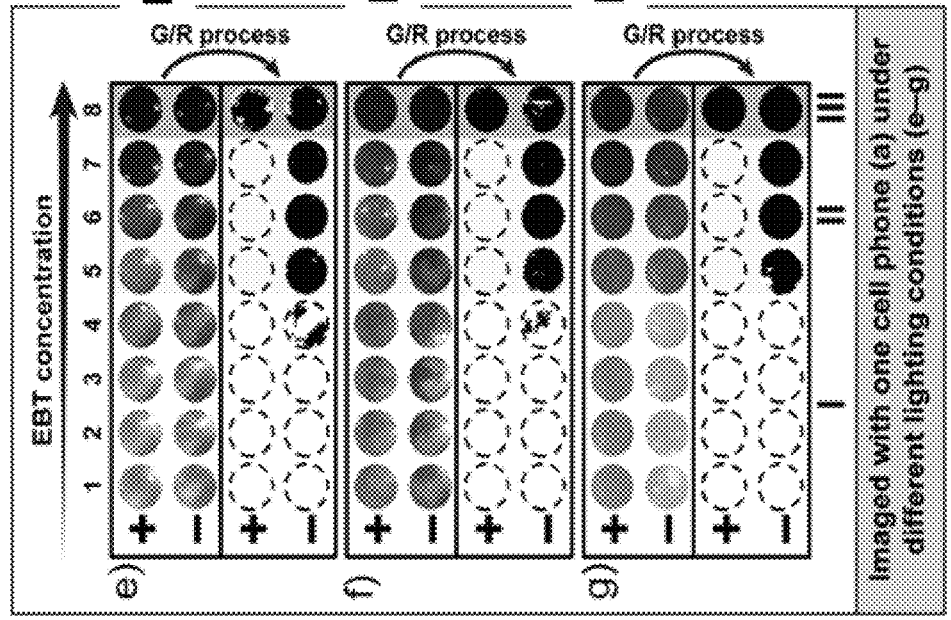
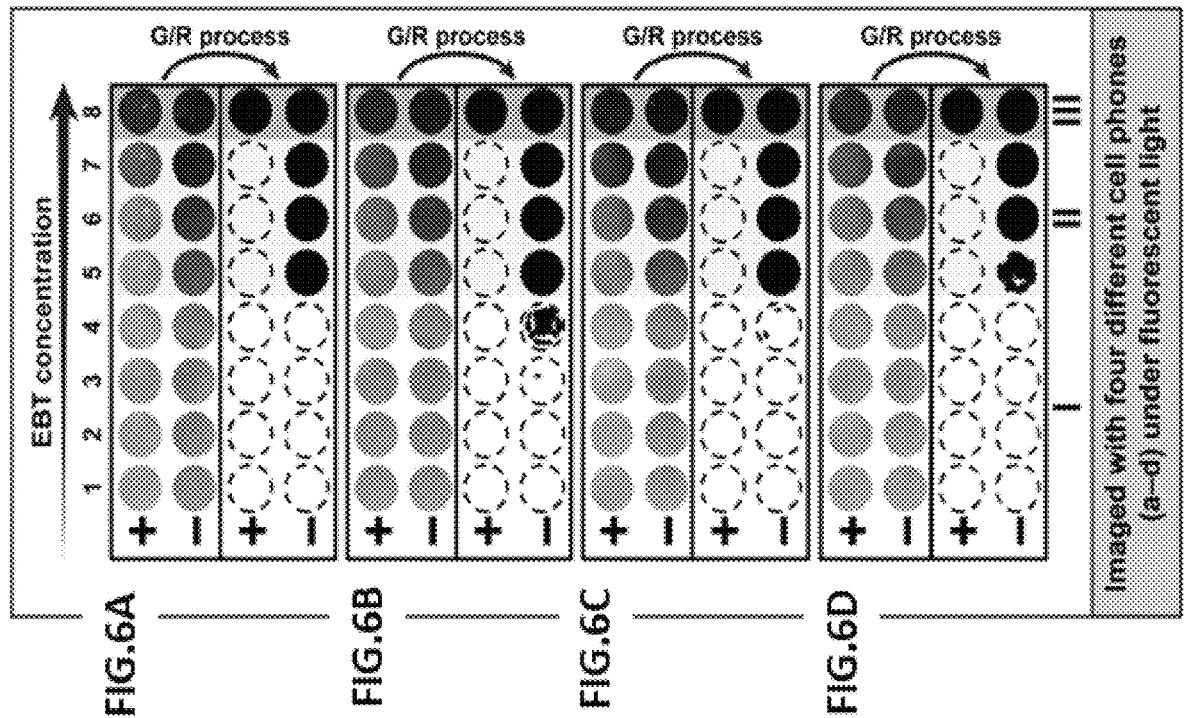

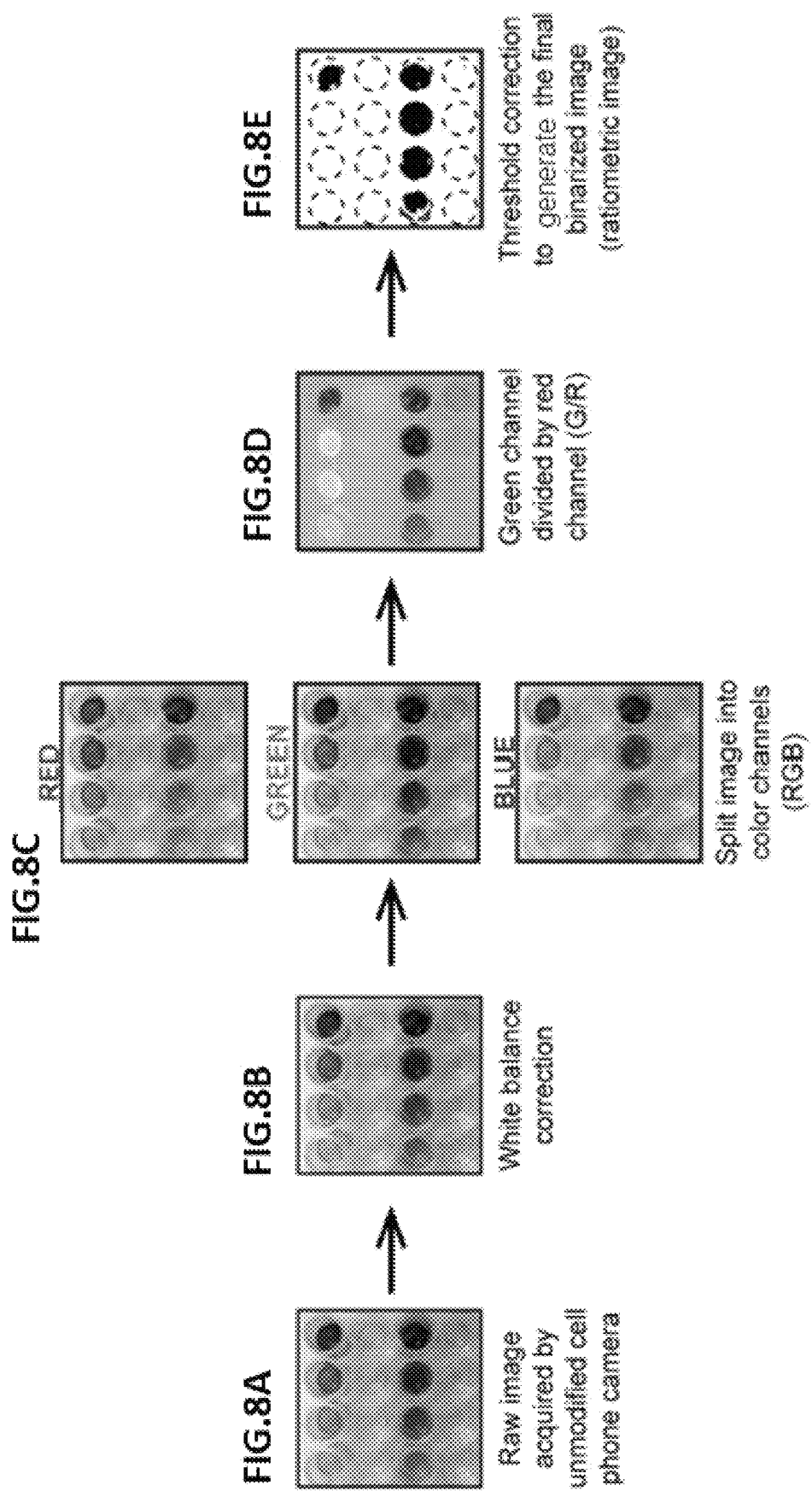

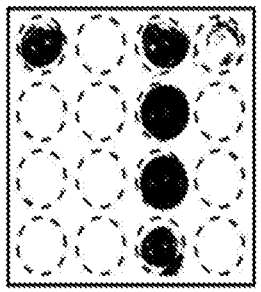
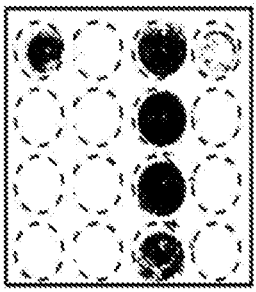
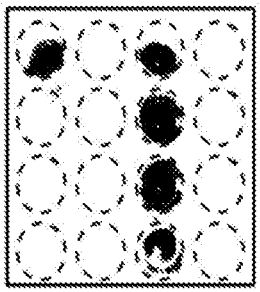
FIG.9E  FIG.9F  FIG.9G
5)  6)  7)
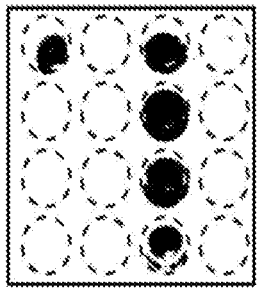
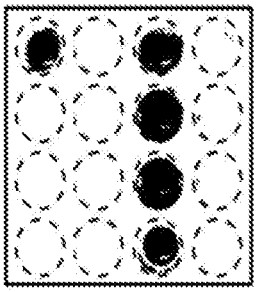
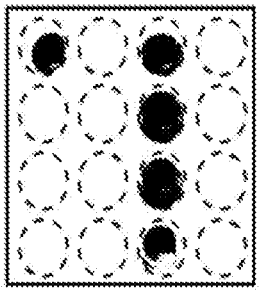
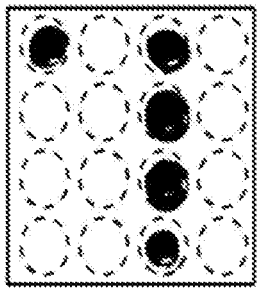
FIG.9A  FIG.9B  FIG.9C  FIG.9D

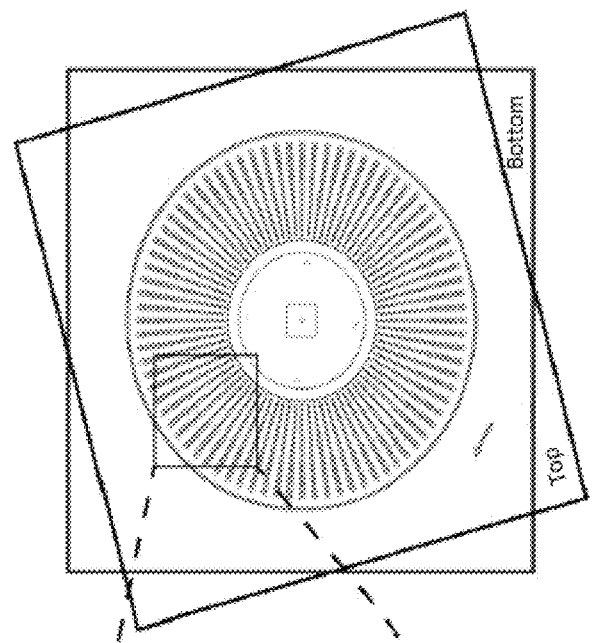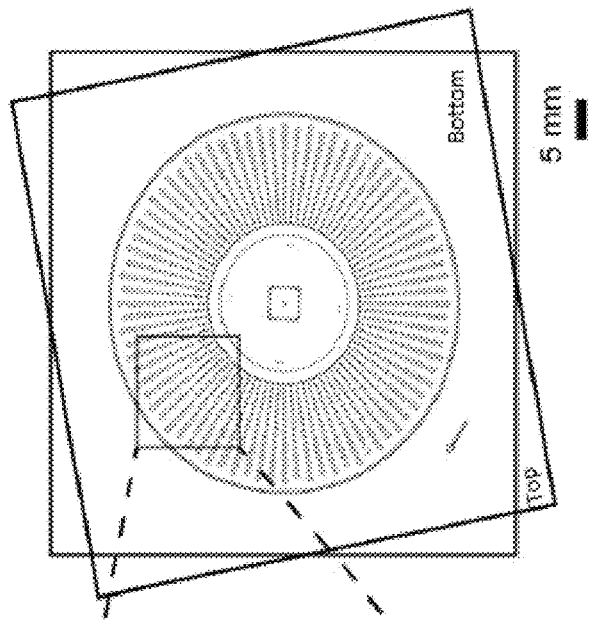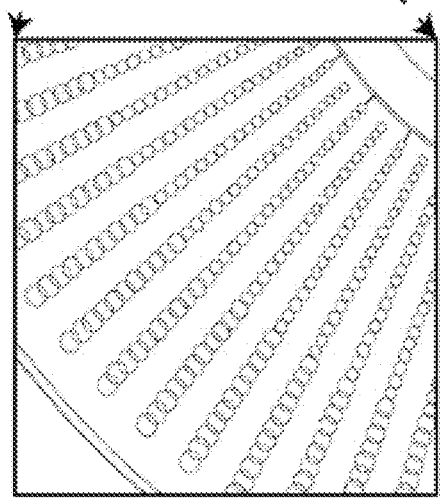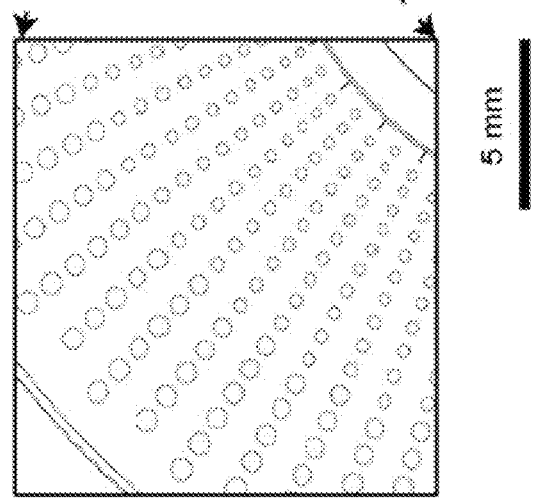
FIG.11A
FIG.11B

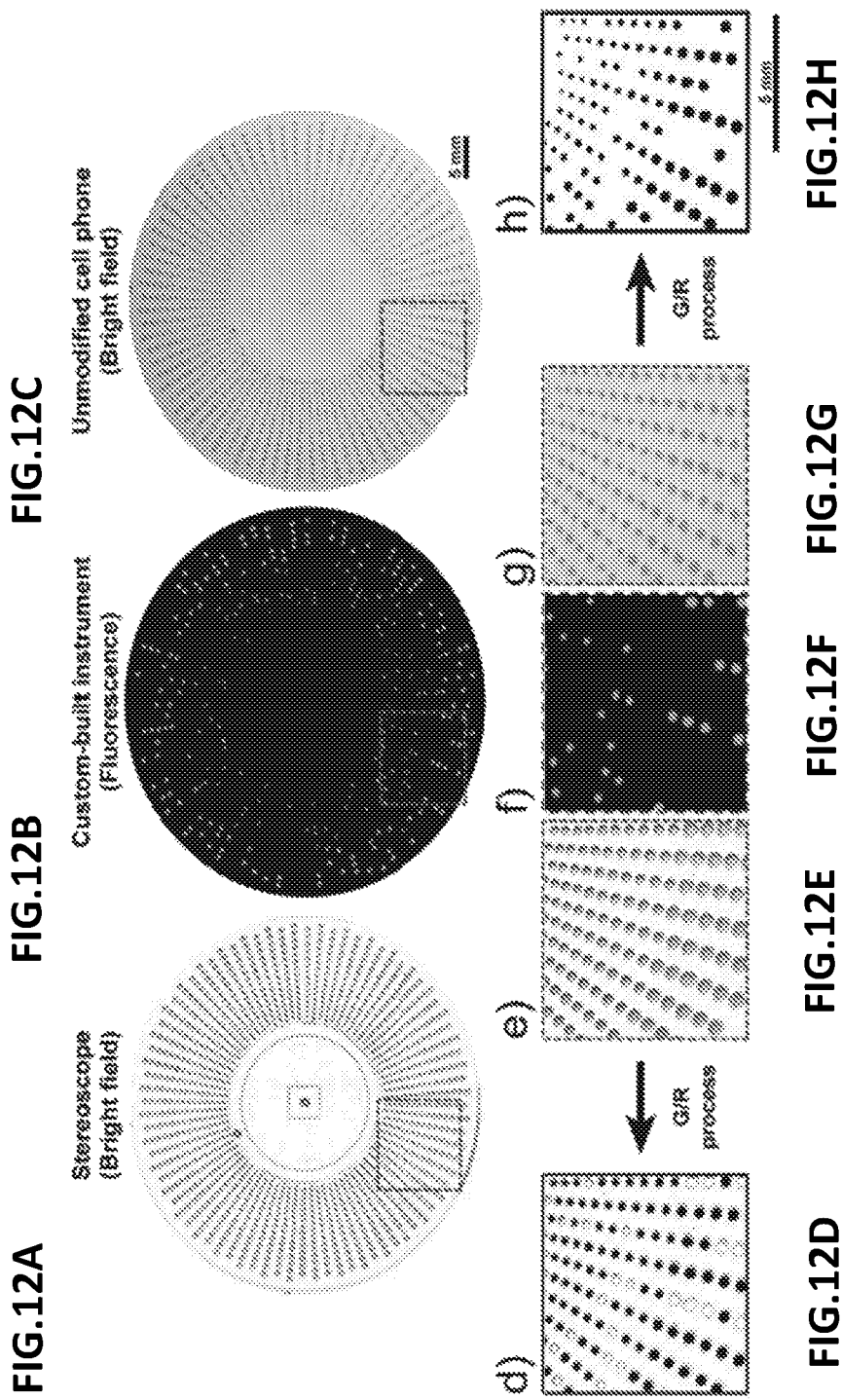

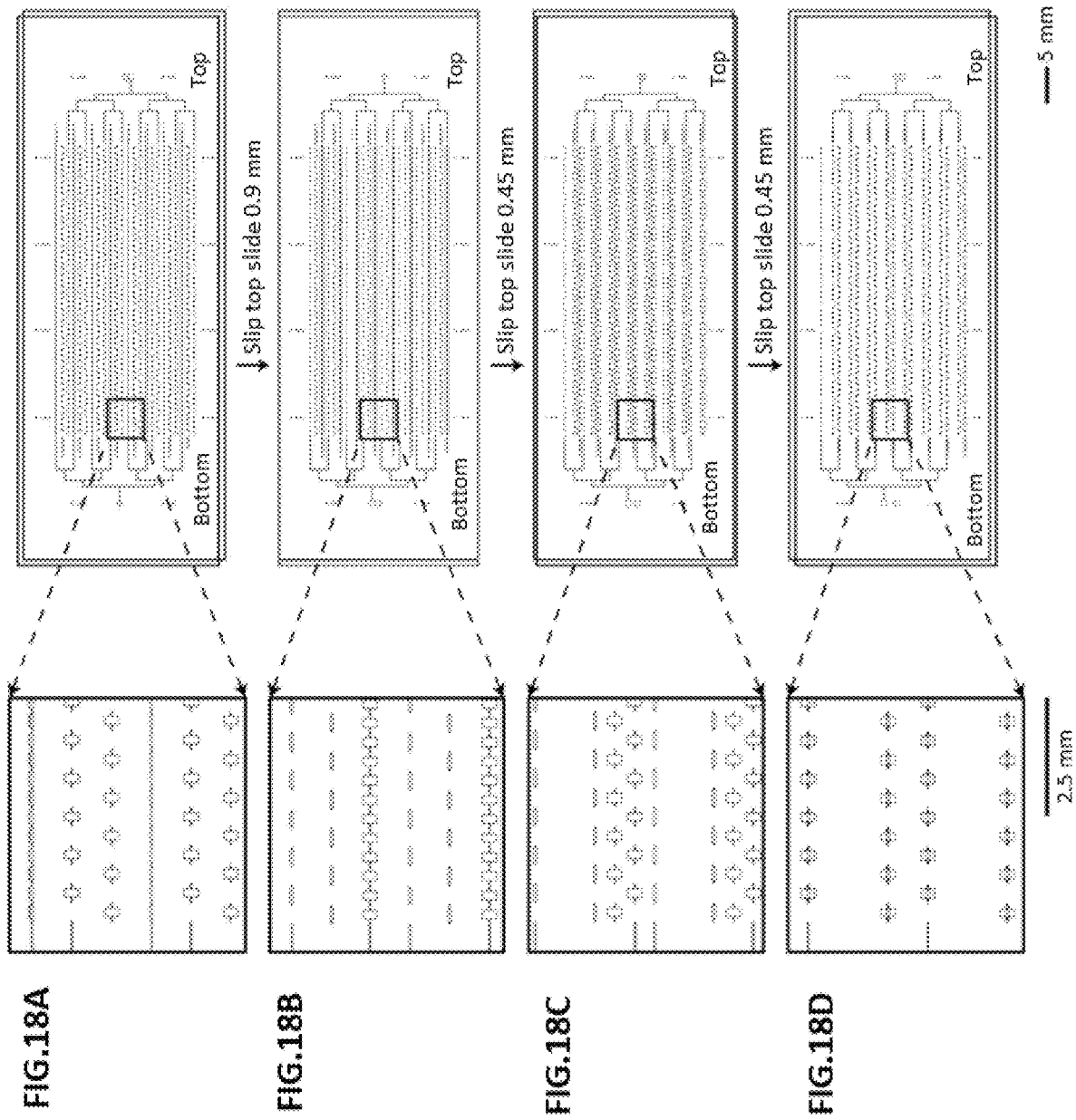

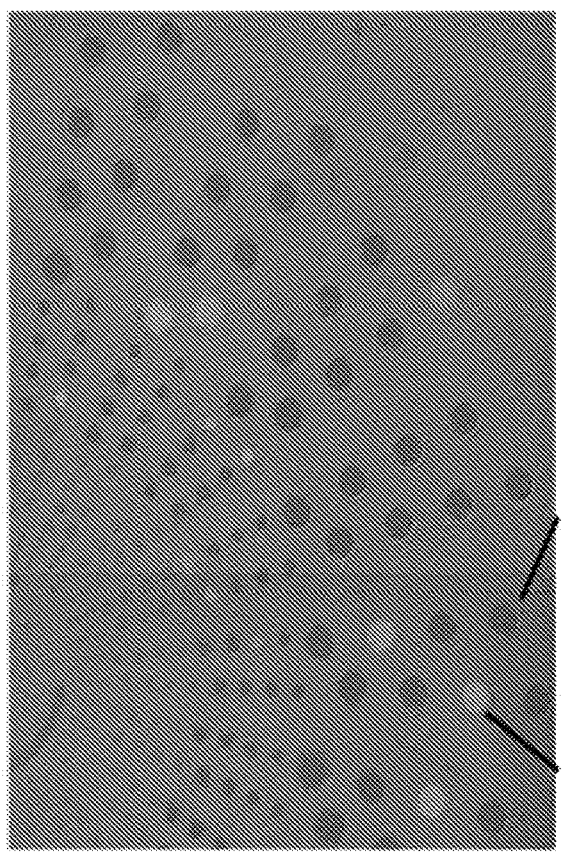
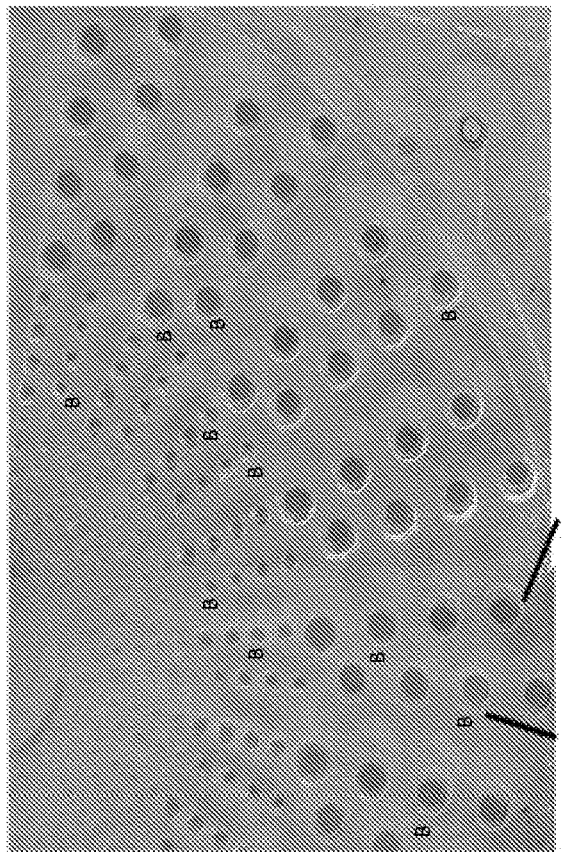
FIG.25 a) Raw image from unmodified cell phone camera b) Green channel divided by Red channel (G/R)

c) Threshold adjustment

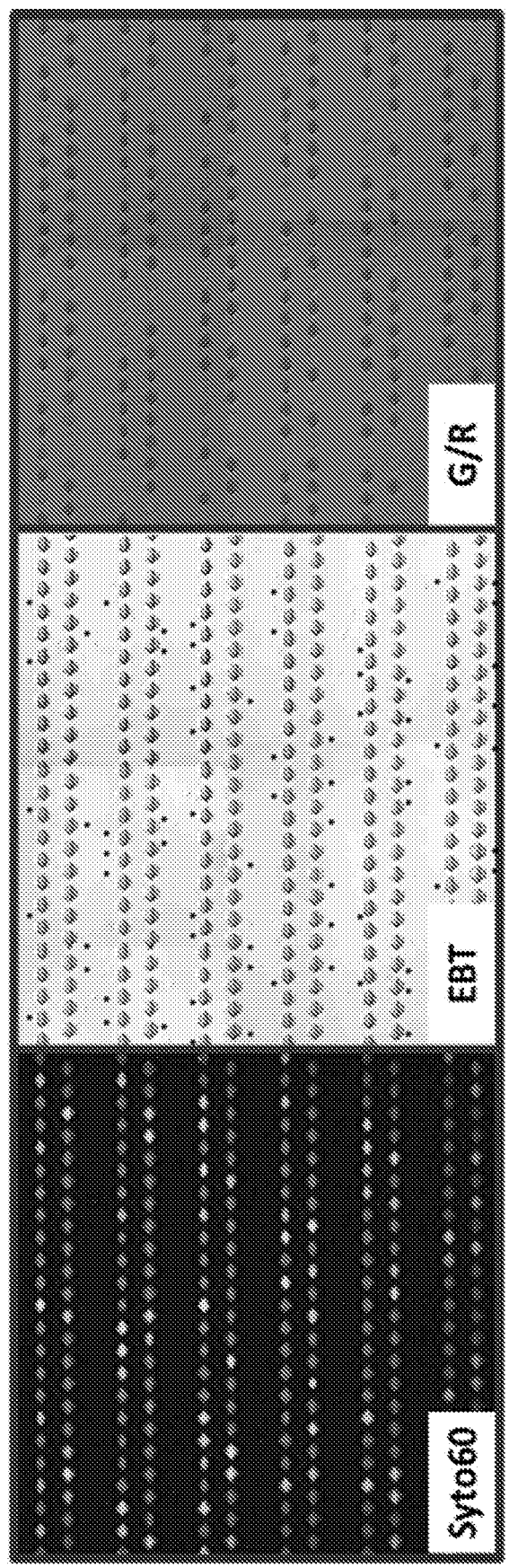
FIG. 27A  Syto60
FIG. 27B  EBT
FIG. 27C  G/R

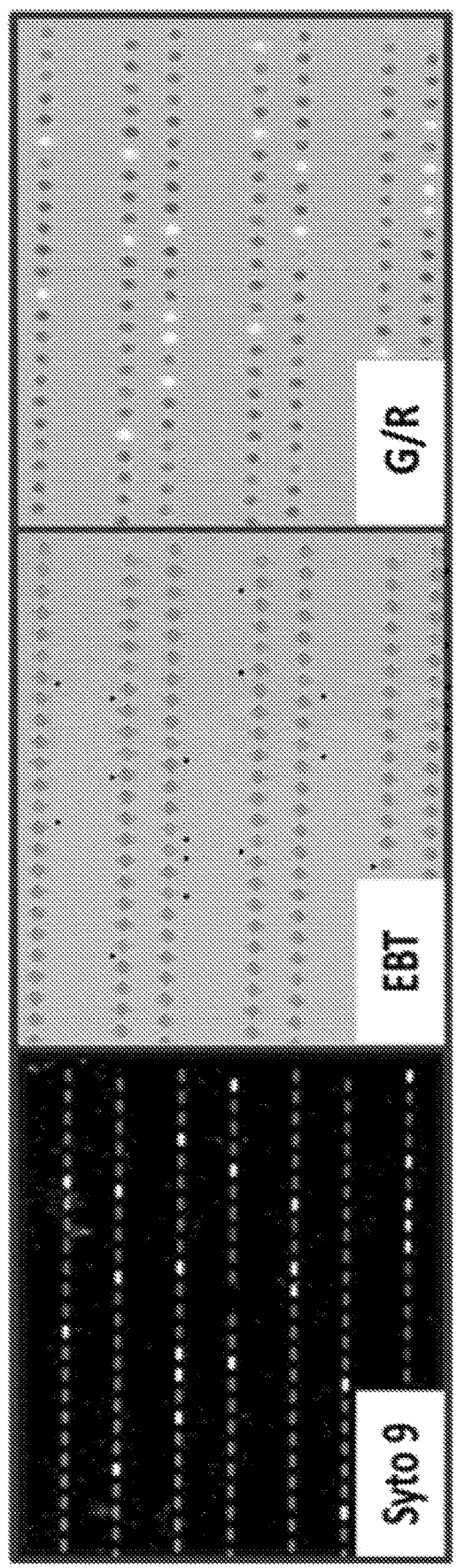

DEVICES AND METHODS FOR DIRECT VISUAL DETECTION AND READOUT OF SINGLE NUCLEIC ACID MOLECULES

1. CROSS-REFERENCE

This application is the National Stage of International Application No. PCT/US2016/060726, filed Nov. 4, 2016, which claims the benefit of U.S. Provisional Application Nos. 62/252,167 filed Nov. 6, 2015, and 62/297,041 filed on Feb. 18, 2016, which applications are incorporated herein by reference in their entirety.

2. STATEMENT AS TO FEDERALLY SPONSORED RESEARCH

This invention was made with government support under Grant No. HR0011-11-2-0006 awarded by DARPA, under Grant No. EB012946 awarded by the National Institutes of Health, and under Grant No. DGE1144469 awarded by the National Science Foundation. The government has certain rights in the invention.

2.1 Sequence Listing

The instant application contains a Sequence Listing which has been submitted electronically in ASCII format and is hereby incorporated by reference in its entirety. Said ASCII copy, created on Oct. 30, 2020, is named TCT-029_SL.txt and is 3,632 bytes in size.

3. BACKGROUND

Ultrasensitive and quantitative detection of nucleic acid molecules is of particular interest for infectious disease diagnosis in limited resource settings (LRS), such as the quantification of viral load for human immunodeficiency virus (HIV) and hepatitis C virus (HCV), as many of these infections occur far from centralized laboratories where diagnostic tests are routine. Increasing diagnoses in these locations will lead to faster and more appropriate treatment and have a major impact on disease burden. Most point of care (POC) tests are not amenable to LRS because they don't meet the World Health Organization's ASSURED criteria of being affordable, sensitive, specific, user-friendly, rapid, robust, equipment-free and deliverable.

The tests that do meet the requirements for LRS (e.g., immunochromatography to detect antigens or antibodies in a dipstick or lateral-flow format; or the visualization of antigen-antibody lattice formation) have poor reported sensitivities and thus are unable to detect and quantify analytes at low concentrations. Nucleic acid amplification tests (NAATs), such as PCR, have the desired high sensitivity and target specificity, providing accurate quantification, but these technologies are costly, time-consuming, and require skilled technicians and laboratory settings.

Of the NAATs, isothermal amplification methods (e.g., loop-mediated isothermal amplification, LAMP) are among the most attractive for LRS because they do not require thermocycling or capital equipment and can be run in water baths, using simple heaters or with exothermic chemical heating that does not require electricity. Still, acquiring quantitative and ultrasensitive measurements outside of the lab remains challenging because the methods are not robust to variability in reaction conditions and readouts rely on precise measures of fluorescence intensity. Running isothermal amplification chemistries in a digital, single-molecule format maintains the high sensitivity and quantification capabilities typically achieved only in lab settings. In digital single-molecule isothermal amplification, single, stochastically confined DNA or RNA molecules are randomly distributed among discrete nanoliter or picoliter volumes and amplified under controlled conditions. This creates relatively high local concentrations of target DNA or RNA, making digital amplification more efficient and robust compared to bulk reactions with the same number of starting target molecules. Nucleic acid amplification of even a single target molecule produces a clear fluorescent signal and the results of digital amplification can be read by a modified cell phone (e.g., a phone camera with an optical filter) under dim lighting.

Microfluidic technology has been an instrumental tool in developing single nucleic acid molecule capabilities, and the integration of sample-preparation modules into portable microfluidic devices has been expected to further enable their use by untrained users in any setting. To bring these emerging technological capabilities to LRS, however, such devices capable of ultrasensitive, quantitative measurements should provide a rapid, visual readout that can be captured easily—e.g., by any mobile phone without modifications or attachments. Cell phone cameras provide a convenient, nearly universal tool to pair with emerging diagnostic technologies to transform global healthcare as ~7 billion mobile cellular subscribers exist worldwide and 70% of users live in developing countries. Mobile devices are emerging as a powerful platform to create cost-effective alternatives for molecular diagnostics in LRS32-42 and colorimetric diagnostics based on unmodified cell phones have been used before, but not in a digital format, where the short path lengths and nanoliter volumes have constrained visual-based methods.

Thus, there has been a need for a system that enables visual readout of single nucleic acid molecule amplification using a simple device, such as an unmodified cell phone camera. Replacing fluorescent readout of existing digital single-molecule technologies with a robust visual readout that can be captured by any unmodified cell phone camera will facilitate the global distribution of diagnostic tests, including into limited-resource settings where the need is greatest.

4. SUMMARY

In one aspect, the invention provides a method of visually detecting a target nucleic acid in a sample, comprising steps of: dividing the sample into a plurality of compartments; performing an amplification reaction on the divided sample to generate a reaction product; exposing the reaction product to an amplification indicator; obtaining a color image of the reaction product in the plurality of compartments; determining a plurality of first intensities for a first color of the color image, wherein the plurality of first intensities corresponds to the plurality of compartments; determining a plurality of second intensities for a second color of the color image, wherein the plurality of second intensities corresponds to the plurality of compartments; and determining a ratio between the first color intensity and the second color intensity for a compartment. In the invention, the ratio is indicative of the presence or absence of amplified target in the compartment.

The present invention also relates to a method of visually detecting amplification of a target nucleic acid, comprising: performing an amplification reaction on a sample to generate a reaction product; exposing the reaction product to an amplification indicator; obtaining a color image of the reaction product; determining a first color intensity of the color image; determining a second color intensity of the color image; and determining a ratio between the first color intensity and the second color intensity, wherein the ratio is indicative of presence of absence of amplified target nucleic acid.

The present invention further provides a method of analyzing an color image of an amplification reaction product, comprising steps of: obtaining a color image of the amplification reaction product wherein the amplification reaction product is generated by performing an amplification reaction on a sample and exposing a mixture for the amplification reaction to an amplification indicator; determining a first color intensity of the color image; determining a second color intensity of the color image; determining a ratio between the first color intensity and the second color intensity, wherein the ratio is indicative of the presence or absence of an amplified target in the amplification reaction product.

In some embodiments, the method further comprises a step of applying a threshold to the ratio to generate a binary readout of positive and negative reactions. In some embodiments, the threshold changes depending on the amplification indicator.

In some embodiments, the step of exposing the reaction product to the amplification indicator is concurrent with the step of performing the amplification reaction. In some embodiments, the step of exposing the reaction product to the amplification indicator is subsequent to the step of performing the amplification reaction.

In some embodiments, the step of obtaining a color image comprises obtaining an unprocessed color image and updating the unprocessed color image to generate the color image.

In some embodiments, the color image or the unprocessed color image is obtained with an unmodified camera. In some embodiments, the unmodified camera is a cell phone camera. In some embodiments, the color image or the unprocessed color image is a bright field image.

In some embodiments, the color image is obtained by email, SMS messaging, web posting, phone call, electronic messaging, uploading or downloading.

In some embodiments, the color image is obtained by making the unprocessed color image suitable for a specific application. In some embodiments, the color image is obtained by enhancing a contrast of the unprocessed color image, by adjusting white balance of the unprocessed color image, or by correcting background signals. In some embodiments, the color image is obtained with software designed for image processing.

In some embodiments, the color image comprises images of a plurality of compartments. In some embodiments, the method further comprises a step of identifying one or more pixels corresponding to each of the plurality of compartments in the color image or the updated image. In some embodiments, the first color intensity and the second color intensity are an average of color intensities corresponding to a plurality of pixels within one of the plurality of compartments. In some embodiments, the step of determining the ratio between the first color intensity and the second color intensity is done for each of the plurality of compartments to generate a plurality of compartment color ratios, wherein each of the compartment color ratios correspond to each of the plurality of compartments. In some embodiments, the step of generating a binary readout is done for each of the plurality of compartments to generate a plurality of compartment binary readouts, wherein each of the compartment binary readouts correspond to each of the plurality of compartments.

In some embodiments, the method further comprises a step of determining a concentration of the target nucleic acid within the sample based on a distribution of the compartment binary readouts. In some embodiments, the binary readout indicates that there is no amplified target nucleic acid in a subset of the plurality of compartments. In some embodiments, the method further comprises a step of determining a presence or an absence of the target nucleic acid within the compartment based on the binary readout.

In some embodiments, the method further comprises a step of generating a binary image using the binary readout. In some embodiments, the method is further comprises a step of generating a binary image using the compartment binary readouts.

In some embodiments, the method further comprises a step of generating a report related to a composition of the sample. In some embodiments, the method further comprises a step of sending the report to a receiver by email, SMS messaging, web posting, phone call, electronic messaging, uploading or downloading. In some embodiments, the report is related to the binary readout, the binary image, the presence or absence of the target nucleic acid within the sample, or the concentration of the target nucleic acid within the sample.

In some embodiments, the target nucleic acid is an RNA molecule and the amplification reaction comprises reverse transcribing the RNA to a DNA. In some embodiments, the target nucleic acid is a DNA.

In some embodiments, the sample within each compartment has a volume ranging from 1 pL to 1 µL, 1 pL to 500 nL, 10 pL to 300 nL, 100 pL to 250 nL, 1 nL to 100 nL, 20 nL to 75 nL, or 30 nL to 50 nL. In some embodiments, each compartment has an optical path length less than 1 mm, ranging from 0.5 µm to 1 mm, 0.5 µm to 500 µm, 1 µm to 250 µm, 5 µm to 100 µm, 10 µm to 50 µm, or 25 µm to 50 µm.

In some embodiments, the step of determining the first color intensity and the second color intensity is done using a Red-Green-Blue (RGB) color scheme; cyan, magenta, yellow and key (black). (CYMK) color scheme; or L-A-B color scheme.

In some embodiments, the first color is red and the second color is green. In some embodiments, the first color is red and the second color is blue. In some embodiments, the first color is green and the second color is blue.

In some embodiments, the step of obtaining the color image of the reaction product comprises detecting light absorbance, light reflection, or light transmission of the reaction product at a plurality of different wavelengths. In some embodiments, the step of obtaining the color image of the reaction product comprises detecting light absorbance, light reflection, or light transmission of the reaction product at two different wavelengths. In some embodiments, the two different wave lengths are 540 nm and 650 nm.

In some embodiments, the amplification reaction is selected from the group consisting of polymerase chain reaction (PCR), reverse transcription PCR (RT-PCR), quantitative PCR (qPCR), reverse transcription qPCR (RT-qPCR), nested PCR, multiplex PCR, asymmetric PCR, touchdown PCR, random primer PCR, hemi-nested PCR, polymerase cycling assembly (PCA), colony PCR, ligase chain reaction (LCR), digital PCR, methylation specific-PCR (MSP), co-amplification at lower denaturation temperature-PCR (COLD-PCR), allele-specific PCR, intersequence-specific PCR (ISS-PCR), whole genome amplification (WGA), inverse PCR, thermal asymmetric interlaced PCR (TAIL-PCR).

In some embodiments, the amplification reaction is selected from the group consisting of Strand Displacement Amplification (SDA), Transcription Mediated Amplification (TMA), Nucleic Acid Sequence Based Amplification (NASBA), Recombinase Polymerase Amplification (RPA), Rolling Circle Amplification (RCA), Ramification Amplification (RAM), Helicase-Dependent Isothermal DNA Amplification (HDA), Circular Helicase-Dependent Amplification (cHDA), Loop-Mediated Isothermal Amplification (LAMP), Single Primer Isothermal Amplification (SPIA), Signal Mediated Amplification of RNA Technology (SMART), Self-Sustained Sequence Replication (3 SR), Genome Exponential Amplification Reaction (GEAR) and Isothermal Multiple Displacement Amplification (IMDA). In some embodiments, the amplification reaction is Loop-Mediated Isothermal Amplification (LAMP).

In some embodiments, the step of an amplification reaction lasts less than: 600 minutes, 540 minutes, 480 minutes, 420 minutes, 360 minutes, 300 minutes, 240 minutes, 180 minutes, 120 minutes, 110 minutes, 100 minutes, 90 minutes, 80 minutes, 70 minutes, 60 minutes, 50 minutes, 40 minutes, 30 minutes, 20 minutes, 15 minutes, 10 minutes, 9 minutes, 8 minutes, 7 minutes, 6 minutes, 5 minutes, 4 minutes, 3 minutes, 2 minutes, or 1 minute.

In some embodiments, each of the plurality of compartments includes no or less than five molecules of the target nucleic acid. In some embodiments, each of the plurality of compartments includes no or one molecule of the target nucleic acid.

In some embodiments, the amplification indicator is not a fluorescent dye.

In some embodiments, the amplification indicator has an extinction coefficient larger than 5,000 L mol-1 cm-1. In some embodiments, the extinction coefficient larger than: 10,000 L mol-1 cm-1, 20,000 L mol-1 cm-1, 25,000 L mol-1 cm-1, 50,000 L mol-1 cm-1, 100,000 L mol-1 cm-1 or 1000,000 L mol-1 cm-1. In some embodiments, the amplification indicator changes light absorbance, light reflection, or light transmission responsive to nucleic acid amplification. In some embodiments, the amplification indicator changes its extinction coefficient more than 3%, more than 5%, more than 10%, more than 20%, more than 30%, or more than 40% responsive to nucleic acid amplification.

In some embodiments, the amplification indicator is a metal ion indicator. In some embodiments, the metal ion is Ca2+, Mg2+, or Zn2+. In some embodiments, the amplification indicator is selected from the group consisting of hydroxynaphthol blue, eriochrome black t, calmagite, curcumin, fast sulphon black, hematoxylin, murexide, xylenon orange, BAPTA, BAPTA AM, BTC, BTC AM, Calcein, Calcein AM, Calcein Blue, Calcium Green 1, Calcium Green 2, Calcium Green 5N, Coelenterazine, Coelenterazine cp, Coelenterazine f, Coelenterazine h, Coelenterazine hcp, Coelenterazine n, CoroNa Green, Corona Green AM, CoroNa Red, DAF FM, Fluo 3, Fluo 3 AM, PBFI AM, Phen Green SK, Quin 2, Quin 2 AM, RhodZin 3. In some embodiments, the amplification indicator is eriochrome black t. In some embodiments, the amplification indicator is hydroxynaphthol blue. In some embodiments, the amplification indicator is calmagite.

In some embodiments, the amplification indicator is a pH indicator. In some embodiments, the pH indicator is a chemical detector for hydronium ions (H3O+) or hydrogen ions (H+). In some embodiments, the pH indicator is selected from the group consisting of gentian violet, malachite green, thymol blue, methyl yellow, bromophenol blue, congo red, methyl orange, screened methyl orange (first transition), screened methyl orange (second transition), Bromocresol green, methyl red, methyl Purple, azolitmin red, bromocresol purple, bromothymol blue, phenol red, neutral red, naphtholphthalein, Cresol red, Cresolphthalein, Phenolphthalein, Thymolphthalein, Alizarine Yellow R yellow, Indigo carmine.

In some embodiments, the amplification indicator is a redox indicator or an oxidation-reduction indicator. In some embodiments, the redox indicator or oxidation-reduction indicator is pH independent. In some embodiments, the redox indicator or oxidation-reduction indicator is selected from the group consisting of 2,2'-bipyridine, Nitrophenanthroline, N-Phenylanthranilic acid, 1,10-Phenanthroline iron(II) sulfate complex, N-Ethoxychrysoidine, 2,2'-Bipyridine, 5,6-Dimethylphenanthroline, o-Dianisidine, Sodium diphenylamine sulfonate, Diphenylbenzidine, Diphenylamine, Viologen.

In some embodiments, the redox indicator or oxidation-reduction indicator is pH dependent. In some embodiments, the redox indicator or oxidation-reduction indicator is selected from the group consisting of Sodium 2,6-Dibromophenol-indophenol, Sodium o-Cresol indophenol, Thionine, Methylene blue, Indigotetrasulfonic acid, Indigotrisulfonic acid, Indigo carmine, Indigomono sulfonic acid, Phenosafranin, Safranin, Neutral red.

In some embodiments, amplification reaction is done in a housing selected from the group consisting of a tube, a capillary tube, a droplet, a microfluidic device, a well, a well plate, a microplate, a microfluidic well, a microfluidic droplet, an emulsion, a solid support, a microchip, or a gel. In some embodiments, the housing is a solid support, wherein the solid support is a bead or a microarray. In some embodiments, the housing is a gel, wherein the gel is 2D or 3D.

In some embodiments, the housing is a microfluidic device. In some embodiments, the microfluidic device is a SlipChip device. In some embodiments, the microfluidic device comprises a plurality of compartments, each having a volume ranging from 500 nL to 1 µL, 250 nL to 500 nL, 125 nL to 250 nL, 25 nL to 125 nL, 5 nL to 25 nL, 1 nL to 5 nL, or 0.1 nL to 1 nL. In some embodiments, the compartments are wells, droplets, beads, or microarray spots. In some embodiments, the microfluidic device comprises a channel for loading fluids into a compartment, for mixing a content of a compartment, or for off-loading of a content of a compartment.

In some embodiments, the microfluidic device comprises a first layer and a second layer configured to move relative to each other between a first position and a second position. In some embodiments, the microfluidic device comprises a plurality of reaction compartments; and a plurality of indicator compartments, wherein the plurality of reaction compartments and indicator compartments are isolated from each other in said first position, and wherein at least some of the plurality of reaction compartments are in fluid communication with at least some of the plurality of indicator compartments in the second position.

In some embodiments, the plurality of reaction compartments comprises a component required for the amplification reaction. In some embodiments, the plurality of indicator compartments comprises the amplification indicator. In some embodiments, the indicator compartments are transparent or translucent in part or in total and allow fluorescent measurement, detection of precipitate or gas bubble, or other visual observation. In some embodiments, the indicator compartments comprise a visual detector, a CCD, a CMOS sensor, a camera, a photon detector or an electrical sensor.

The present invention also provides a computer-readable medium comprising stored instructions, wherein the instructions when executed by a processor cause the processor to: obtain a color image of the amplification reaction product wherein the amplification reaction product is generated by performing an amplification reaction on a sample and exposing a mixture for the amplification reaction to an amplification indicator; determine a first color intensity of the color image; determine a second color intensity of the color image; determine a ratio between the first color intensity and the second color intensity, wherein the ratio is indicative of the presence or absence of an amplified target in the amplification reaction product.

In some embodiments, the instructions further cause the processor to apply a threshold to the ratio to generate a binary readout of positive and negative reactions. In some embodiments, the threshold changes depending on the amplification indicator.

In some embodiments, the mixture for the amplification reaction is exposed to the amplification indicator during the step of performing the amplification reaction. In some embodiments, the mixture for the amplification reaction is exposed to the amplification indicator subsequent to the step of performing the amplification reaction.

In some embodiments, the color image comprises images of a plurality of compartments. In some embodiments, the instructions further cause the processor to identify pixels corresponding to each of the plurality of compartments in the color image or the updated image. In some embodiments, the first color intensity and the second color intensity are an average of color intensities corresponding to a same group of pixels within one of the plurality of compartments. In some embodiments, the instructions cause the processor to determine the first color intensity and the second color intensity for each of the plurality of compartments.

In some embodiments, the instructions cause the processor to determine the ratio between the first color intensity and the second color intensity for each of the plurality of compartments to generate a plurality of compartment color ratios, wherein each of the compartment color ratios corresponds to each of the plurality of compartments. In some embodiments, the instructions cause the processor to generate a binary readout for each of the plurality of compartments to generate a plurality of compartment binary readouts, wherein each of the compartment binary readouts corresponds each of the plurality of compartments. In some embodiments, the instructions further cause the processor to generate a binary image using the compartment binary readouts. In some embodiments, the instructions further cause the processor to determine a concentration of the target nucleic acid within the sample based on the distribution of the compartment binary readouts. In some embodiments, the instructions further cause the processor to determine a presence or an absence of the target nucleic acid within the sample based on the binary readout. In some embodiments, the instructions further cause the processor to generate a binary image using the binary readout. In some embodiments, the instructions further cause the processor to determine a presence or an absence of the target nucleic acid within the sample based on the binary image.

In some embodiments, the instructions further cause the processor to generate a report related to a composition of the sample. In some embodiments, the instructions further cause the processor to send the report to a receiver by email, SMS messaging, web posting, phone call, electronic messaging, uploading or downloading. In some embodiments, the report is related to the binary readout, the binary image, the presence or absence of the target nucleic acid within the sample, or the concentration of the target nucleic acid within the sample.

In some embodiments, the instructions cause the processor to determine the first color intensity and the second color intensity using a Red-Green-Blue (RGB) color scheme; cyan, magenta, yellow and key (black) (CYMK) color scheme; or L-A-B color scheme.

The present invention also relates to a system for visually detecting amplification of a target nucleic acid, comprising: an amplification reactor comprising one or more compartments configured to perform an amplification reaction on a sample, wherein (i) the sample has a volume ranging from 1 pL to 1 µL, or (ii) each compartment has an optical path length less than 1 mm; an unmodified camera configured to obtain a color image of a reaction product resulting from the amplification reaction; a processor; and the computer-readable medium.

In some embodiments, the system further comprises a detector for detecting light absorbance, light reflection, or light transmission of the reaction product at a plurality of wavelengths. In some embodiments, the detector detects light absorbance, light reflection, or light transmission of the reaction product at two different wavelengths. In some embodiments, the two different wave lengths are 540 nm and 650 nm.

In some embodiments, the system further comprises a housing. In some embodiments, the amplification reactor comprises a holder for the housing.

5. BRIEF DESCRIPTION OF THE DRAWINGS

FIG. 1 provides a flowchart summarizing a method of single-molecule counting using a camera phone.

Figure 2A:
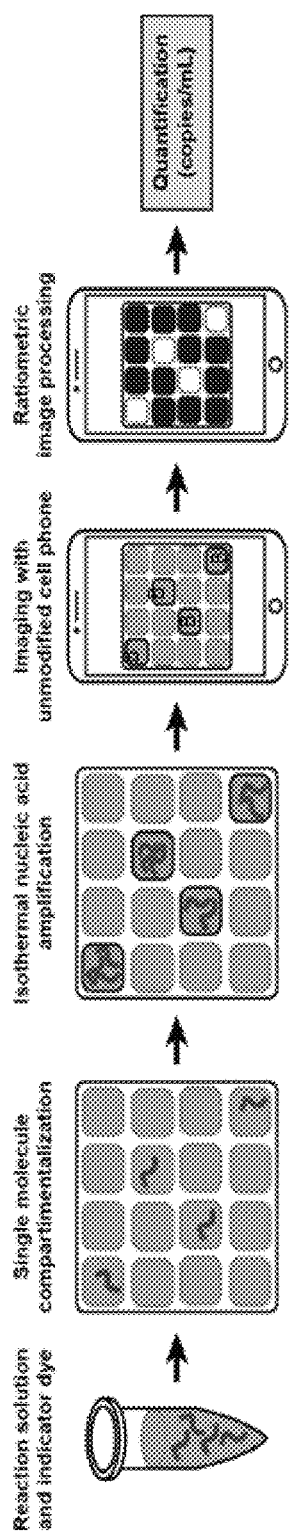
Figure 2B:
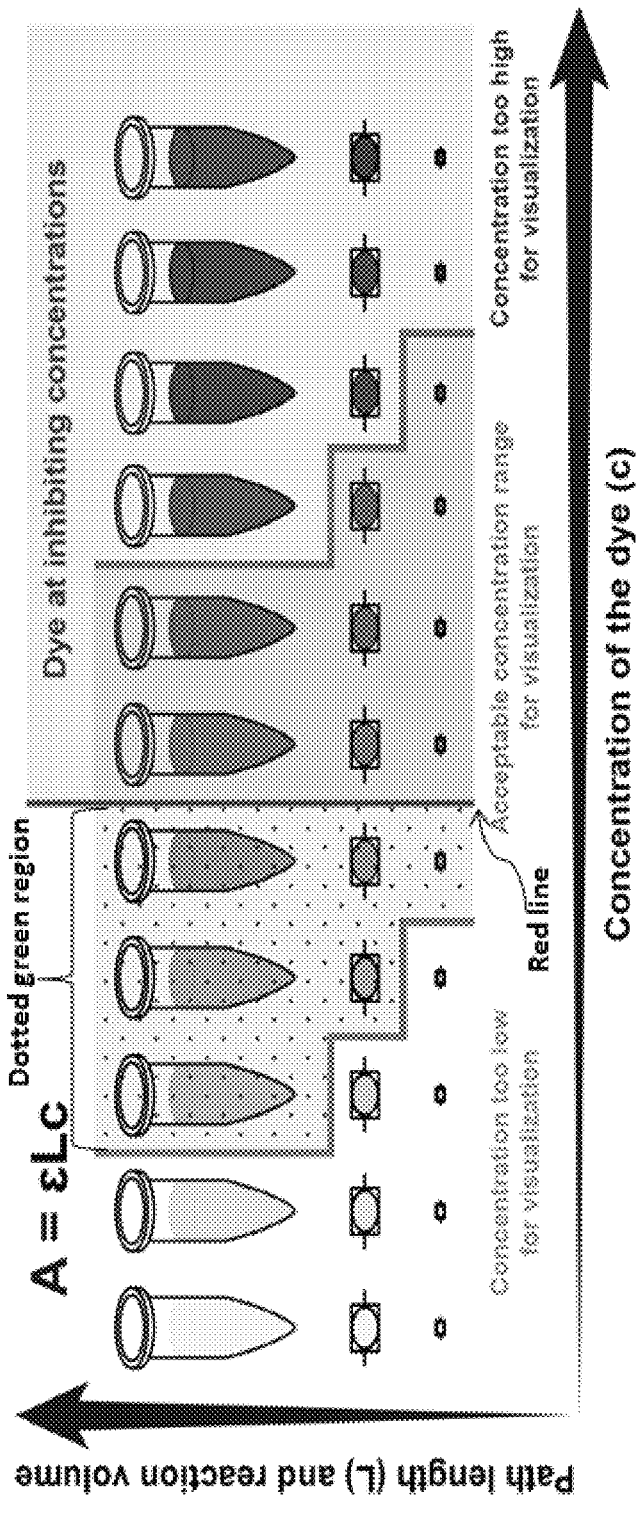

FIG. 2A outlines a visual readout approach for digital single-molecule isothermal amplification for use with an unmodified cell phone camera. FIG. 2B is a diagram delineating the optimal range of dye concentrations as a factor of path length (reaction volume) and the threshold for reaction inhibition.

Figure 3A:
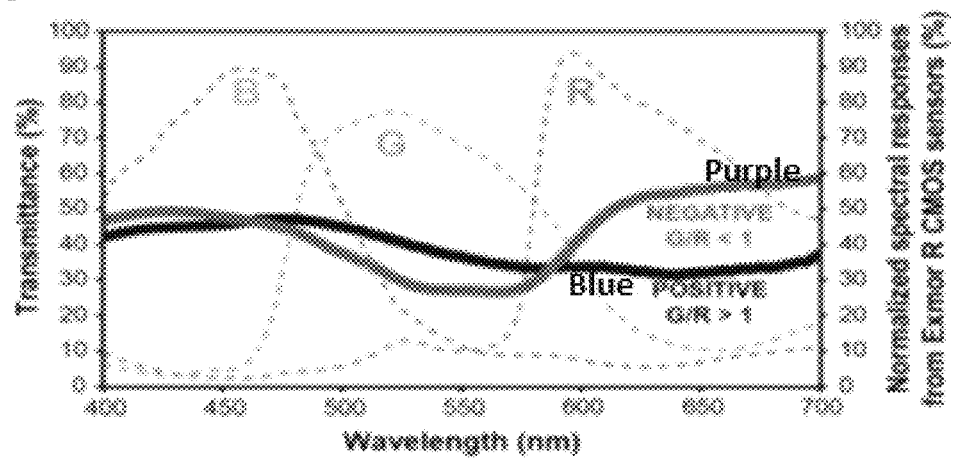
Figures 3B, 3C:
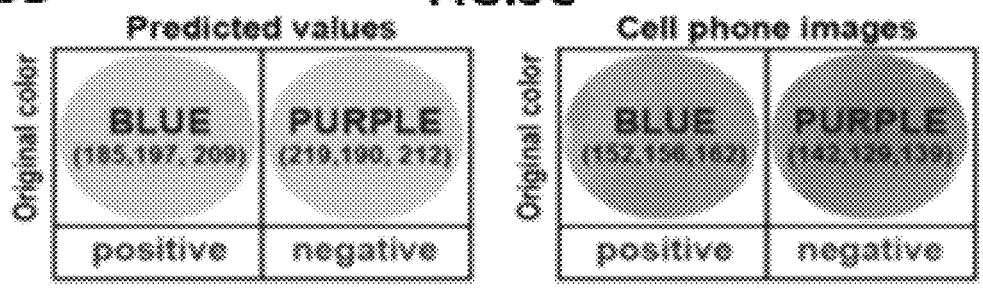
Figures 3D, 3E:
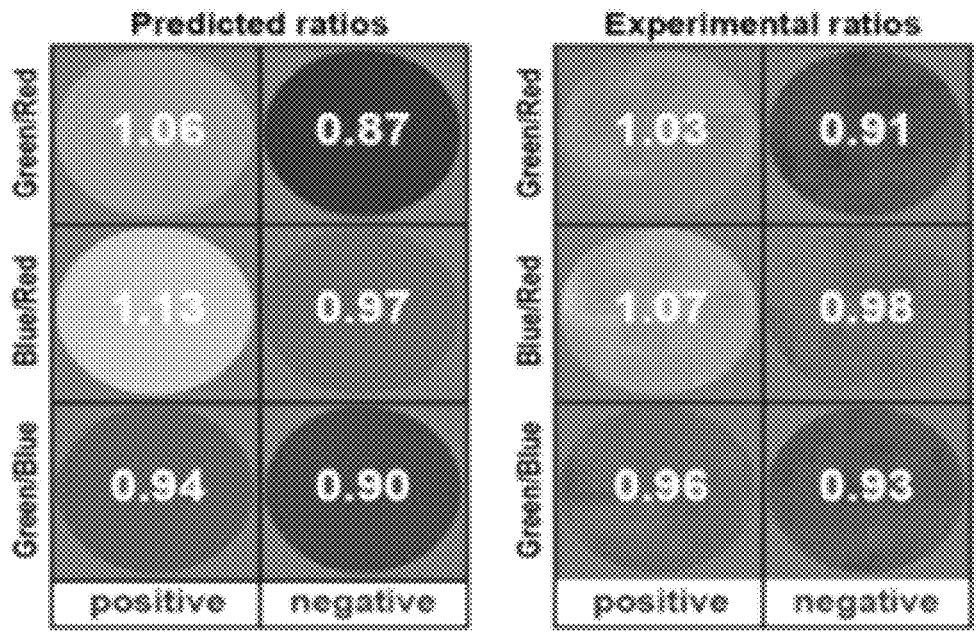

FIG. 3A-3E provides predicted values and experimental validation of the first step of the ratiometric approach. FIG. 3A presents measured spectral transmittance (%) in the range of visible light (400-700 nm) for positive (solid blue line) and negative (solid purple line) RT-LAMP reaction solutions, each containing 0.7 mM of eriochrome black T (EBT) as the amplification indicator dye. Dashed lines correspond to normalized spectral responses for red (R), green (G) and blue (B) channels of an Exmor R CMOS sensor, a common sensor in cell phone cameras. FIG. 3B provides the predicted RGB values and corresponding colors for positive and negative LAMP amplification reactions obtained by convoluting the transmittance spectrum and Exmor R spectral responses described in FIG. 3A. FIG. 3C is the cropped and enlarged color images collected with an Apple iPhone 4S for positive and negative RT-LAMP reaction solutions containing 90 µM of EBT dye. FIG. 3D is predicted images and ratiometric values for positive and negative amplification reactions processed for each ratiometric combination, G/R, B/R and G/B. FIG. 3E is experimental images and ratiometric values for positive and negative amplification reactions for each combination: G/R, B/R and G/B. All experiments were performed with HCV RNA as template.

FIGS. 4A, 4C, and 4E present measured spectral transmittance (%) in the range of visible light (400-700 nm) for positive (solid blue line, labeled as "POSITIVE") and negative (solid purple line, labeled as "POSITIVE") RT-LAMP reaction solutions, each containing 0.7 mM of eriochrome black T (FIG. 4A), hydroxynaphthol blue (FIG. 4C) or calmagite (FIG. 4E) as the amplification indicator dye. Dashed lines correspond to normalized spectral responses for red (R), green (G) and blue (B) channels of an Exmor R CMOS sensor, a common sensor in cell phone cameras.

FIGS. 4B, 4D, and 4F present predicted ratiometric values for positive and negative LAMP amplification reactions processed for each ratiometric combination, Green/Red, Blue/Red and Green/Blue. Tables show absolute differences (positive-negative) and the relative difference (in %) between positive and negative ratiometric values in RT-LAMP reactions, each containing 0.7 mM of eriochrome black T (FIG. 4B), hydroxynaphthol blue (FIG. 4D) or calmagite (FIG. 4F) as the amplification indicator dye. All experiments were performed with HCV RNA as a template.

Figure 5A:
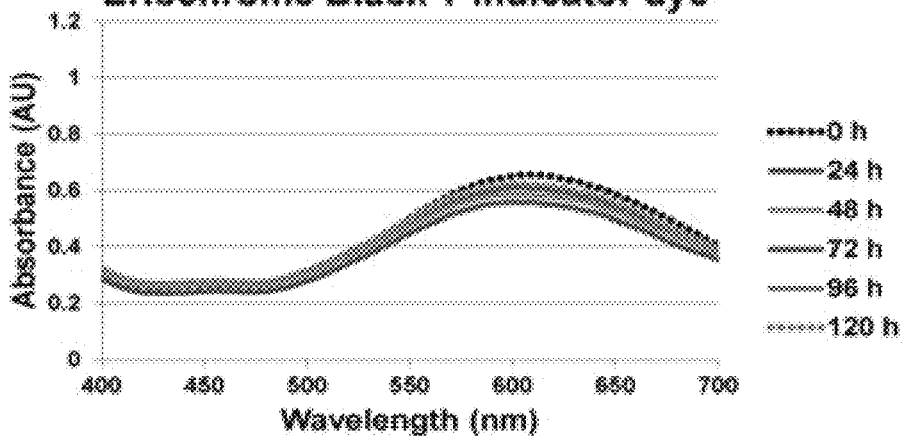
Figure 5B:
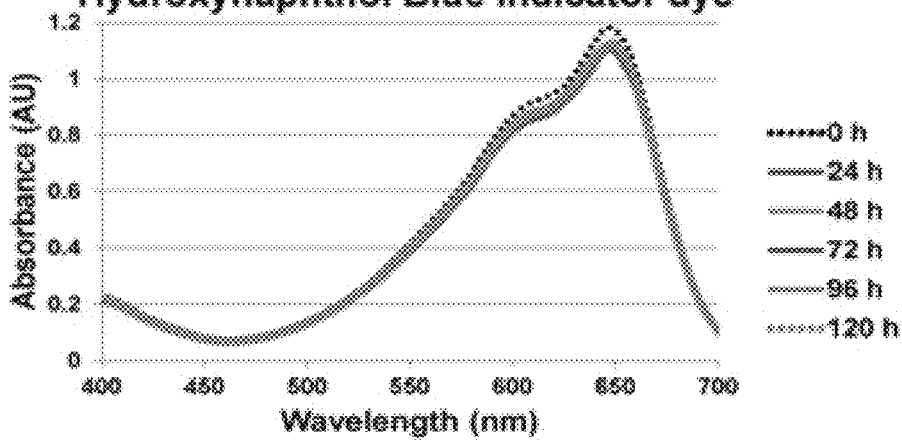
Figure 5C:
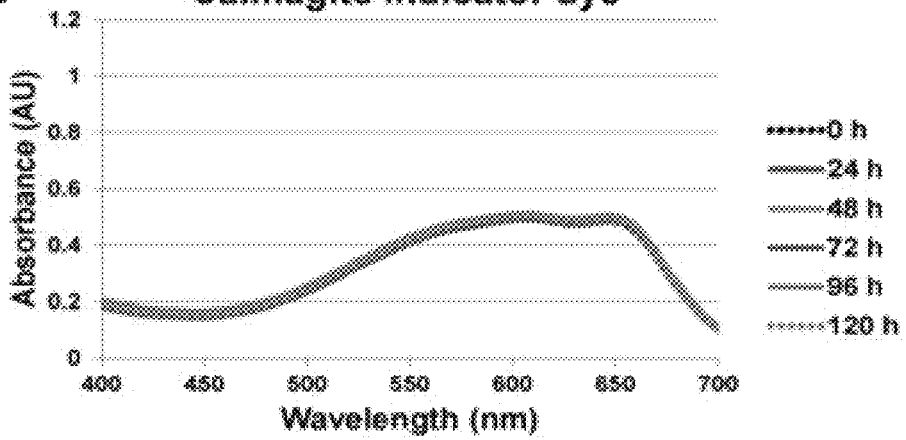

FIG. 5A-C provides graphs illustrating storage stability of amplification indicator dyes by drying the stock solutions in the presence of stabilizer trehalose. Measured spectral absorbance (Absorbance Units) are provided in the range of visible light (400-700 nm) for eriochrome black T (EBT) (FIG. 5A), hydroxynaphthol blue (HNB) (FIG. 5B), and calmagite indicator dyes solutions (FIG. 5C).

FIG. 6A-G illustrates validation of the robustness of the G/R ratiometric approach using different hardware (cell phone cameras) and lighting conditions. FIGS. 6A-D provide images captured by four common cell phones under fluorescent light: FIG. 6A Apple iPhone 4S, FIG. 6B HTC inspire 4G, FIG. 6C Motorola Moto G and FIG. 6D Nokia 808 PureView. FIGS. 6E-G provide images captured by an Apple iPhone 4S under three additional light conditions: FIG. 6E incandescent light, FIG. 6F direct sunlight and FIG. 6G indirect sunlight. All experiments were performed with HCV RNA as a clinically relevant target. All images were acquired with unmodified cell phone cameras.

Figure 7:
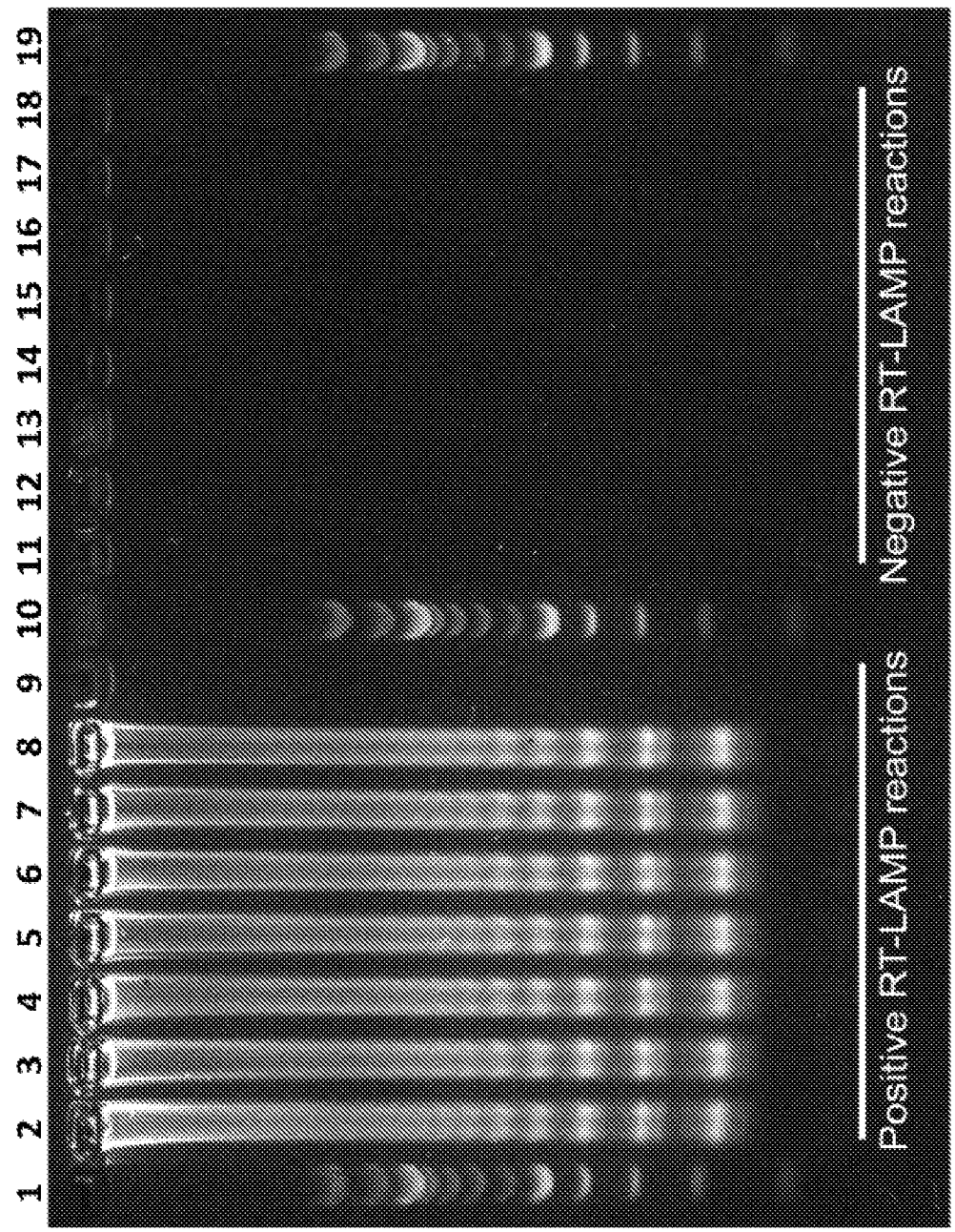

FIG. 7 is a picture of a DNA gel electrophoresis of RT-LAMP product. Lanes 1, 10 and 19 are 100 bp DNA ladders. Lanes 2-9 are positive with (HCV RNA) RT-LAMP reactions, each lane with two-fold increased Eriochrome Black T concentration (from 0.011 to 1.4 mM). Lanes 11-18 are negative with RT-LAMP reactions, each lane with two-fold increased Eriochrome Black T concentration (from 0.011 to 1.4 mM). Lane 9 shows an inhibited RT-LAMP reaction in the presence of 1.4 mM Eriochrome Black T solution.

FIGS. 8A-E outlines steps of the G/R process algorithm.

FIGS. 9A-G provide original acquired with unmodified cell phone cameras (left) and images produced by ratiometric image processing (right).

Figure 10:
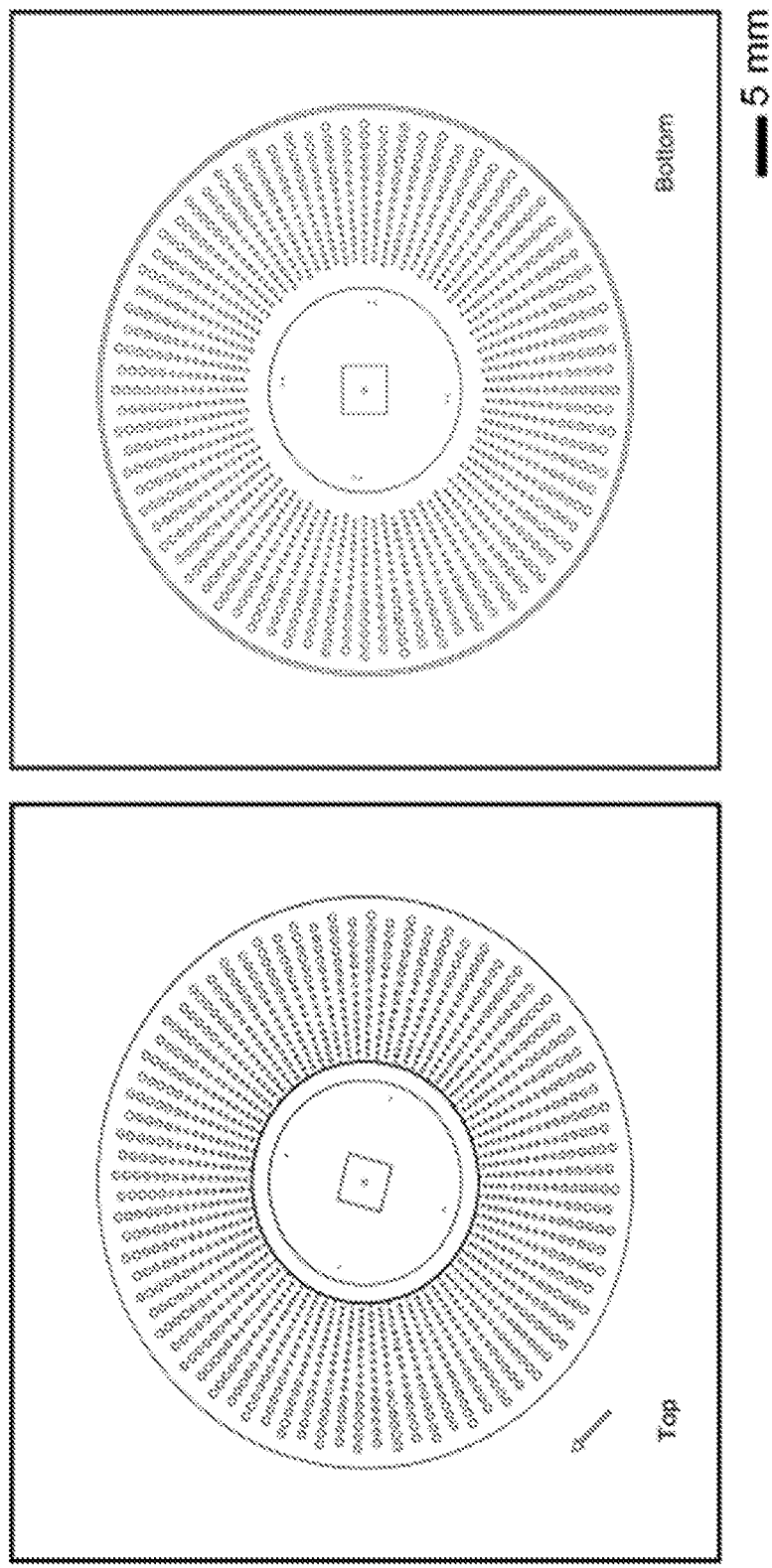

FIG. 10 is a schematic image of the top (left) and bottom (right) plates of the multivolume rotational SlipChip device used in the one-step digital LAMP experiments before being assembled. The top plate shows the direction of the rotational 4.5° slip.

FIGS. 11A and 11B provides schematic images of the multivolume rotational SlipChip device used for one-step digital LAMP experiments after being assembled. Drawing shows the layout of top and bottom piece of the entire device on the right and a zoomed-in region (black box) on the left. FIG. 11A shows relative position of the two pieces when they are aligned to allow loading of solution through the channel, and FIG. 11B shows the relative position of the two pieces when they are slipped (top slide rotated 4.5°) to separate droplets from one another and form compartments. Features shown are before isotropic glass etching.

FIG. 12A-C present readouts from single-molecule digital LAMP reactions performed with lambda DNA on a multivolume rotational SlipChip device imaged by a stereoscope (FIG. 12A), a fluorescence microscope (FIG. 12B) and an unmodified cell phone camera (FIG. 12C). In FIGS. 12D-H, callouts are magnified to show visual correlation among the three imaging methods. FIG. 12D shows the results of the ratiometric processing for the stereoscope G/R processed image and FIG. 12H shows the cell phone G/R-processed image. Colors were enhanced in these figures for clarity of publication; raw images were used in all ratiometric analyses. These devices contained 1,240 wells of eight volumes ranging from 15 nL to 50 nL.

Figure 13:
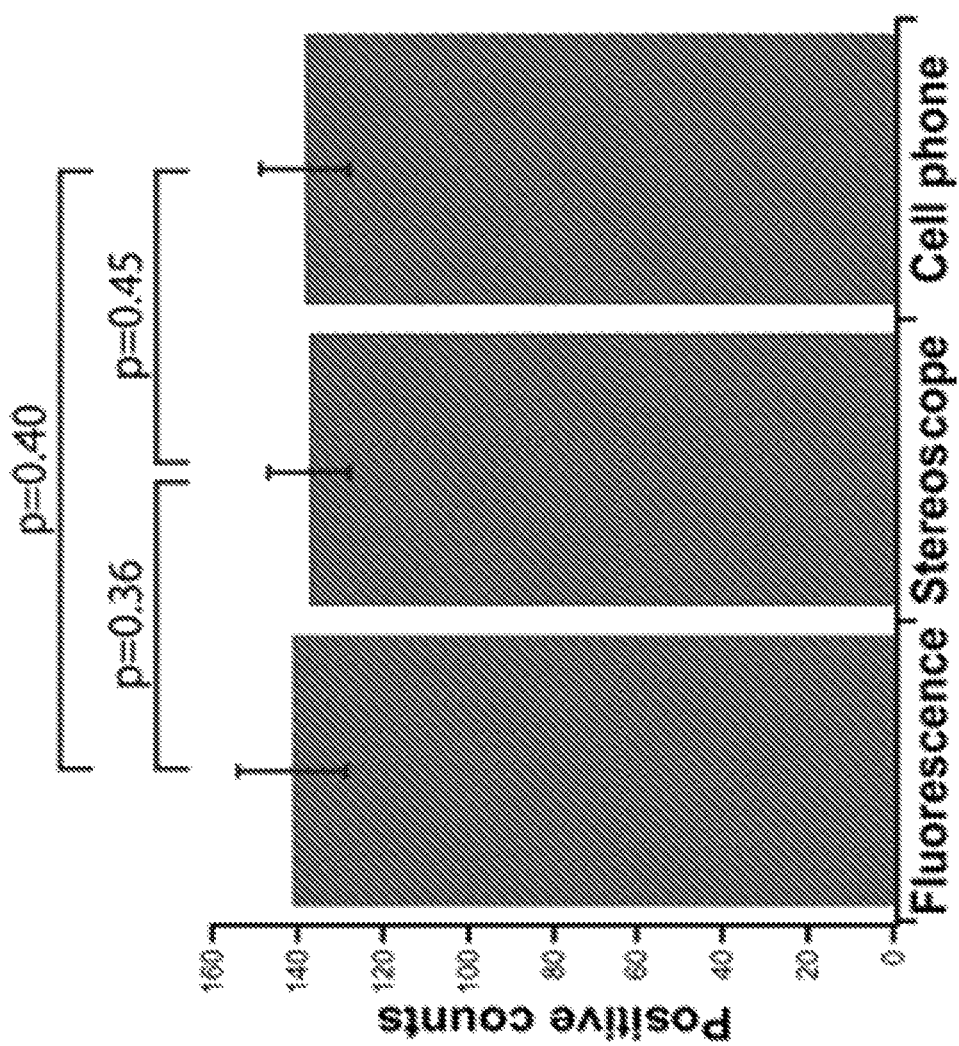

FIG. 13 provides a graph obtained from single-molecule digital LAMP reactions performed with lambda DNA on a one-step SlipChip device as described in Example 14. Each bar represents positive counts obtained from images capture with a house-built real-time fluorescence microscope, a Leica MZ Fl III stereoscope, or an unmodified cell phone camera (Apple iPhone 4S) under fluorescent light.

Figure 14A:
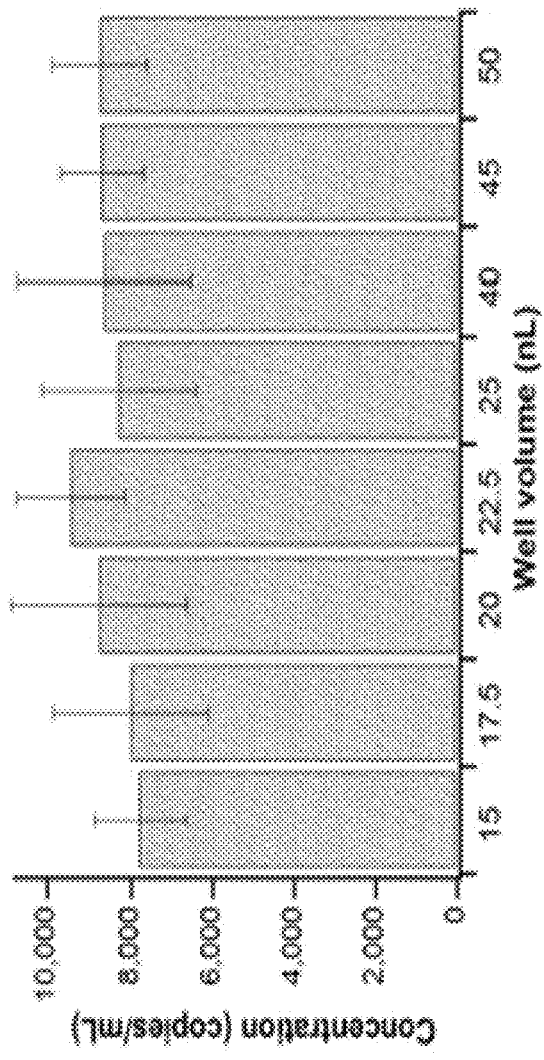
Figure 14B:
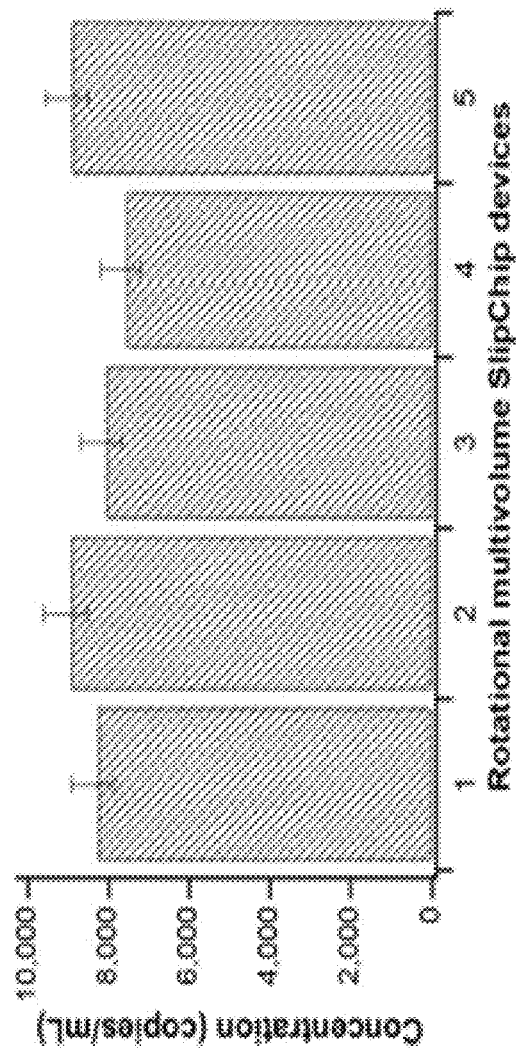

FIGS. 14A and 14B demonstrates robustness of digital visual readout at different well volumes. Concentration of lambda DNA was estimated by digital LAMP using five multivolume rotational SlipChip devices, each of which contained eight well volumes ranging from 15-50 nL. FIG. 14A shows measured template concentration for each well volume averaged over five devices. FIG. 14B shows mean template concentration for each of five rotational SlipChip devices. Concentrations were calculated using MPN theory and error bars represent standard deviation. Images were captured by a stereoscope and processed with the ratiometric approach (G/R process).

Figure 15:
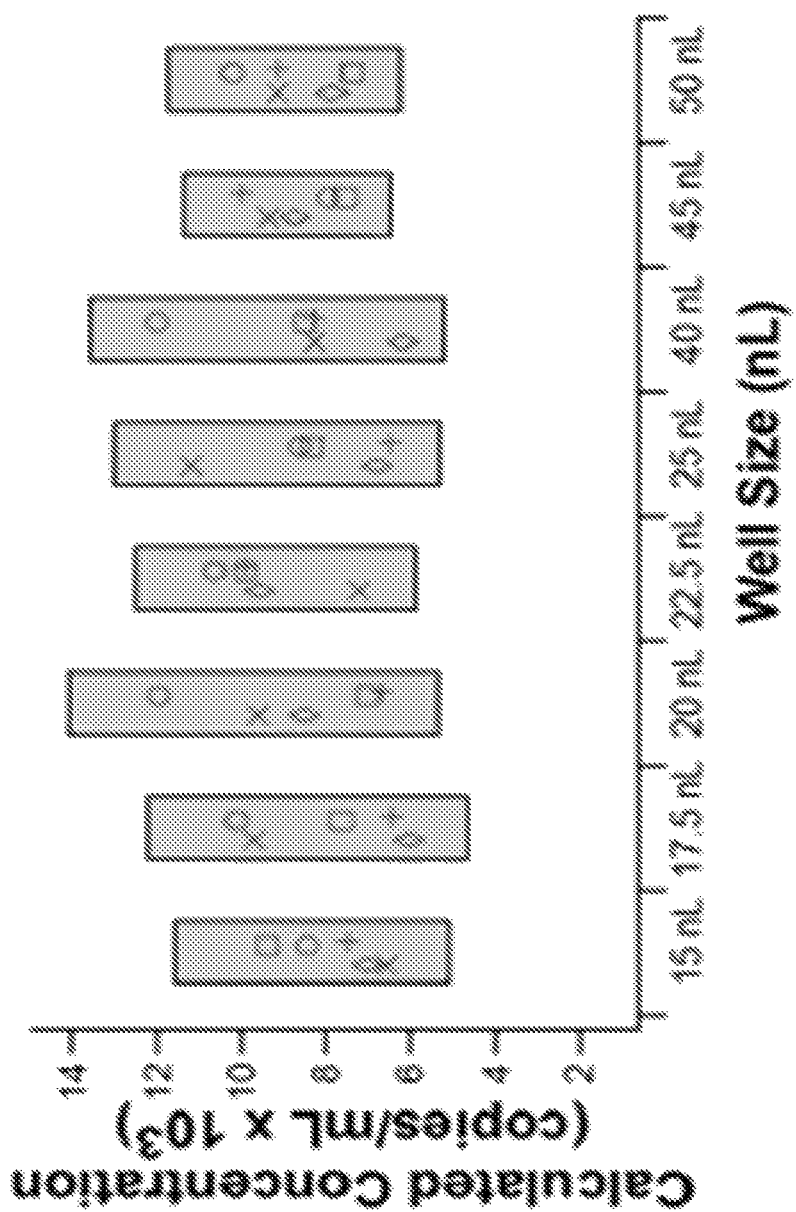

FIG. 15 provides a graph obtained from five multivolume experiments. The graph presents concentrations calculated at each volume with gray boxes denoting the 95% confidence interval for the set of experiments at each volume.

Figure 16:
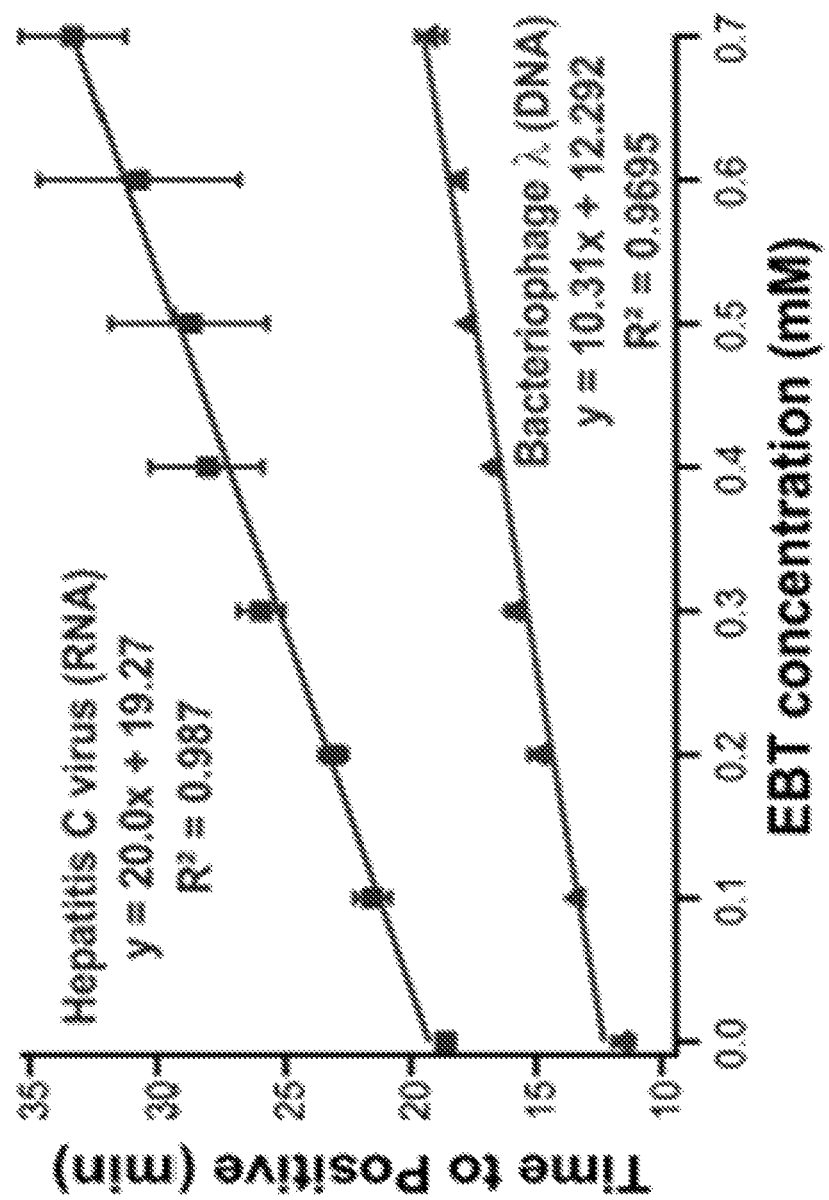

FIG. 16 is a graph illustrating time to show positive in bulk LAMP reactions at increasing concentrations of the amplification indicator dye eriochrome black T (EBT). All reactions performed in 10 µL volumes with concentrations of EBT solution ranging from 0.0 to 0.7 mM, SYTO® 9 Stain and either 1,000 copies of HCV RNA (red) or 1,000 copies of phage lambda DNA (blue). All reactions were run in triplicate.

Figures 17A, 17B:
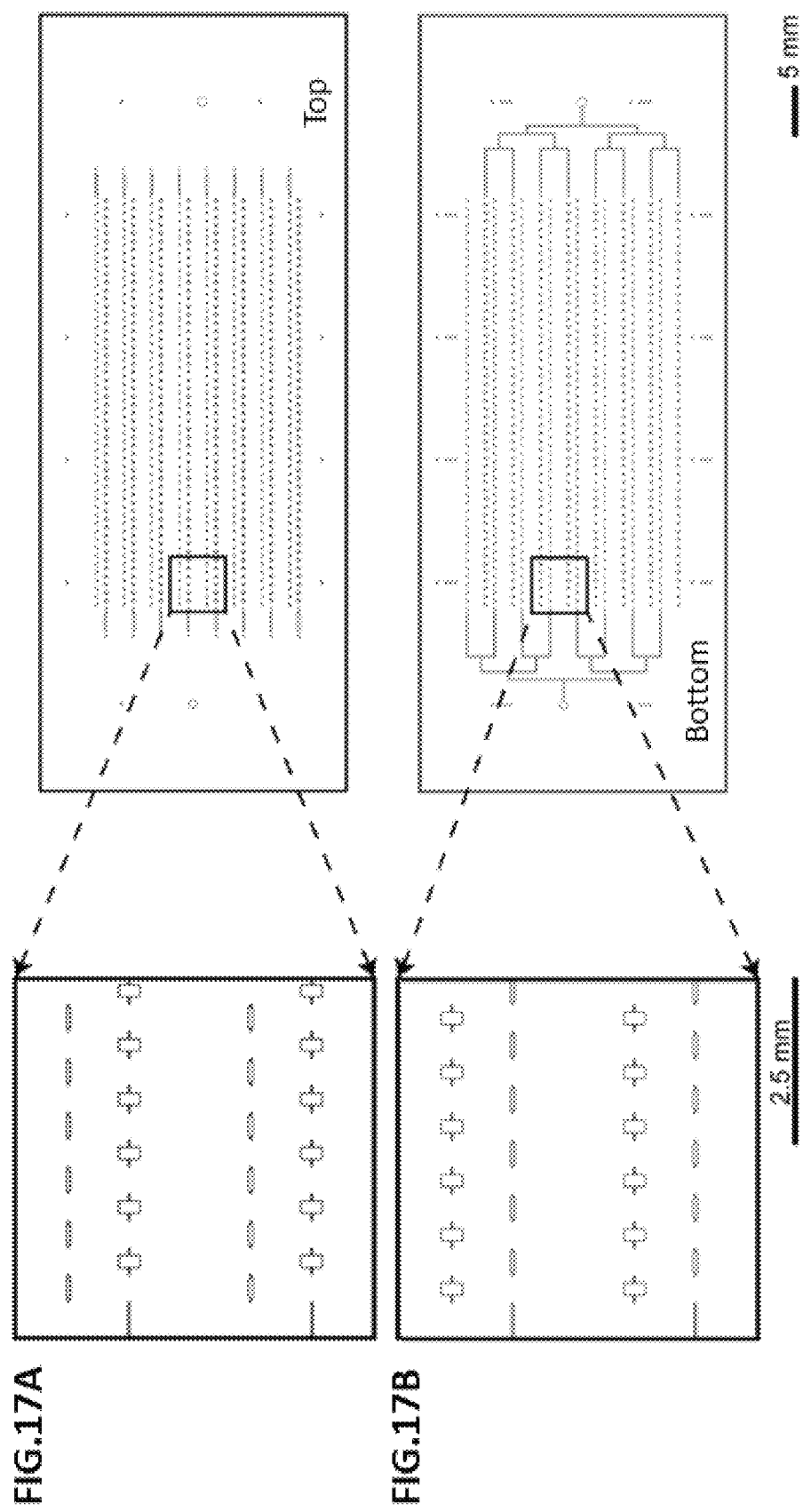

FIGS. 17A and 17B provides a schematic of the two-step SlipChip device before assembly. Drawings show the top (FIG. 17A) and bottom (FIG. 17B) device plates with a selected region (black box) magnified on the left to show locations of the 5 nL and 9.5 nL wells. Features are shown before isotropic glass etching.

FIG. 18A-D provides a schematic of the two-step SlipChip device after assembly and its operation. Drawings show the layout of the top and bottom plates on the right and a magnified region (black box) on the left. FIG. 18A presents a loading conformation for the first set of wells (5 nL each). FIG. 18B shows a loading conformation for the second set of wells (9.5 nL each). FIG. 18C shows an incubation conformation. FIG. 18D shows a final mixing conformation ready for imaging with a cell phone camera. Features are shown before isotropic glass etching.

Figure 19:
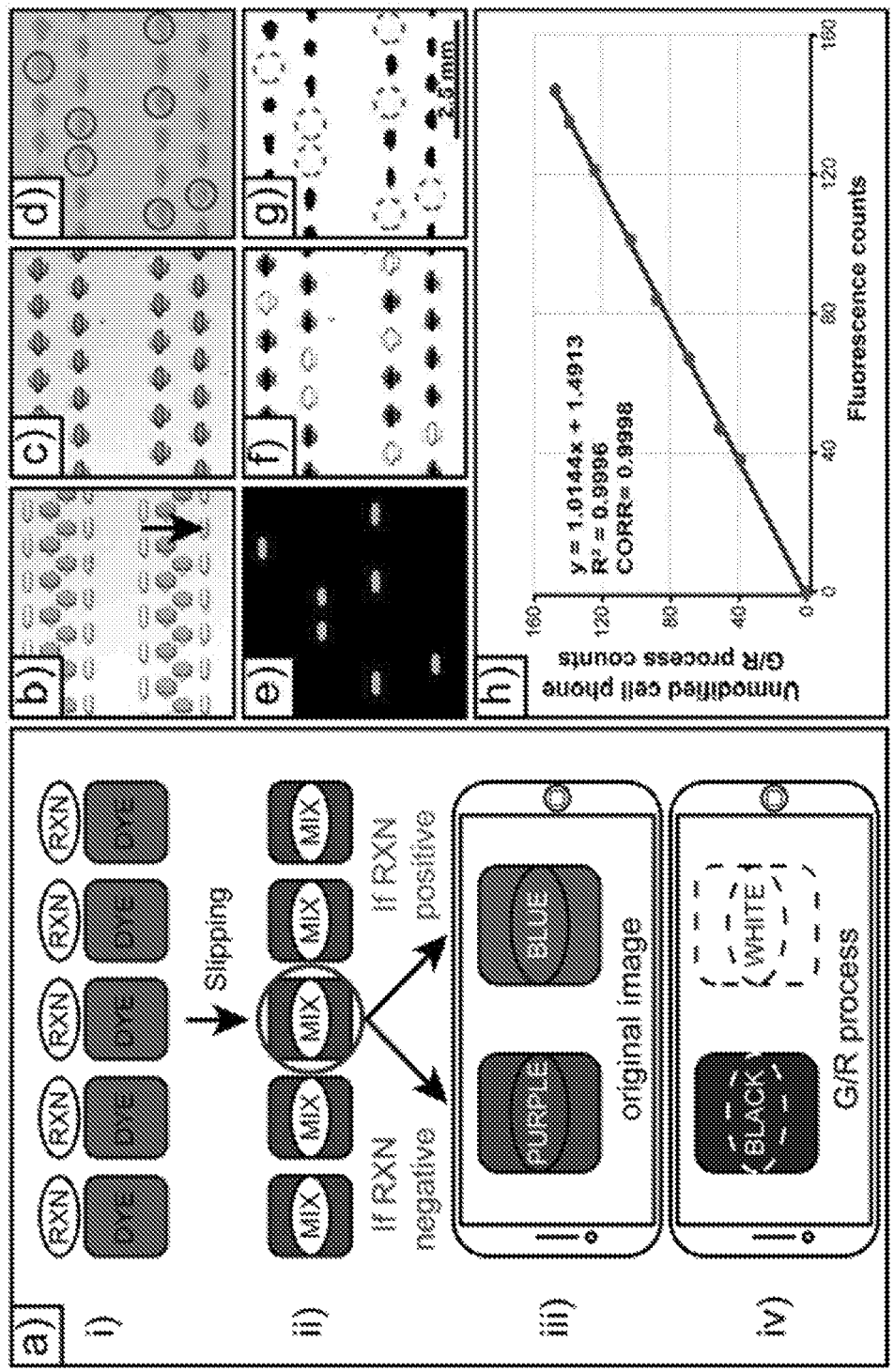

FIG. 19 shows experimental validation of two-step SlipChip devices for single molecule counting with an unmodified cell phone camera. Part a) A flow-chart of detection of single molecules in two-step SlipChip. Part b) presents stereoscope image of the device before the amplification and readout wells are merged (arrow designates direction of slip). Stereoscope image (part c)), cell phone camera image (part d)) and fluorescent images (part e)) after the device is slipped and the wells are merged are also provided. Also provided are stereoscope image (part f)) and cell phone camera image (part g)) after G/R image processing. Part h) shows correlation between fluorescence counts and cell phone (G/R processed) counts. Colors were enhanced in figure panels (parts b)-f)) for clarity of publication; raw images were used in all ratiometric analyses. In these experiments HCV RNA was amplified by dRT-LAMP.

Figure 20A:
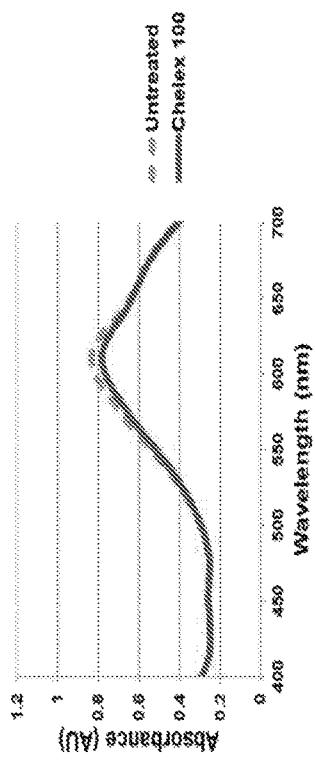
Figure 20B:
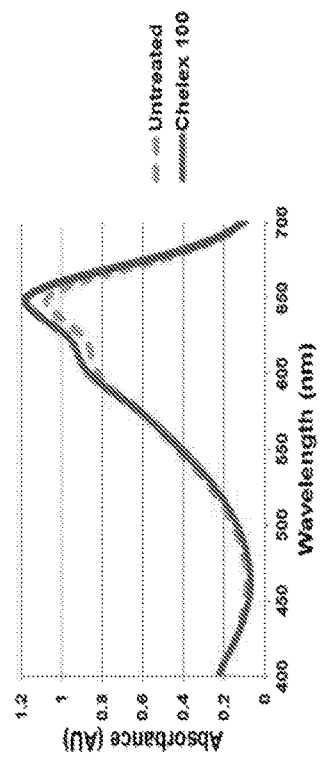
Figure 20C:
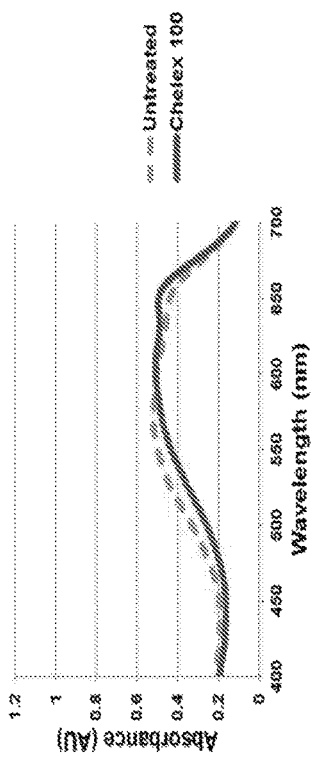

FIG. 20A-C presents comparison of the spectral absorbance (Absorbance Units) of untreated indicator dye stock solutions (dashed orange lines) and solutions treated with Chelex® 100 resin (solid red lines) for eriochrome black T (EBT) (FIG. 20A), hydroxynaphthol blue (HNB) (FIG. 20B) and calmagite indicator dyes (FIG. 20C). The EBT, HNB and calmagite stock solutions were prepared by dissolving the dyes in 20 mM Tris-HCl buffer (pH 8.8) at 0.7 mM. The solutions were sonicated for 10 min and mixed on a rotator at room temperature for 1 h. The solutions were split into two equal volumes for the comparison; one volume was treated with Chelex® 100 ion exchange resin (5% w/v).

Figure 21:
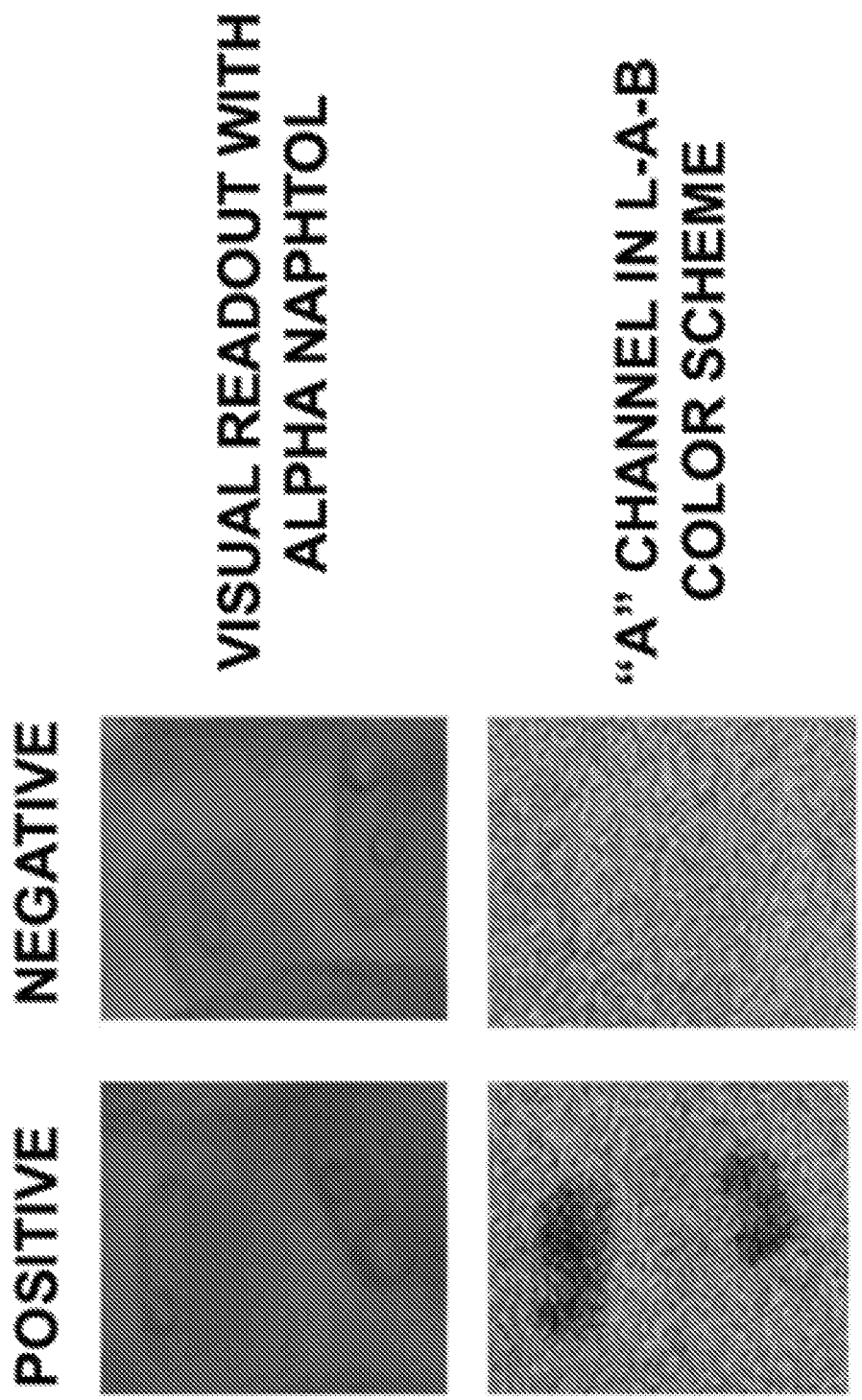

FIG. 21 provides data from Example 2, with original images of reaction products from LAMP amplification of lambda DNA in the presence of hydroxynaphthol blue (top). The bottom panels show results from ratiometric image processing of the original images.

Figure 22:
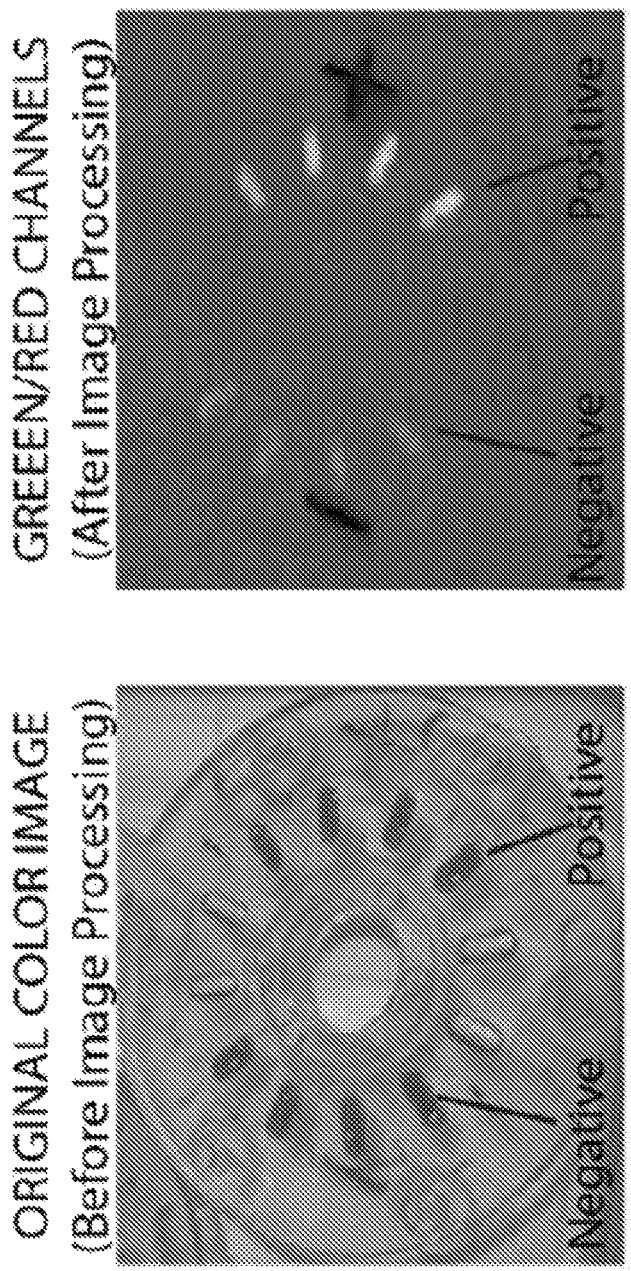

FIG. 22 provides data from Example 3. An original image of a product obtained from RT-LAMP amplification of HCV RNA in the presence of hydroxynaphthol blue is presented on the left. The original image was processed with the ratiometric approach (G/R process) and provided on the right.

Figure 23:
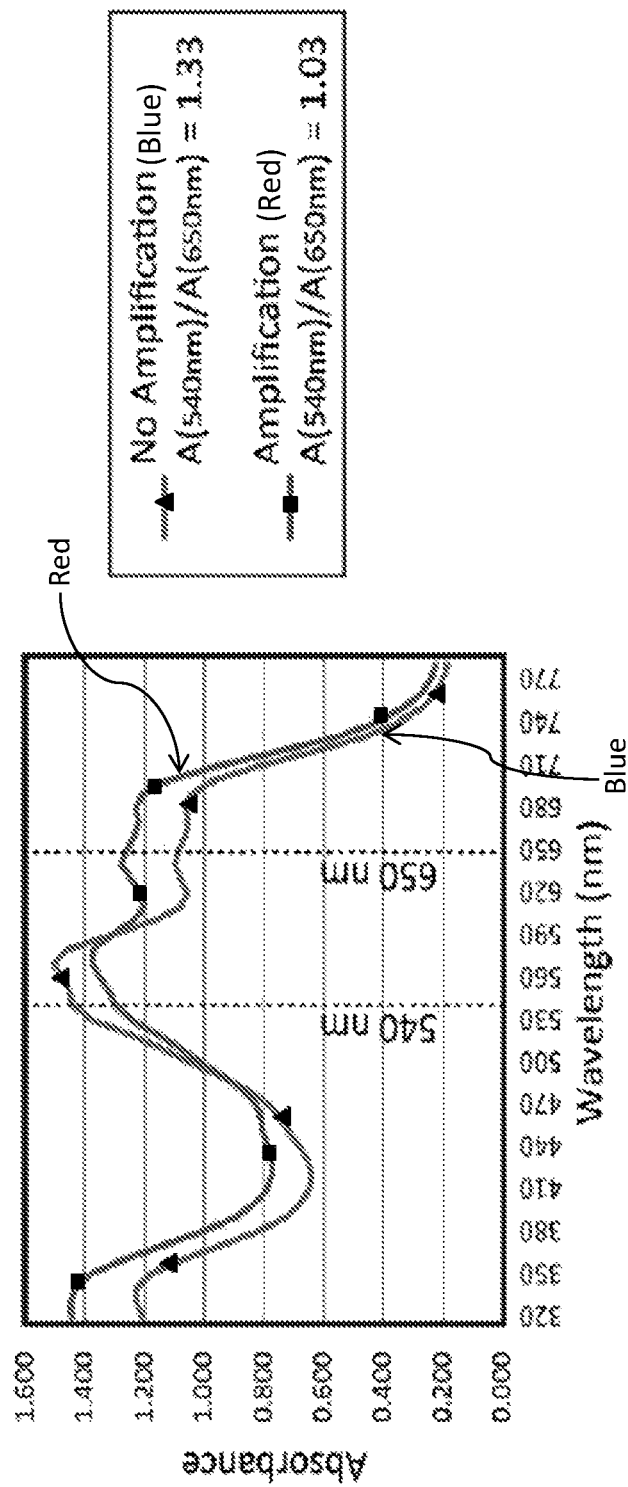

FIG. 23 is a graph providing absorbance spectrum of a LAMP amplification product (red line with rectangles) and a negative solution (blue line with triangles) in the presence of Eriochrome Black T. The graph is based on data from Example 4.

FIG. 24A-F includes six graphs illustrating absorbance spectrum of a LAMP amplification product (red line with rectangles); and a negative control (blue line with triangles), either on Day 0 (FIG. 24A-C) or Day 3 (FIG. 24D-F). The absorption was measured in the presence of one of three amplification indicators—Eriochrome Black T (FIG. 24A, 24D), Alpha Napthol Blue (FIG. 24B, 24E) and Calmagite (FIG. 24C, 24F). The graphs are based on data from Example 5.

FIG. 25 presents data from one-step reaction described in Example 6. The figure includes an original image of a SlipChip device with LAMP amplification of a phage lambda DNA molecule. Positive wells are blue (labeled "B") and negative wells are purple (not labeled) in the presence of Eriochrome Black T (left). The image was processed with the ratiometric approach (G/R process) and presented on the right.

Figure 26A:
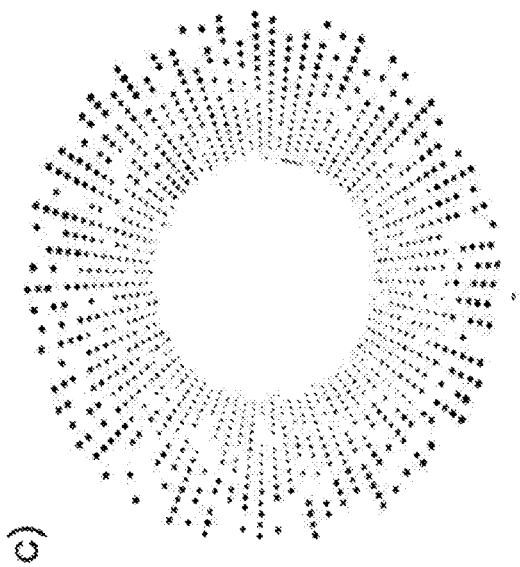
Figure 26B:
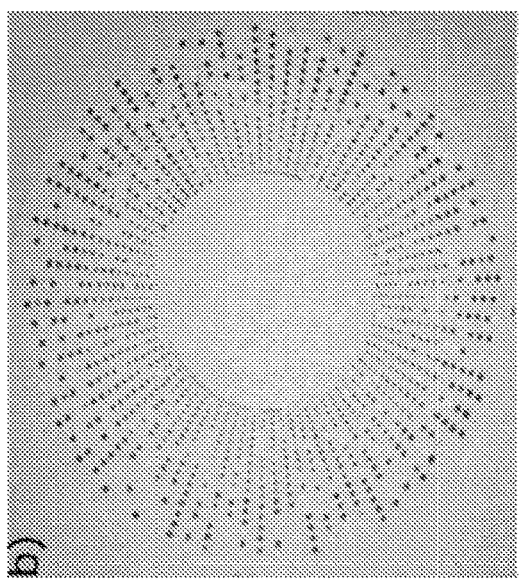
Figure 26C:
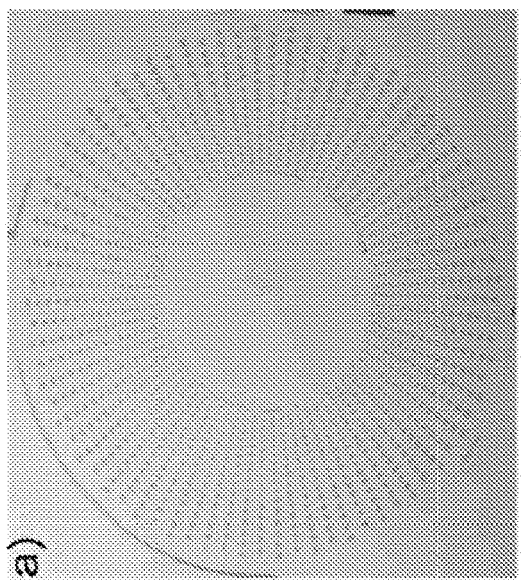

FIG. 26A-C provides data from one-step reaction described in Example 7. FIG. 26A provides an original cell phone image of a SlipChip device with LAMP amplification of a phage lambda DNA molecule in the presence of Eriochrome Black T. The image was processed with the ratiometric approach (G/R process) and presented as FIG. 26B. The processed image was then adjusted based on a threshold and provided as a B/W (binarized) image in FIG. 26C.

FIG. 27 provides data from one-step method described in Example 8. FIG. 27A provides an original fluorescence image (SYTO60) of a 27 nL well with amplification of single phage lambda DNA molecule in the presence of Eriochrome Black T. FIG. 27B provides an image of the same area captured with the stereoscope, where positive wells are blue (with a dot) and negative wells are purple (without a dot). FIG. 27C shows the result from the ratiometric image processing, by splitting the color channels and then dividing the green channel signal by the red channel signal.

Figure 28C:
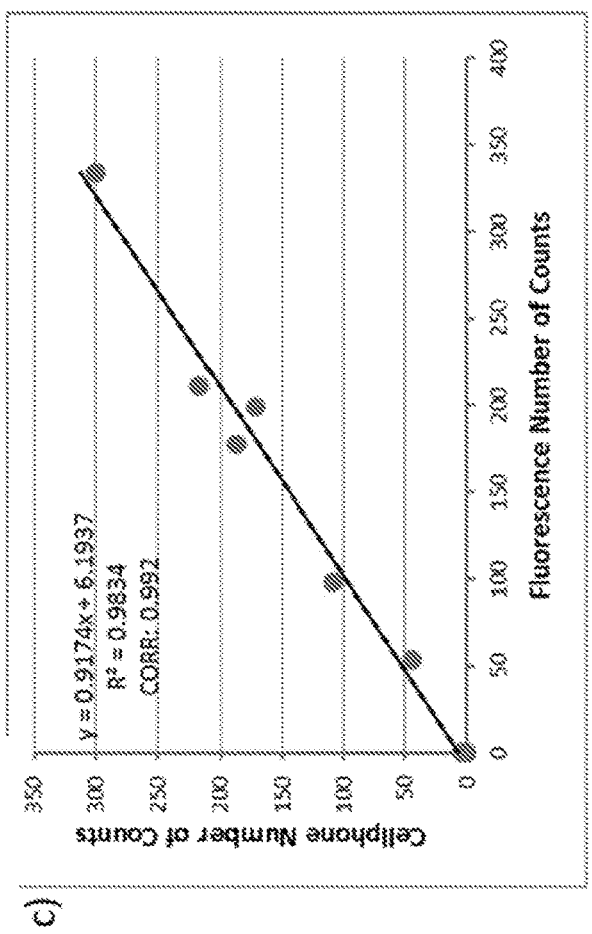
Figure 28A:
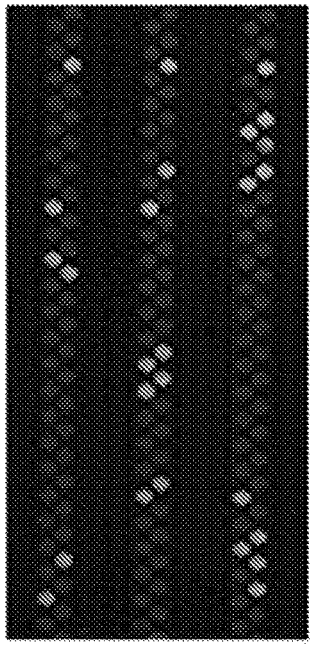
Figure 28B:
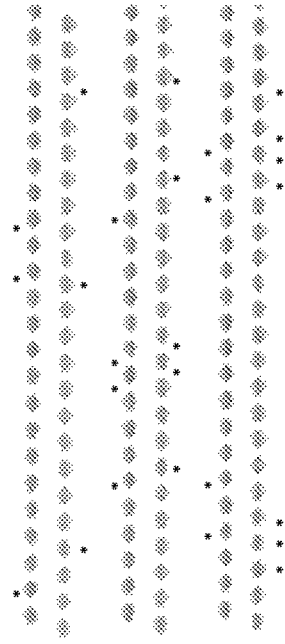

FIG. 28A-C provides data from two-step method described in Example 9. FIG. 28A provides a calcein fluorescence image of 17 nL wells with amplification of single phage lambda DNA molecules in the presence of Eriochrome Black T. FIG. 28B shows an image of the same area acquired with an unmodified cell phone camera (Apple iPhone 4S) where positive wells are blue (with a dot) and negative wells are purple (without a dot). FIG. 28C provides a plot showing the correlation between fluorescent and bright field single-molecule counts acquired by fluorescence microscopy and unmodified cell phone (after image processing), respectively.

FIG. 29A-C provides data from two-step method described in Example 10. FIG. 29A provides an original fluorescence image (SYTO9) of a 5 nL well with RT-LAMP amplification of HCV RNA molecules. FIG. 29B shows an image of the same area captured with the stereoscope, where positive wells are blue (with a dot) and negative wells are purple (without a dot). FIG. 29C shows the result from ratiometric image processing, by splitting the color channels and then dividing the green channel signal by the red channel signal.

Figure 30:
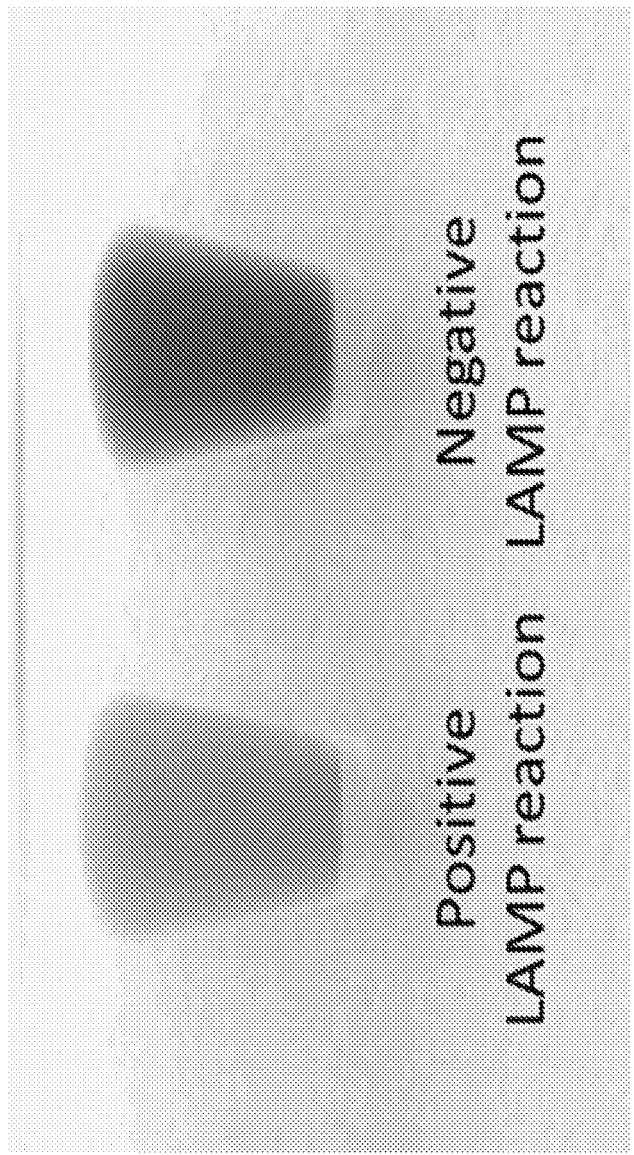

FIG. 30 provides data from two-step method described in Example 11. The figure presents an image of two tubes—a tube with negative reaction (right—red) and another tube with amplification of phage lambda DNA (left—yellow-green) in the presence of Hematoxylin-based solution.

Figure 31:
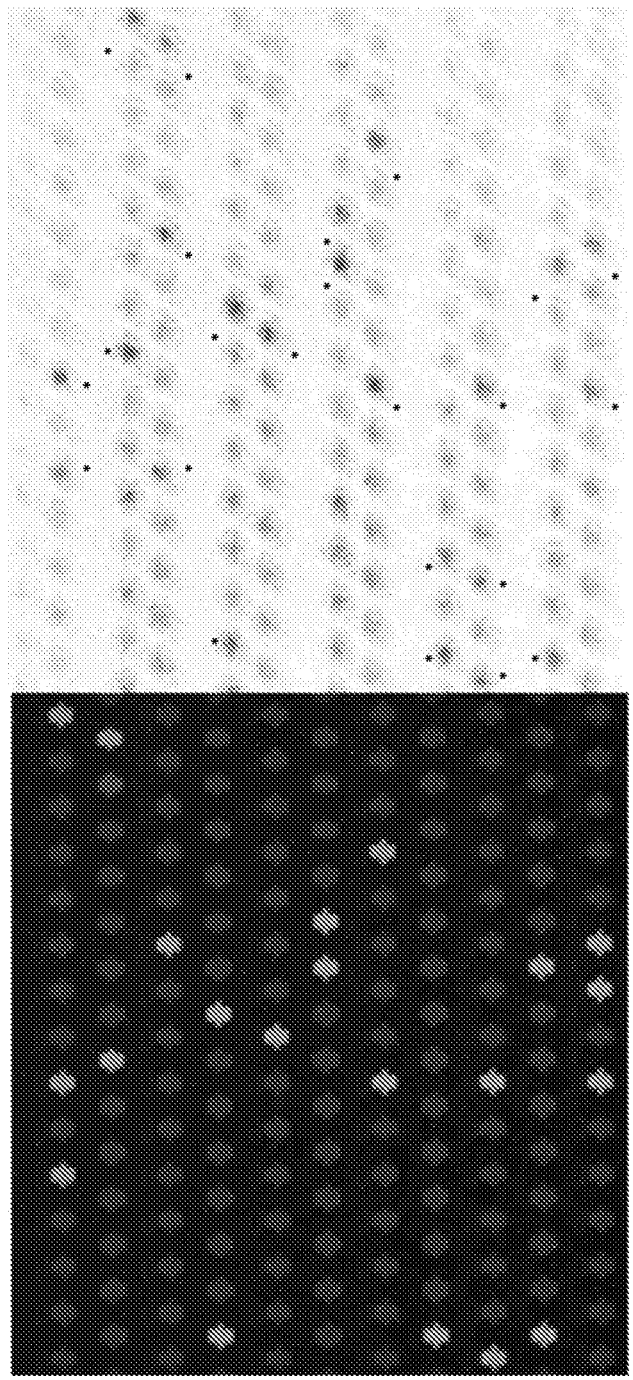

FIG. 31 provides data from two-step method described in Example 12. FIG. 31 (left) shows a fluorescent digital pattern of a SlipChip device with LAMP amplification of phage lambda DNA in the presence of hematoxylin-based amplification indicator. FIG. 31 (right) is a bright field image of the same area, where positive wells are red (with a dot) and negative wells are yellow (without a dot).

Figure 32B:
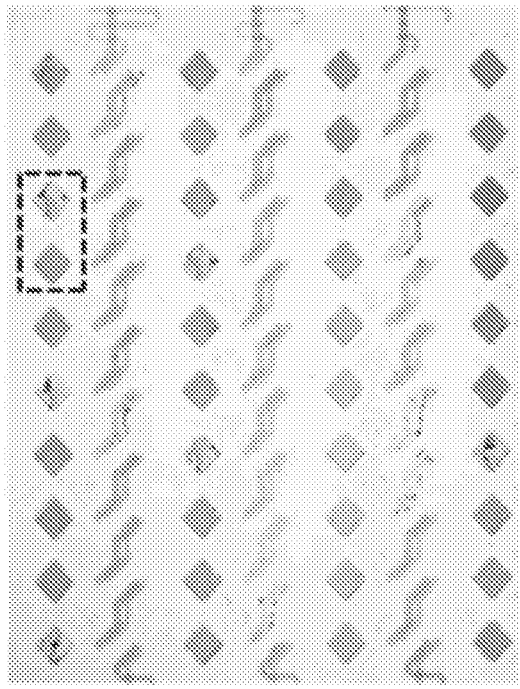
Figure 32C:
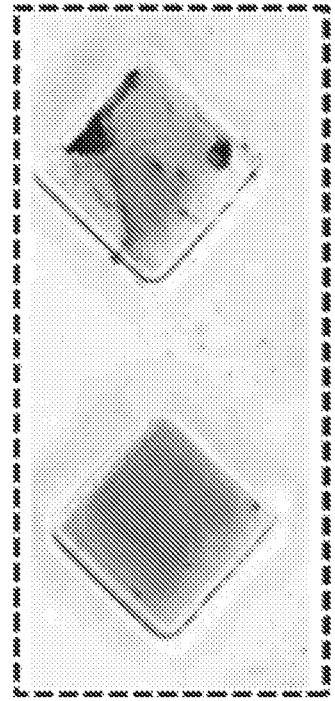
Figure 32A:
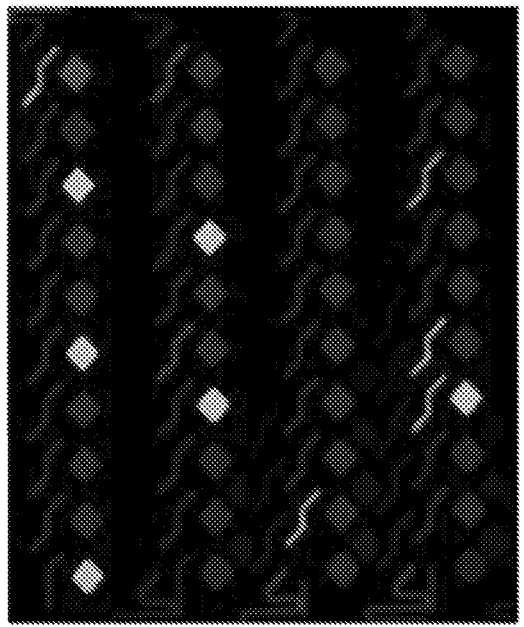

FIG. 32A-C provides data from two-step method described in Example 13. FIG. 32A provides a fluorescent digital pattern of a SlipChip device with LAMP amplification of phage lambda DNA in the presence of Toluidine 0-based amplification indicator. The image was taken before slipping. FIG. 32B is a bright field digital image of the same area acquired with stereoscope after slipping. FIG. 32C is callout from the bright field image.

The figures depict various embodiments of the present invention for purposes of illustration only. One skilled in the art will readily recognize from the following discussion that alternative embodiments of the structures and methods illustrated herein may be employed without departing from the principles of the invention described herein.

6. DETAILED DESCRIPTION

6.1 Interpretation of Terms

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereocenters intends each stereoisomer, and all combinations of stereoisomers, thereof.

Unless defined otherwise, all technical and scientific terms used herein have the same meaning as is commonly understood by one of skill in the art to which the claimed subject matter belongs. All patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, the singular forms "a," "an" and "the" include plural referents unless the context clearly dictates otherwise. In this application, the use of the singular includes the plural unless specifically stated otherwise. As used herein, the use of "or" means "and/or" unless stated otherwise. Furthermore, use of the term "including" as well as other forms (e.g., "include," "includes" and "included") is not limiting.

As used herein, ranges and amounts can be expressed as "about" a particular value or range. About also includes the exact amount. Hence "about 10 degrees" means "about 10 degrees" and also "10 degrees." Generally, the term "about" can include an amount that would be expected to be within experimental error.

6.2 Overview

The present invention provides a method of detecting and counting single or small numbers of nucleic acid molecules confined in nanoliter volumes in microfluidic devices using an unmodified cell phone camera, in combination with isothermal amplification chemistry, a judiciously chosen indicator dye and ratiometric image processing (outlined in FIG. 1). This provides a novel methodology that enables a visual readout for digital single-molecule amplification of sequence-specific RNA and DNA with any camera phone—without modifications or attachments. Single-molecule visual readout has never been achieved before with an unmodified cell phone camera. Diagnostic tests that incorporate such a visual readout will greatly expand the applicability of emerging digital single-molecule technologies, including into limited resource settings (LRS).

Specifically, the present invention provides a novel visual readout system for digital single-molecule amplification of RNA and DNA by: (i) selecting colorimetric amplification-indicator dyes that are compatible with the spectral sensitivity of standard mobile phones, and (ii) identifying an optimal ratiometric image-process for a selected dye to achieve a readout that is robust to lighting conditions and camera hardware and provides unambiguous quantitative results—even for colorblind users (FIG. 1). The amplification indicators were tested both for one-step or two-step visual detection of single nucleic acid molecules.

After sequence-specific single-molecule isothermal amplification, a visual readout can be captured by an unmodified camera phone and the resulting image can be analyzed using a ratiometric approach, wherein the measured intensities of two of the three RGB color channels are divided to provide a binary result (a positive or negative reaction) for each well. The automation of this ratiometric analysis provides a clear, reliable digital readout without requiring the user to differentiate color change by eye or manipulate lighting (FIG. 2A). Light spectral properties (absorption/transmission/reflection) can be used to detect and/or characterize nucleic acid amplification reactions containing amplification indicators.

This invention further shows how limitations related to reaction inhibition by the readout dye can be solved with microfluidics technology, such as a SlipChip, to decouple the amplification and readout steps. The microfluidic approach can also expand dynamic range and improve reaction performance, allowing ultrasensitive, quantitative measurements at volumes as low as 5 nL. This methodology was also validated using SlipChip-based digital single-molecule isothermal amplification with lambda DNA as a model and hepatitis C viral RNA as a clinically relevant target, in reaction volumes as low as 5 nL, using a variety of common cell phones and a range of illumination conditions.

The innovative combination of isothermal amplification chemistry in the presence of a judiciously chosen indicator dye and ratiometric image processing with SlipChip technology allowed the sequence-specific visual readout of single nucleic acid molecules in nanoliter volumes with an unmodified cell phone camera. When paired with devices that integrate sample preparation and nucleic acid amplification, this hardware-agnostic approach increases the affordability and the distribution of quantitative diagnostic and environmental tests.

In some cases, an amplification indicator can provide an effective and simple assay for detecting nucleic acids. In some cases, the method can provide high sensitivity, including single molecule sensitivity. In some cases, methods can be used for visualization of single nucleic acid molecule with unmodified cameras such as cell phone camera.

In some cases, absorption/transmission/reflection properties of an amplification reaction can be used to describe the content of the sample. In some embodiments, the absorption/transmission/reflection properties show presence or absence of specific nucleic acid targets.

In some cases, the methods described herein can be used to improve the detection of nucleic acid amplification reactions. In some cases, the methods described herein can be used to distinguish between positive and negative samples in visible light. Approaches, devices and methods disclosed herein can be used for detection, quantification, or identification of one or more nucleic acids.

Methods disclosed herein can comprise homogeneous reactions. Methods disclosed herein can comprise one-step reactions or one-pot reactions. Methods disclosed herein can comprise two-step reactions or two-pot reaction. Methods disclosed herein can decouple nucleic acid amplification and readout steps in a close-environment. Methods disclosed herein can provide a direct visualization of amplified nucleic acids.

6.3 Nucleic Acid Amplification

The terms "nucleic acid" and "nucleic acid molecule" as used interchangeably herein, refer to a molecule comprised of nucleotides, i.e., ribonucleotides, deoxyribonucleotides, or both. The term includes monomers and polymers of ribonucleotides and deoxyribonucleotides, with the ribonucleotide and/or deoxyribonucleotides being connected together, in the case of the polymers, via 5' to 3' linkages. However, linkages may include any of the linkages known in the nucleic acid synthesis art including, for example, nucleic acids comprising 5' to 2' linkages. The nucleotides used in the nucleic acid molecule may be naturally occurring or may be synthetically produced analogues that are capable of forming base-pair relationships with naturally occurring base pairs. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, and the like.

The amplification indicators can be used with various nucleic acid amplification methods.

The nucleic acid amplification method can comprise polymerase chain reaction (PCR), reverse transcription PCR (RT-PCR), quantitative PCR (qPCR), reverse transcription qPCR (RT-qPCR), nested PCR, multiplex PCR, asymmetric PCR, touchdown PCR, random primer PCR, hemi-nested PCR, polymerase cycling assembly (PCA), colony PCR, ligase chain reaction (LCR), digital PCR, methylation specific-PCR (MSP), co-amplification at lower denaturation temperature-PCR (COLD-PCR), allele-specific PCR, intersequence-specific PCR (ISS-PCR), whole genome amplification (WGA), inverse PCR, thermal asymmetric interlaced PCR (TAIL-PCR).

In some embodiments, the nucleic acid amplification reaction can be a nucleic acid isothermal amplification method. Isothermal amplification is a form of nucleic acid amplification which does not rely on the thermal denaturation of the target nucleic acid during the amplification reaction and hence may not require multiple rapid changes in temperature. Isothermal nucleic acid amplification methods can therefore be carried out inside or outside of a laboratory environment. A number of isothermal nucleic acid amplification methods have been developed, including but not limited to Strand Displacement Amplification (SDA), Transcription Mediated Amplification (TMA), Nucleic Acid Sequence Based Amplification (NASBA), Recombinase Polymerase Amplification (RPA), Rolling Circle Amplification (RCA), Ramification Amplification (RAM), Helicase-Dependent Isothermal DNA Amplification (HDA), Circular Helicase-Dependent Amplification (cHDA), Loop-Mediated Isothermal Amplification (LAMP), Single Primer Isothermal Amplification (SPIA), Signal Mediated Amplification of RNA Technology (SMART), Self-Sustained Sequence Replication (3 SR), Genome Exponential Amplification Reaction (GEAR) and Isothermal Multiple Displacement Amplification (IMDA). Further examples of such amplification chemistries are described in, for example, ("Isothermal nucleic acid amplification technologies for point-of-care diagnostics: a critical review, Pascal Craw and Wamadeva Balachandrana Lab Chip, 2012, 12, 2469-2486, DOI: 10.1039/C2LC40100B,") incorporated here in its entirety by reference.

6.4 Amplification Indicators

In some embodiments, an amplification indicator refers to a substance, e.g., a compound, that changes colorimetric properties in the presence of amplified nucleic acid or in the presence of byproducts of nucleic acid amplification.

In some embodiments, an amplification indicator changes colors upon the amplification of a nucleic acid. In some cases, a portion of the reaction medium can change colorimetric properties that are sensed by the image sensor. The change of colorimetric properties can be when a portion of the sample changes color in the presence of a specific or non-specific nucleic acid sequence. A change in colorimetric properties can be a change in proportions of multiple colors. A change in colorimetric properties can be a change in intensity of a color. In some embodiments, a colorimetric signal can be detected when a portion of the reaction medium changes from clear to colored.

In some embodiments, a colorimetric signal can be detected when a portion of the reaction medium changes from one color to another. A color can be red, blue, green, purple, yellow, orange, indigo, violet, etc. A color of an object can be the set of wavelengths of visible light that are absorbed, reflected, and emitted by the object, for example. Additionally, colorimetric signal can be the change of intensity of a color. A colorimetric signal can be detected when a portion of the reaction medium changes from transparent to opaque or from opaque to transparent in the presence of a nucleic acid amplification, for example.

In some embodiments, an amplification indicator has an extinction coefficient larger than 5,000 L mol-1 cm-1 at a wavelength between 400 and 700 nm or between 400 and 1400 nm. In some embodiments, an amplification indicator has extinction coefficient larger than 10,000 L mol-1 cm-1, 20,000 L mol-1 cm-1, 25,000 L mol-1 cm-1, 50,000 L mol-1 cm-1, 100,000 L mol-1 cm-1 or 1000,000 L mol-1 cm-1 at a wavelength between 400 and 700 nm or between 400 and 1400 nm.

In some embodiments, an amplification indicator substance is not a fluorescent dye.

In some embodiments, an amplification indicator can be an organic or inorganic compound that is added to a nucleic acid amplification reaction mix so the content of the solution (such us for example presence or absence of specific nucleic acids) can be determined visually.

In some embodiments, an amplification indicator changes light absorbance, light reflection, or light transmission at wavelengths between 400 and 700 nm or between 400 and 1400 nm responsive to nucleic acid amplification. In some embodiments, the amplification indicator changes its extinction coefficient more than 3%, more than 5%, more than 10%, more than 20%, more than 30%, or more than 40% at a wavelength between 400 and 700 nm or between 400 and 1400 nm responsive to nucleic acid amplification.

In some embodiments, the amplification indicator can be a metal ion indicator (also called complexometric indicator or metallochromic indicator). A substance that changes color after forming a metal ion complex with a color different from that of the uncomplexed indicator. Examples of such metal ions include, but are not limited to, $Ca^{2+}$, $Mg^{2+}$, $Zn^{2+}$ and other metal ions.

Metal ion amplification indicators suitable to use in the present methods include, but are not limited to, hydroxynaphthol blue, eriochrome black t, calmagite, curcumin, fast sulphon black, hematoxylin, murexide, xylenon orange, BAPTA, BAPTA AM, BTC, BTC AM, Calcein, Calcein AM, Calcein Blue, Calcium Green 1, Calcium Green 2, Calcium Green 5N, Coelenterazine, Coelenterazine cp, Coelenterazine f, Coelenterazine h, Coelenterazine hcp, Coelenterazine n, CoroNa Green, Corona Green AM, CoroNa Red, DAF FM, Fluo 3, Fluo 3 AM, PBFI AM, Phen Green SK, Quin 2, Quin 2 AM, RhodZin 3.

In some embodiments, the amplification indicator can be a pH indicator. A pH indicator is a chemical detector for hydronium ions (H3O+) or hydrogen ions (H+). Normally, the indicator causes the color of the solution to change depending on the pH. Indicators can also show change in other physical properties; for example, olfactory indicators show change in their odor.

Suitable pH indicators include, but are not limited to: gentian violet, malachite green, thymol blue, methyl yellow, bromophenol blue, congo red, methyl orange, screened methyl orange (first transition), screened methyl orange (second transition), Bromocresol green, methyl red, methyl Purple, azolitmin red, bromocresol purple, bromothymol blue, phenol red, neutral red, naphtholphthalein, Cresol red, Cresolphthalein, Phenolphthalein, Thymolphthalein, Alizarine Yellow R yellow, Indigo carmine.

In some embodiment, the amplification indicator can be a redox indicator (also called an oxidation-reduction indicator). Indicator dyes that undergo a definite color change at a specific electrode potential. There are two common type of redox indicator: pH independent redox indicator and pH dependent redox.

Exemplary pH independent redox indicators include, but are not limited to, 2,2'-bipyridine, Nitrophenanthroline, N-Phenylanthranilic acid, 1,10-Phenanthroline iron(II) sulfate complex, N-Ethoxychrysoidine, 2,2'-Bipyridine, 5,6-Dimethylphenanthroline, o-Dianisidine, Sodium diphenylamine sulfonate, Diphenylbenzidine, Diphenylamine, Viologen.

Examples of pH dependent redox indicators include, but are not limited to, Sodium 2,6-Dibromophenol-indophenol, Sodium o-Cresol indophenol, Thionine, Methylene blue, Indigotetrasulfonic acid, Indigotrisulfonic acid, Indigo carmine, Indigomono sulfonic acid, Phenosafranin, Safranin, Neutral red.

6.5 Unmodified Cameras

In some embodiments, color images or unprocessed images can be obtained by an unmodified camera. In some embodiments, the unmodified camera is a commercially available cell phone camera. For example, the device can be an iPhone, Apple iPhone 4S, HTC inspire 4G, Motorola Moto G or Nokia 808 PureView. In certain implementations, the unmodified camera can capture images at wavelengths not typically perceptible by the human eye. In some embodiments, the unmodified camera can capture images at wavelengths ranging from 400 to 1400 nm, 400 to 1100 nm, 400 to 900 nm, 400 to 700 nm, 500 to 700 nm or 550 to 650 nm.

The digital camera can have an image sensor made up of a plurality of pixels. For instance, the camera can have an image sensor with more than 1, 2, 3, 4, 5, 6, 7, 8, 10, 12, 14, 16, 18, 20, 22, 26, 30, 34, 38, 40, 44, 48, 52, 56, 60, 70, 80, 90, or 100 megapixels, for example. For instance, the camera can produce an image with more than 1, 2, 3, 4, 5, 6, 7, 8, 10, 12, 14, 16, 18, 20, 22, 26, 30, 34, 38, 40, 44, 48, 52, 56, 60, 70, 80, 90, or 100 megapixels, for example. In some embodiments, the camera can have an image sensor from about 6 megapixels to about 20 megapixels. In some embodiments, the camera can use a 41-megapixel sensor. The camera can use a 41-megapixel sensor with a pixel size of 1.4 µm.

In some embodiments the sensor is capable of being moved relative to sample. The image sensor may correct for movement of using software.

In some embodiments, the camera is a video camera. A video camera captures a plurality of images over time. In some embodiments, the video camera captures a plurality of images over time, and a subset of images are determined to be useful for further analysis. In some embodiments, a video camera captures a plurality of images, and a single image is selected for further analysis. The selection can be made by the user. The selection can be automated. The automated selection can be done by analysis of the contents of the image.

The image sensor can comprise one more lenses. The lens can be a lens typically found on a consumer digital camera or cell phone camera. For example, a Carl Zeiss F2.4 8.02 mm lens. In some instances, a second lens can be used.

The focal distances of a lens associated with an image sensor can be less than 100 cm, less than 90 cm, less than 80 cm, less than 70 cm, less than 60 cm, less than 50 cm, less than 40 cm, less than 30 cm, less than 20 cm, less than 10 cm, less than 5 cm, or less than 1 cm. For example a 0.67× magnetically mounted wide lens can be used. Using this objective images can be obtained, which auto-focus on the sample, at distances of 6.5 cm.

An image sensor can have an offset between a light source and a detector.

For example, the image sensor can be the Nokia 808 PureView's 1/1.4" CMOS sensor with a 41 MP resolution, outputting a maximum of 38 MP (at 4:3 aspect ratio); pixel size is 1.4 µm.

The image sensor can be a consumer digital camera or phone, for example a Nokia Pureview 808 cell phone. The image sensor can be a consumer digital portable computer or tablet. The image sensor can be a video camera. The image sensor can be included in a device such as a wristwatch. The image sensor can be an iPhone, Samsung Galaxy, or GoPro, for example.

Oversampling: for example, images captured in the PureView modes are created by oversampling from the sensor's full resolution. Pixel oversampling bins many pixels to create a much larger effective pixel, thus increasing the total sensitivity of the pixel.

6.6 Image Processing

In some embodiments, image processing can be used to process an image so that the result is more suitable than the original image for a specific application. For example, the color change between positive and negative amplification reactions containing an amplification indicator can be enhanced by image processing.

In some embodiments, image processing can use mathematical operations by using any form of signal processing for which the input is an image, such as a photograph or video frame, and the output may be either an image or a set of characteristics or parameters related to the image.

In some embodiments the image processing can produce an image of higher contrast than the original by darkening a particular level.

In some embodiments, the image processing can correct background signals.

In some embodiments, the image processing can adjust white balance.

In some embodiments, commercial software designed for image processing is used.

In some embodiments, an image processing strategy can be used to improve the detection and reduce risk of false positive or false negative due to similar colors (such as for example purple and blue).

In some embodiments, pictures taken in the conventional color schemes (e.g. in RGB or CYMK color schemes) can be transformed to the L-A-B color scheme. This can be done by using a dedicated script (e.g. in image J), using software for image processing or other strategies. When transformed to L-A-B color scheme, in the "A" channel the blue that indicates positive amplification, when using eriochrome T as the amplification indicator, shows a negative signal (dark) while the purple indicating the negative amplification shows a positive signal (clear). Other amplification indicators may have different effects on the A and B channels in the L-A-B color scheme. This image processing enhances the contrast between the positive and negative signals, and allow for easy and automated detection of the results obtained with amplification.

In some embodiments, pictures taken in in the conventional color schemes (e.g. in RGB or CYMK color schemes can be processed to improve the detection. In some embodiments, the image can be split into the color channels (e.g., Red, Green, Blue) and image processing can be used with these channels. As an example, the green value for each pixel can be divided by the red value, and the image obtained can show an improved signal for processing and automated analysis.

In some embodiments, images are analyzed to identify one or more pixels corresponding to each of a plurality of compartments. For example, if devices have been etched with four 4 mm-diameter circles, these 4 circles can be used to identify such pixels. The circles are sorted in a way that the software can understand, if necessary, any tilt in the image can be corrected by rotating the image until the line between two dots are parallel to the image axis. After such a correction, the portion of the chip that contains the wells then can be determined based upon distances from the dots.

In some embodiments, background images of compartments can be used to identify one or more pixels corresponding to each of the plurality of compartments. In some embodiments, marks added next to each well can be used to identify such pixels.

In some embodiments the image processing can be used to perform a ratiometric analysis. In some embodiments, the image processing can update raw images to produce updated images, which can be used for ratiometric analysis. In some embodiments, ratiometric image analysis methods comprise a preceding step of updating a raw image to make it more appropriate for ratiometric image analysis.

In some embodiments the image processing can be used to detect single molecule amplification reactions containing amplification indicators.

In some embodiments the image processing can be used to enhance differences between positive and negative amplification reactions containing amplification indicators.

In some embodiments, the image processing is done on a separate device, such as a server computer. In some embodiments, the image processing could be done on an image obtained by email, SMS messaging, web posting, phone call, electronic messaging, uploading or downloading.

In some embodiments, the image processing can take less than 5 min, 4 min, 3 min, 2 min, 1 min, 50 sec, 45 sec, 40 sec, 30 sec, 20 sec, 10 sec, 9 sec, 8 sec, 7 sec, 6 sec, 5 sec, 4 sec, 3 sec, 2 sec, 1 sec, 0.5 sec, 0.4 sec, 0.3 sec, 0.2 sec, or 0.1 sec, for example. In some embodiments, the analysis process takes less than 1 min.

6.7 Ratiometric Approach

The ratiometric approach described herein can be used with any color scheme (e.g., additive schemes such as for example RGB or subtractive color schemes such as for example CMYK). In some embodiments, color schemes (e.g., CMYK and RGB) are used singly; in some embodiments, color schemes are used in combination.

In some embodiments, more than one ratio can be included to increase the confidence of the positive/negative distinction in the binary colorimetric readout, such as for example, G/R, GB and RB in an RGB scheme. Ratios may not have the same ranges between values corresponding to positive and negative. So in some embodiments, if more than one ratio is used, the ratios may be weighed accordingly. In an example with EBT dye, for example, we predicted values based on a linear contribution; for other dyes or conditions, other ways of scoring the measured value on the positive-negative range spectrum (e.g., quadratic or exponential) may be more appropriate. Based on the predicted values, such as those shown in FIG. 3B and Table 1, experimental transmittance data can be analyzed using more than just one ratio to calculate a positive or a negative result with greater confidence.

TABLE 1

Predicted data (FIGS. 3B-D).
Predicted data

|   | blue(+) | purple(−) |
|---|---------|-----------|
| R | 185     | 219       |
| G | 197     | 190       |
| B | 209     | 212       |

Using again EBT as one example, the data for a positive and a negative collected with a cell phone camera (Table 3) is first converted into ratio form. The predicted values are given in FIG. 3B and FIG. 3D and are summarized in Table 1. Then, each experimental ratio is compared to the corresponding predicted one (Table 2) to determine how close it is to the positive or negative values. This is done by taking the difference between the experimental value and the minimum predicted value of the given ratio and scaling it by the predicted ratio range:

$$\text{Contribution of ratio} = \frac{\text{measured ration} - \text{min. value of ratio (predicted)}}{\text{ratio range (predicted)}}$$

for example:

$$\frac{R}{G}\text{ Contribution} = \frac{1.03 - 0.87}{0.20} = 0.80$$

Next, the contributions from two or more ratios are combined, with the option of giving each ratio an appropriate weight. For example, weights may be based on the ranges of the predicted values (Table 2):

Determination confidence $$= \text{weight}_{R/G}*\text{contribution}_{R/G} + \text{weight}_{B/R}*\text{contribution}_{B/R} + \text{weight}_{G/B}*\text{contribution}_{G/B}$$

for example:

Positive determination confidence =
$$\frac{0.20}{0.41}*0.80 + \frac{0.16}{0.41}*0.60\frac{0.05}{0.41}*1.44 = 0.80$$

Positive determination confidence =
$$\frac{0.20}{0.41}*0.21 + \frac{0.16}{0.41}*0.07\frac{0.05}{0.41}*0.69 = 0.21$$

For values close to unity, the data support the measurement being a positive. For values close to zero, data support the measurement being a negative. A ratiometric value greater than 0.5, indicates a positive measurement. A ratiometric value less than 0.5, indicates a negative measurement. The largest uncertainty in measurement lies around 0.5 value.

TABLE 2

Predicted data put into ratio form. Ranges of ratios and their sum computed.

|  | blue(+) | purple(−) | Range |
|---|---|---|---|
| R/G | 1.06 | 0.87 | 0.20 |
| B/R | 1.13 | 0.97 | 0.16 |
| G/B | 0.94 | 0.90 | 0.05 |
|  |  | total: | 0.41 |

TABLE 3

Example with data collected with cellphone.

|  | blue(+) | purple(−) |
|---|---|---|
| Predicted data | | |
| R | 152 | 142 |
| G | 156 | 129 |
| B | 162 | 139 |
| Make into ratio form: | | |
| R/G | 1.03 | 0.91 |
| B/R | 1.07 | 0.98 |
| G/B | 0.96 | 0.93 |
| Calculate contributions based on predicted ranges: | | |
| R/G contribution | 0.80 | 0.21 |
| B/R contribution | 0.60 | 0.07 |
| G/B contribution | 1.44 | 0.69 |
| Using appropriate weights, compute confidence: | | |
| +/− determination confidence | 0.80 | 0.21 |

In some embodiments, e.g., for certain dyes or reaction conditions, the ratios corresponding to positive and negative values may be inverted from the EBT examples provided (e.g., a lower ratio value may not always correspond to positive). Care should be taken to incorporate this into the analysis.

6.8 Robustness

Robustness can be the degree to which a series of repeated quantitative measurements provides a set of similar measurements under varying experimental conditions. For example, a cell phone camera may be used to successfully perform similar measurements on a SlipChip under a variety of conditions found in the real world. Similar measurements can be identical measurements. Similar measurements can be the same diagnosis. Similar measurements can be the same answer. Similar measurements can mean more than one measurement within experimental error of each other. Similar measurements can yield a consistent outcome with statistical significance. Similar measurements can be of similar numerical size, for instance within 5%, 10%, 15%, 20%, 25%, 30%, 40%, 50%, 60%, 70%, 80%, 90%, 100%, 200%, 1,000% of each other. Robust assays can produce similar measurements more often than 25%, 30%, 40%, 50%, 60%, 70%, 80%, 85%, 90%, 95%, 96%, 97%, 98%, 99%, 99.5%, 99.9%, 99.99%, for example, of instances measured under a given set of conditions.

Different types of assays can be robust assays. A nucleic acid amplification and quantification assay can be robust. A LAMP assay can be robust. A RT-LAMP assay can be robust. A dRT-LAMP assay can be robust. A binary LAMP reaction can be robust. A binary, two-step LAMP reaction can be robust. A PCR reaction can be robust. A qPCR assay can be robust. A quantitative nucleic acid amplification reaction can be robust. A qualitative nucleic acid amplification reaction can be robust. A method to diagnosis a health outcome based on the amplification of a nucleic acid sequence can be robust. A process within a SlipChip can be robust. The imaging and analysis of a SlipChip after a LAMP reaction can be a robust process.

The absolute efficiency of dRT-LAMP can be increased over 10-fold, e.g., from ~2% to ~28%, by i) using a more efficient reverse transcriptase, ii) introducing RNase H to break up the DNA-RNA hybrid, and iii) adding only the BIP primer during the RT step. dRT-LAMP can be compatable with a plastic SlipChip device and used this two-step method to quantify HIV RNA. The dRT-LAMP quantification results were in some cases very sensitive to the sequence of the patient's HIV RNA.

Assays can be robust with respect to experimental variables. An assay can be robust with respect to a given temperature range. An assay can be robust of over a temperature range. Some non-limiting ranges, over which an assay can be robust include 1° C., 2° C., 3° C., 4° C., 5° C., 6° C., 7° C., 8° C., 9° C., 10° C., 11° C., 12° C., 16° C., 20° C., 24° C., 28° C., 32° C., 40° C., 50° C., 60° C., 80° C., 100° C., 150° C. 200° C., 250° C., or 300° C., for example. The temperature range of which an assay is robust can be centered on temperature on an absolute temperature scale. Some non-limiting temperatures that could be the center of the temperature range that an assay is robust to include −40° C., −30° C., −10° C., 0° C., 10° C., 20° C., room temperature, 25° C., 30° C., 35° C., body temperature 37° C., 40° C., 45° C. 50° C., 55° C., 60° C., 65° C., 70° C., 80° C., 90° C., 100° C., 110° C., 150° C., or 200° C., for example. In some embodiments, a binary LAMP assay is used to amplify and subsequently image and quantify a nucleic acid sequence in a sample. In these embodiments, the assay can be a robust quantification of a nucleic acid sequence with over a temperature range of 9° C. centered at about 60° C. A binary LAMP assay used to amplify and subsequently image and quantify a nucleic acid sequence in a sample can be robust over the temperature range from about 55° C. to about 66° C. In some embodiments, a SlipChip can be imaged and the data can be processed to give robust findings over a range of a temperature from about 5° C. to about 70° C.

An assay can be robust with respect to time. An assay can give consistent results over a range of time points. An assay can require only end-point readout. A binary DNA amplification experiment can require only end-point readout. The endpoint read out can be obtained near the completion of amplification, or at a time after this time point. A robust DNA amplification assay can give consistent results at a time point near the end of the reaction and/or at a timepoint after the reaction is complete. A non-limiting range of reaction time that an assay could be robust over includes 0.01 min, 0.1 min, 0.5 min, 1 min, 2 min, 3 min, 4 min, 5 min, 6 min, 7 min, 8 min, 9 min, 10 min, 12 min, 14 min, 16 min, 20 min, 24 min, 28 min, 32 min, 40 min, 45 min, 50 min, 1.0 hour, 2 hours, 3 hours, 4 hours, 5 hours, 6 hours, 8 hours, 10 hours, 12 hours, 16 hours, 18 hours, 1 day, 2 days, 3 days, 7 days, 1 month, or 1 year, for example. In some cases, binary DNA amplification experiments do not require exact knowledge of time. The output of a binary DNA amplification can be robust to variation in reaction time beyond the optimal reaction time. In some embodiments, a d-LAMP assay on a SlipChip is robust over a 20-minute time period between 40 minutes and 60 minutes after the LAMP reaction begins, for example.

An assay can be robust with respect to variations in atmospheric humidity. In some embodiments, an assay can be robust regardless of the atmospheric humidity. In some embodiments, an assay can be robust over a range of atmospheric humidity. The range of humidity can be from about 0% to 100% relative humidity. The range of atmospheric humidity at which an assay can be robust can be from about 0 to about 40 grams water per cubic meter of air at about 30° C. In some embodiments, an assay can be robust from about 0% humidity to about 40%, 50%, 60%, 70%, 80%, 90%, or 100% humidity, for example. In some embodiments, an assay can be robust over a humidity range of about 40%, 50%, 60%, 70%, 80%, 90%, or 100% humidity. In some embodiments, a d-LAMP assay run in a SlipChip can be imaged and analyzed as a robust assay over a range of humidity from about 0% to about 100% atmospheric humidity.

An assay can be robust with respect to equipment used to perform the experiment. For example, an assay can be robust with respect to the type of camera used. An assay can be robust with respect to the number of pixels in the image recorded by the camera. An assay can be robust with respect to the software system running on the device that captures the data. An assay can be robust with respect to the sample container. An assay can be robust with respect to using a cellphone with a built in camera versus using specialized equipment. An assay can be robust with respect to the type of camera flash present on the camera device used. An assay can be robust with respect to having imaging performed with non-quantitative consumer electronic devices such as cell phones, tablets, or small handheld computers. An assay can be robust with respect to an external excitation light source.

An assay can be robust with respect to camera flash inconsistency. An assay can be robust with respect to mechanism of flash. For example, an assay could yield robust and consistent result with a Xenon flash or an LED flash. An assay can be robust with respect to flash size. An assay can be robust with respect to flash direction. An assay can be robust with respect to the flash direction. In some embodiments, the direction the flash is pointed can yield consistent results. In some embodiments, the timing of the flash can be inconsistent, and the assay can be robust over a range of potential flash timings.

An assay can be robust with respect to external light source inconsistency. An assay can be robust with respect to the orientation of an external light source. An assay can be robust with respect to the type of light source used to generate the signal, such as, for example, light emitting diodes, compact fluorescent lights, incandescent lights, xenon flashes, etc. An assay can be robust with respect to the external light source intensity. An assay can be robust with respect to the color of an external light source.

An assay can be robust with respect to variations in the amount of background light present during imaging. In some embodiments, whether conducted in a dark room or in the presence of background light, an assay can give consistent results. In some embodiments, a d-LAMP assay can be robust over a range of background lighting. Some non-limiting examples of ranges of background lighting that an assay can be robust over can be from about 0 lux, 0.1, 0.2, 0.5, 0.8, 1.0 to about 1, 2, 3, 4, 5, 6, 7, 8, 9, 10, 12, 14, 16, 20, 24, 28, 32, 36, 40, 50, 60, 70, 80, 90, 100, 200, 300, 400, 500, 600, 700, 800, 900, or 1000 lux, for example. An assay can be robust with respect to ambient daylight. In some embodiments, an assay can be robust whether in a dark room, or carried out with a cell phone placed in a shoe box.

In some embodiments, the assay provides a quantitative analytical measurement. For instance, the invention can measure and display the amount and/or the concentration of a nucleic acid sequence within a sample as a quantitative amount. This measurement can be robust with respect to the experimental conditions present during the chemical amplification of the nucleic acid sequence, during the measurement of the optical data, and/or during the processing of the data, for instance. Examples of experimental perturbations or varying experimental conditions include, but are not limited to, for example variation of temperature of several degrees Celsius, variations in atmospheric humidity, imaging performed with non-quantitative consumer electronic devices such as cell phones, variations in assay time, camera flash inconsistency, sampling errors, variations in the amount of background light present during imagining. In some embodiments, a binary LAMP assay is used to amplify and subsequently image and quantify a nucleic acid sequence in a sample. In these embodiments, an accurate and reproducible quantification of the sequence can be obtained with a variation of temperature from about 55° C. to about 66° C., over a time period of 15 min-1.5 hours, in the presence of 0-100% atmospheric humidity, when the measurement is obtained with a cell phone camera that is not confined to a dark room. An assay can be robust with respect to variation of multiple experimental variables within a single experiment. For example, a binary LAMP assay taking place in a SlipChip can be robust and yield consistent results over a range of reaction temperature, reaction time, and amount background light presence during imaging for a given sample. For example, a binary LAMP assay taking place in a SlipChip can be robust and yield similar results when data is obtained from imaging with a cellphone in a shoebox, with reaction time varying from 40 min, 50 min to 60 min, over a six-degree temperature range (temperature range 55-66° C.).

6.9 Light Properties

In some embodiments, absorbed, reflected and/or transmitted light through a nucleic acid amplification reaction containing an amplification indicator can be used to distinguish positive and negative samples.

In some embodiments, detection of amplification can be identified by comparing a change in spectral properties of the amplification solution containing the amplification indicator before and after amplification.

In some embodiments, absorbed, reflected and/or transmitted light through a nucleic acid amplification reaction containing an amplification indicator can be used to understand the suitability of different unmodified cameras (such as for example but not limited, CMOS based cell phone camera, a camera designed for general purposes, retail cameras without additional filters, lenses, lightening sources, etc.) for distinguishing differences between positive and negative samples.

In some embodiments, amplification reactions containing an amplification indicator, such as for example a metal ion indicator, can be analyzed by analytical techniques such as for example measuring absorbance or transmittance at specific wavelengths and or by spectrophotometry.

In some embodiments, absorbance and or transmittance spectrum can be used to generate ratiometric measurements. For example, the intensities of two of the three RGB color channels can be divided to provide a ratiometric measurement.

In some embodiments, nucleic acid amplification can be detected by the ratio of absorbance at different wavelengths. As an example, the amplification can be detected by a variation in the absorbance ratio at two wavelengths (for example, the ratio of absorbance at 540 and 650 nm can be used to detect differentiate positive and negative amplification reactions).

6.10 Binary Quantification

The process of binary quantification begins with a sample that may contain an analyte. The analyte can be a molecule to be quantified or searched for, for instance a particular nucleic acid, a particular nucleic acid sequence, a gene, or a protein, for example. The sample can be partitioned into many separate reaction volumes. In some embodiments, the reaction volumes are separate analysis regions. In some embodiments, the separate reaction volumes are physically separated in separate wells, chambers, areas on the surface of a slide, droplets, beads, or aliquots, for example. In some embodiments, the separate reaction volumes can be in the same container, for instance, the analyte can be affixed to a substrate or attached to a bead. Such reaction volumes can be on beads, on the surface of a slide, or attached to a substrate. The sample is distributed to many separate reaction volumes such that each individual reaction volume contains either zero individual molecules of the analyte, or one or more individual molecules of the analyte. One or more molecules can mean a non-zero number of molecules. One or more molecules can mean one molecule. In some embodiments, one or more molecules can mean one molecule, two molecules, three molecules, four molecules . . . etc. In some embodiments, each separate reaction volume is contained in a well. In some embodiments, the sample is distributed such that each reaction volume, on average comprises less than one individual molecule of the analyte. In some embodiments, the sample is distributed such that most reaction volumes comprise either zero or one molecules of the analyte.

Next, a qualitative "yes or no" test can be done to determine whether or not each reaction volume contains one or more analyte molecules by reading the pattern of discrete positive and negative reaction volumes. A positive reaction volume can be a reaction volume determined to contain one or more analyte molecules. A positive reaction volume can be a reaction volume determined to have a signal that correlates to the presence of one or more analyte molecules. A positive reaction volume can be a reaction volume determined to have a signal above a threshold that correlates to the presence of one or more analyte molecules. In some embodiments, a positive reaction volume is quantified as 1, or a simple multiple of 1 such as 2, 3, etc. while a negative reaction volume is quantified as 0. In some embodiments, a positive reaction volume is quantified as 1 and a negative reaction volume is quantified as 0. A negative reaction volume can be a reaction volume determined to contain zero analyte molecules. A negative reaction volume can be a reaction volume that does not have a signal that correlates to the presence of one or more analyte molecules. A negative reaction volume can be a reaction volume that does not have a signal above the threshold that correlates to the presence of one or more analyte molecules. The determination and/or designation of each reaction volume as a positive or a negative reaction volume can be referred to as a binary assay or a digital assay. This "yes or no test" or test like this can be referred to as a binary assay. This qualitative analysis of which reaction volume are negative reaction volume and which reaction volume are positive reaction volume can then be translated into a quantitative concentration of analyte in the sample using Poisson analysis.

A high dynamic range can be achieved through using many reaction volumes. A high dynamic range can be achieved by using a device that has reaction volume of different sizes. A high dynamic range can be achieved by partitioning the sample into many wells and/or into wells of different sizes. This overall process can be called binary quantification of nucleic acids. This process can be called counting molecules of analyte. In some embodiments, binary quantification is the process of partitioning a sample into a plurality of reaction volume such that each reaction volume contains either zero or a non-zero number of analyte molecules; determining and/or designating which reaction volume are positive reaction volume and which reaction volume are negative reaction volume with respect to the analyte molecule; and translating the information about positive and negative reaction volume into information about the quantity or concentration of the analyte molecule in the sample. In some embodiments, the absolute number of analyte molecules is determined. In some embodiments, the translation of the information about which reaction volume are positive reaction volume and which reaction volume are negative reaction volume to information about the amount, absolute number of molecules, or concentration of the analyte in the sample is called digital quantification of the analyte. In some embodiments, the analyte is a nucleic acid. In some embodiments, the binary quantification of nucleic acids is achieved. In some embodiments, binary quantification of a nucleic acid analyte is determined wherein the sample is partitioned into several reaction volumes, wherein the reaction volumes are on a SlipChip.

In some embodiments, a binary quantification of analyte molecules in a sample can be achieved without spatially separating the sample into multiple reaction volumes. In these embodiments, the analyte molecules can be counted by informational separation. In some embodiments, analyte molecules in the sample undergo a binary quantification through a process wherein the analyte molecules are tagged with a pool of information-carrying molecules, amplified or copied, and the number of distinct information-carrying molecules that were amplified or copied is counted in to get a quantification of the starting number of analyte molecules (see e.g., WO 2012148477). In some embodiments, the information-carrying molecule can be a pool of chemical barcodes. In some embodiments, the information-carrying molecule can be a set of nucleic acid sequences.

Digital analyses can be achieved using the polymerase chain reaction (PCR), recombinant polymerase amplification (RPA), and loop mediated amplification (LAMP) as a way of quantifying RNA or DNA concentrations. Amplifications such as RPA and LAMP, which can use isothermal chemistries, can be well suited for home and limited-resource setting use. LAMP chemistry in particular is an attractive candidate for use in a home or limited-resource setting platform as it can have a relatively broad temperature tolerance range, can work with simple and cheap chemical-based heaters and phase-change materials.

Described herein, in certain embodiments, are a device for and methods of analyzing color image patterns using a mobile communication device, and transmitting and processing information. Such capability is valuable for many purposes, including the analysis of digital nucleic acid amplification reactions.

6.11 Platforms

The assays, reactions, and techniques described herein can be performed on any suitable platform, including but not limited to tubes, capillary tubes, droplets, microfluidic devices (e.g., SlipChip devices), wells, well plates, microplates, microfluidic wells, microfluidic droplets, emulsions, solid supports (e.g., beads or microarrays), microchips, or gels (e.g., 2D gels, 3D gels) and reactions inside gels including "polonies" as in polony PCR on surfaces and in gels.

In some embodiments, microfluidics devices can be used for digital experiments (single molecule) and device wells might have small volume such as, for example but not limited, 500 nL to 1 microliter, 250 nL to 500 nL, 125 nL to 250 nL, 25 nL to 125 nL, 5 nL to 25 nL, 1 nL to 5 nL, 0.1 nL to 1 nL and ~10 to 1000 microns deep.

In some embodiments can be necessary to use amplification indicators that have a high extinction coefficient (such as for example eriochrome black T). For example, visualization of single molecule amplification reaction performed into wells with short path lengths.

Platforms can comprise fluid handling mechanisms enabling loading, unloading, mixing, and other handling of sample volumes, reagent volumes, and other fluids. For example, a microfluidic device can be used comprising channels for loading fluids into wells or droplets, for mixing contents of wells or droplets, or for off-loading of contents of wells or droplets.

Some platforms are useful for conducting assays in a digital or quasi-digital format, as described herein. For example, wells, well plates, microwells, microfluidic droplets, emulsions, beads, and microarrays can provide a useful platform for conducting a digital or quasi-digital assay. In such an assay, the compartments can comprise individual wells, droplets, beads, or microarray spots.

Platforms can be compatible with one or more readout or detection mechanisms. For example, a platform can be transparent or translucent in part or in total, allowing fluorescent measurement, detection of precipitate or gas bubble, or other visual observation. A platform can comprise visual detectors, such as CCDs, CMOS sensors, cameras, photon detectors, and other sensors. In another example, a platform can comprise electrical sensors, such as electrodes positioned within microwells. Platforms can be compatible with off-loading of samples for analysis. For example, a platform can permit unloading of droplets or contents of wells for mass spectrometry, sequencing, or electrophoresis.

6.11.1. SlipChip Device:

In some embodiments, the assays, reactions, and techniques described herein can be performed on SlipChip. A SlipChip is a device that can hold the sample. A SlipChip holding a sample can be imaged. In some embodiments, a SlipChip is composed of two parts having matched surfaces with complementary patterns.

In some embodiments, glass embodiments are made with standard photolithographic and wet chemical etching techniques. In some embodiments, SlipChip devices of the PDMS/Glass type are made using soft lithography.

in some embodiments, a SlipChip is made of polymeric materials. Polymeric materials suitable for use with the invention may be organic polymers. Such polymers may be homopolymers or copolymers, naturally occurring or synthetic, crosslinked or uncrosslinked. Specific polymers of interest include, but are not limited to, polyimides, polycarbonates, polyesters, polyamides, polyethers, polyurethanes, polyfluorocarbons, polystyrenes, poly(acrylonitrile-butadiene-styrene)(ABS), acrylate and acrylic acid polymers such as polymethyl methacrylate, and other substituted and unsubstituted polyolefins, and copolymers thereof. Generally, at least one of the substrate or a portion of the SlipChip device comprises a biofouling-resistant polymer when the microdevice is employed to transport biological fluids. Polyimide is of particular interest and has proven to be a highly desirable substrate material in a number of contexts. Polyimides are commercially available, e.g., under the tradename Kapton®, (DuPont, Wilmington, Del.) and. Upilex® (Ube Industries, Ltd., Japan). Polyetheretherketones (PEEK) also exhibit desirable biofouling resistant properties. Polymeric materials suitable for use with the invention include silicone polymers, such as polydimethylsiloxane, and epoxy polymers.

The SlipChip devices of the present invention can also be fabricated from a "composite," i.e., a composition comprised of unlike materials. The composite can be a block composite, e.g., an A-B-A block composite, an A-B-C block composite, or the like. Alternatively, the composite may be a heterogeneous combination of materials, i.e., in which the materials are distinct from separate phases, or a homogeneous combination of unlike materials. As used herein, the term "composite" is used to include a "laminate" composite. A "laminate" refers to a composite material formed from several different bonded layers of identical or different materials. Other preferred composite substrates include polymer laminates, polymer-metal laminates, e.g., polymer coated with copper, a ceramic-in-metal or a polymer-in-metal composite. One preferred composite material is a polyimide laminate formed from a first layer of polyimide such as Kapton®, that has been co-extruded with a second, thin layer of a thermal adhesive form of polyimide known as KJ®, also available from DuPont (Wilmington, Del.).

In some embodiments, the device can be fabricated using techniques such as compression molding, injection molding or vacuum molding, alone or in combination. Sufficiently hydrophobic material can be directly utilized after molding. Hydrophilic material can also be utilized, but may require additional surface modification. Further, the device can also be directly milled using CNC machining from a variety of materials, including, but not limited to, plastics, metals, and glass. Microfabrication techniques can be employed to produce the device with sub-micrometer feature sizes. These include, but are not limited to, deep reactive ion etching of silicon, KOH etching of silicon, and etching of glass. Polydimethylsiloxane devices can also be fabricated using a machined, negative image stamp. In addition to rigid substrates, flexible, stretchable, compressible and other types of substrates that may change shape or dimensions can be used as materials for certain embodiments of the SlipChip. In certain embodiments, these properties may be used to, for example, control or induce slipping.

In some instances, the base, plate and substrate of the SlipChip device can be made from the same material. Alternatively, different materials can be employed. For example, in some embodiments the base and plate can be comprised of a ceramic material and the substrate may be comprised of a polymeric material.

In some embodiments, the SlipCip device can be modified to include four etched circles that direct the placement of the four red alignment markers. In some embodiments, the device can contain from about 10 to about 10,000 small containers to hold the sample. Prior to attaching the two sides of the device, the containers can be located on either side of the chip. In some embodiments, about 1,000 to about 2,000 containers are used on either half of the chip. In some embodiments, each container has a volume of 4 to 10 nL. In some embodiments, when the two halves are manipulated to combine the reagents and initiate reactions, 10 to 10,000 individual reactions are initiated. In some embodiments, 600 to 2,000 individual reactions are initiated.

In some embodiments, other features may be included on the device to ensure proper manipulation including, but not limited to, for example: detection of proper and complete filling, detection of proper slipping between the plate and the base, detection of errors during slipping, detection of an expired or defective device, detection of bad reagents, etc. for example.

The SlipChip device can contain electrically-conductive material. The material can be formed into at least one area or patch of any shape to form an electrode. The at least one electrode can be positioned on one surface on the base such that in a first position, the at least one electrode is not exposed to at least one first area on the opposing surface on the plate, but when the two parts of the device, base and plate, are moved relative to one another to a second position, the at least one electrode overlaps the at least one area. The at least one electrode can be electrically connected to an external circuit. The at least one electrode can be used to carry out electrochemical reactions for detection and/or synthesis. If a voltage is applied to at least two electrodes that are exposed to a substance in an area or a plurality of areas in fluidic communication or a combination of areas and ducts in fluidic communication, the resulting system can be used to carry out electrophoretic separations, and/or electrochemical reactions and/or transport. Optionally, at least one duct and/or at least one area may be present on the same surface as the at least one electrode and can be positioned so that in a first position, none of the at least one duct and the at least one electrode are exposed to an area on the opposing surface, but when the two parts of the device, base and plate, are moved relative to one another to a second position, the at least one duct and/or at least one area and the at least one electrode overlaps the at least one area.

In some embodiments the elements of a sample containing device, e.g. the SlipChip, are configured to be imagable by a camera, e.g., an iPhone. For example, high contrast materials can be used. For example, components can be constructed to be visible in a single plane. In some embodiments of the windows or transparent materials are used to allow imaging from a predetermined orientation. By imaging various components of the device an image can be generated which can be used to determine if the device is in suitable condition for further analysis. In some embodiments a computer is configured to determine whether components of the device are in proper orientation for analysis of an image to analyze a sample.

Several embodiments of the current invention require movement of a substance through, into, and/or across at least one duct and/or area. For example movement of a substance can be used for washing steps in immunoassays, removal of products or byproducts, introduction of reagents, or dilutions.

6.12 Computer Readable Medium

The computer components, software modules, functions, data stores and data structures described herein can be connected directly or indirectly to each other to allow the flow of data needed for their operations. It is also noted that the meaning of the term module includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality can be located on a single computer or distributed across multiple computers depending upon the situation at hand. In yet another aspect, a computer readable medium is provided including computer readable instructions, wherein the computer readable instructions instruct a processor to execute the methods described herein. The instructions can operate in a software runtime environment. In yet another aspect, a data signal is provided that can be transmitted using a network, wherein the data signal includes data calculated in a step of the methods described herein. The data signal can further include packetized data that is transmitted through wired or wireless networks. In an aspect, a computer readable medium comprises computer readable instructions, wherein the instructions when executed carry out a calculation of the probability of a medical condition in a patient based upon data obtained from the sample. The computer readable instructions can operate in a software runtime environment of the processor. In some embodiments, a software runtime environment provides commonly used functions and facilities required by the software package. Examples of a software runtime environment include, but are not limited to, computer operating systems, virtual machines or distributed operating systems although several other examples of runtime environment exist. The computer readable instructions can be packaged and marketed as a software product, app, or part of a software package. For example, the instructions can be packaged with an assay kit.

The computer readable medium may be a storage unit. Computer readable medium can also be any available media that can be accessed by a server, a processor, or a computer. The computer readable medium can be incorporated as part of the computer-based system, and can be employed for a computer-based assessment of a medical condition.

In some embodiment, the calculations described herein can be carried out on a computer system. The computer system can comprise any or all of the following: a processor, a storage unit, software, firmware, a network communication device, a display, a data input, and a data output. A computer system can be a server. A server can be a central server that communicates over a network to a plurality of input devices and/or a plurality of output devices. A server can comprise at least one storage unit, such as a hard drive or any other device for storing information to be accessed by a processor or external device, wherein the storage unit can comprise one or more databases. In an embodiment, a database can store hundreds to millions of data points corresponding to a data from hundreds to millions of samples. A storage unit can also store historical data read from an external database or as input by a user. In an embodiment, a storage unit stores data received from an input device that is communicating or has communicated with the server. A storage unit can comprise a plurality of databases. In an embodiment, each of a plurality of databases corresponds to each of a plurality of samples. In another embodiment, each of a plurality of databases corresponds to each of a plurality of different imaging devices, for example different consumer based cell phones. An individual database can also comprise information for a plurality of possible sample containment units. Further, a computer system can comprise multiple servers. A processor can access data from a storage unit or from an input device to perform a calculation of an output from the data. A processor can execute software or computer readable instructions as provided by a user, or provided by the computer system or server. The processor may have a means for receiving patient data directly from an input device, a means of storing the subject data in a storage unit, and a means for processing data. The processor may also include a means for receiving instructions from a user or a user interface. The processor may have memory, such as random access memory. In one embodiment, an output that is in communication with the processor is provided. After performing a calculation, a processor can provide the output, such as from a calculation, back to, for example, the input device or storage unit, to another storage unit of the same or different computer system, or to an output device. Output from the processor can be displayed by data display. A data display can be a display screen (for example, a monitor or a screen on a digital device), a print-out, a data signal (for example, a packet), an alarm (for example, a flashing light or a sound), a graphical user interface (for example, a webpage), or a combination of any of the above. In an embodiment, an output is transmitted over a network (for example, a wireless network) to an output device. The output device can be used by a user to receive the output from the data-processing computer system. After an output has been received by a user, the user can determine a course of action, or can carry out a course of action, such as a medical treatment when the user is medical personnel. In some embodiments, an output device is the same device as the input device. Example output devices include, but are not limited to, a telephone, a wireless telephone, a mobile phone, a PDA, a flash memory drive, a light source, a sound generator, a computer, a computer monitor, a printer, and a webpage. The user station may be in communication with a printer or a display monitor to output the information processed by the server.

A client-server, relational database architecture can be used in embodiments of the invention. A client server architecture is a network architecture in which each computer or process on the network is either a client or a server. Server computers are typically powerful computers dedicated to managing disk drives (file servers), printers (print servers), or network traffic (network servers). Client computers include PCs (personal computers), cell phones, or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users.

Subject data can be stored with a unique identifier for recognition by a processor or a user. In another step, the processor or user can conduct a search of stored data by selecting at least one criterion for particular patient data. The particular patient data can then be retrieved. Processors in the computer systems can perform calculations comparing the input data to historical data from databases available to the computer systems. The computer systems can then store the output from the calculations in a database and/or communicate the output over a network to an output device, such as a webpage, a text, or an email. After a user has received an output from the computer system, the user can take a course of medical action according to the output. For example, if the user is a physician and the output is a probability of cancer above a threshold value, the physician can then perform or order a biopsy of the suspected tissue. A set of users can use a web browser to enter data from a biomarker assay into a graphical user interface of a webpage. The webpage is a graphical user interface associated with a front end server, wherein the front end server can communicate with the user's input device (for example, a computer) and a back end server. The front end server can either comprise or be in communication with a storage device that has a front-end database capable of storing any type of data, for example user account information, user input, and reports to be output to a user. Data from each user can be then be sent to a back end server capable of manipulating the data to generate a result. For example, the back end server can calculate corrections for similar cell phones or compile data generated from similar sample collection units. The back end server can then send the result of the manipulation or calculation back to the front end server where it can be stored in a database or can be used to generate a report. The results can be transmitted from the front end server to an output device (for example, a computer with a web browser or a cell phone) to be delivered to a user. A different user can input the data and receive the data. In an embodiment, results are delivered in a report. In another embodiment, results are delivered directly to an output device that can alert a user.

The information from the assay can be quantitative and sent to a computer system of the invention. The information can also be qualitative, such as observing patterns or color, which can be translated into a quantitative measure by a user or automatically by a reader or computer system. In an embodiment, the subject can also provide information other than sample assay information to a computer system, such as race, height, weight, age, gender, eye color, hair color, family medical history, identity, location and any other information that may be useful to the user.

In some embodiments additional information is provided by sensors associated with the device. For example, global positioning data, acceleration data, air pressure, or moisture levels may be measured by a device comprising the image sensor. This additional information can be used by the computer systems of the invention.

Information can be sent to a computer system automatically by a device that reads or provides the data from image sensor. In another embodiment, information is entered by a user (for example, the subject or medical professional) into a computer system using an input device. The input device can be a personal computer, a mobile phone or other wireless device, or can be the graphical user interface of a webpage.

For example, a webpage programmed in JAVA can comprise different input boxes to which text can be added by a user, wherein the string input by the user is then sent to a computer system for processing. The subject may input data in a variety of ways, or using a variety of devices. Data may be automatically obtained and input into a computer from another computer or data entry system. Another method of inputting data to a database is using an input device such as a keyboard, touch screen, trackball, or a mouse for directly entering data into a database.

In an embodiment, a computer system comprises a storage unit, a processor, and a network communication unit. For example, the computer system can be a personal computer, laptop computer, or a plurality of computers. The computer system can also be a server or a plurality of servers. Computer readable instructions, such as software or firmware, can be stored on a storage unit of the computer system. A storage unit can also comprise at least one database for storing and organizing information received and generated by the computer system. In an embodiment, a database comprises historical data, wherein the historical data can be automatically populated from another database or entered by a user.

In an embodiment, a processor of the computer system accesses at least one of the databases or receives information directly from an input device as a source of information to be processed. The processor can perform a calculation on the information source, for example, performing dynamic screening or a probability calculation method. After the calculation the processor can transmit the results to a database or directly to an output device. A database for receiving results can be the same as the input database or the historical database. An output device can communicate over a network with a computer system of the invention. The output device can be any device capable delivering processed results to a user.

Communication between devices or computer systems of the invention can be any method of digital communication including, for example, over the internet. Network communication can be wireless, ethernet-based, fiber optic, or through fire-wire, USB, or any other connection capable of communication. In an embodiment, information transmitted by a system or method of the invention can be encrypted.

It is further noted that the systems and methods can include data signals conveyed via networks (for example, local area network, wide area network, internet), fiber optic medium, carrier waves, wireless networks for communication with one or more data processing or storage devices. The data signals can carry any or all of the data disclosed herein that is provided to or from a device.

Additionally, the methods and systems described herein can be implemented on many different types of processing devices by program code comprising program instructions that are executable by the device processing subsystem. The software program instructions can include source code, object code, machine code, or any other stored data that is operable to cause a processing system to perform methods described herein. Other implementations can also be used, however, such as firmware or even appropriately designed hardware configured to carry out the methods and systems described herein.

A computer system may be physically separate from the instrument used to obtain values from the subject. In an embodiment, a graphical user interface also can be remote from the computer system, for example, part of a wireless device in communication with the network. In another embodiment, the computer and the instrument are the same device.

An output device or input device of a computer system can include one or more user devices comprising a graphical user interface comprising interface elements such as buttons, pull down menus, scroll bars, fields for entering text, and the like as are routinely found in graphical user interfaces known in the art. Requests entered on a user interface are transmitted to an application program in the system (such as a Web application). In an embodiment, a user of user device in the system is able to directly access data using an HTML interface provided by Web browsers and Web server of the system.

A graphical user interface can be generated by a graphical user interface code as part of die operating system or server and can be used to input data and/or to display input data. The result of processed data can be displayed in the interface or a different interface, printed on a printer in communication with the system, saved in a memory device, and/or transmitted over a network. A user interface can refer to graphical, textual, or auditory information presented to a user and may also refer to the control sequences used for controlling a program or device, such as keystrokes, movements, or selections. In another example, a user interface may be a touch screen, monitor, keyboard, mouse, or any other item that allows a user to interact with a system of the invention.

In yet another aspect, a method of taking a course of medical action by a user is provided including initiating a course of medical action based on sample analysis. The course of medical action can be delivering medical treatment to said subject. The medical treatment can be selected from a group consisting of the following: a pharmaceutical, surgery, organ resection, and radiation therapy. The pharmaceutical can include, for example, a chemotherapeutic compound for cancer therapy. The course of medical action can include, for example, administration of medical tests, medical imaging of said subject, setting a specific time for delivering medical treatment, a biopsy, and a consultation with a medical professional. The course of medical action can include, for example, repeating a method described above. A method can further include diagnosing the medical condition of the subject by said user with said sample. A system or method can involve delivering a medical treatment or initiating a course of medical action. If a disease has been assessed or diagnosed by a method or system of the invention, a medical professional can evaluate the assessment or diagnosis and deliver a medical treatment according to his evaluation. Medical treatments can be any method or product meant to treat a disease or symptoms of the disease. In an embodiment, a system or method initiates a course of medical action. A course of medical action is often determined by a medical professional evaluating the results from a processor of a computer system of the invention. For example, a medical professional may receive output information that informs him that a subject has a 97% probability of having a particular medical condition. Based on this probability, the medical professional can choose the most appropriate course of medical action, such as biopsy, surgery, medical treatment, or no action. In an embodiment, a computer system of the invention can store a plurality of examples of courses of medical action in a database, wherein processed results can trigger the delivery of one or a plurality of the example courses of action to be output to a user. In an embodiment, a computer system outputs information and an example course of medical action. In another embodiment, the computer system can initiate an appropriate course of medical action. For example, based on the processed results, the computer system can communicate to a device that can deliver a pharmaceutical to a subject. In another example, the computer system can contact emergency personnel or a medical professional based on the results of the processing. Courses of medical action a patient can take include self-administering a drug, applying an ointment, altering work schedule, altering sleep schedule, resting, altering diet, removing a dressing, or scheduling an appointment and/or visiting a medical professional. A medical professional can be for example a physician, emergency medical personnel, a pharmacist, psychiatrist, psychologist, chiropractor, acupuncturist, dermatologist, urologist, proctologist, podiatrist, oncologist, gynecologist, neurologist, pathologist, pediatrician, radiologist, a dentist, endocrinologist, gastroenterologist, hematologist, nephrologist, ophthalmologist, physical therapist, nutritionist, physical therapist, or a surgeon.

The image can be uploaded to the cloud. In some embodiments, the image can be automatically uploaded to the cloud without user interaction. The images uploaded to the cloud can be sent to one or more local computers or devices. The images can be synced between multiple computers and/or devices. The uploading and syncing of images can be controlled by softward. For instance, the Symbian software on which the Nokia 808 camera runs has access to the cloud-based storage service Skydrive, produced by Microsoft, and the uploaded files are then instantly synced with all computers that have the Skydrive application installed and are logged into the same account. The can be accomplished on other platforms. For instance, the images can be automatically uploaded to the cloud and synced using Android or iOS architectures. Non-limiting examples of existing software solutions include box.net, dropbox, skydrive, and iCloud. By using a cloud-based architecture for the automatic transfer of images from the mobile device to a computer, virtually any available smartphone on the market can be tied into our automatic analysis software without any fine-tuning or tweaking of the software for the various operating systems and handsets available on the market today. Using a cloud-based service to extract the images from the cell phone can allow for easy archiving and traceability of the images and raw data.

In some embodiments, the images are maintained on the device comprising the image sensor, and not sent to the cloud or synced. Software can be written to do direct image analysis on the device comprising the image sensor. Handling the processed images offsite also allows for the saving of the processed images without having to deal with bandwidth for transmitting those from the phone, or having a cell phone with a limited size run out of room for additional files. Partial or complete image processing on the cell phone can also be directly performed.

Image analysis can be performed in a Labview program with the following workflow. Once an image is taken on the cell phone, it can be automatically transferred to any computer in the world, e.g., via the Skydrive cloud. Meanwhile, the Labview program can be written to "watch" any folder on the computer for new files that fit into a specific filtered category (i.e., *.jpg, *.png, *.tiff) and automatically analyze those files. Such a program can be multithreaded such that the "watcher" and the "analyzer" of the software can run simultaneously without disruption. Upon a new file being added to the watched folder (via cloud syncing), it is added to a queue that the analyzer watches. The queue can have multiple files waiting in it, so it is not a problem if images are being photographed faster than the software can handle, or in the case of simply adding to the watched folder a set of files that have not previously been analyzed. Thus the analysis software is not tied to any specific platform either and can be easily modified to analyze images from any device whether it be cellular phone, compact camera, dslr, microscope, etc.

Once the number of positive wells has been determined, that number is processed using Poisson statistics and prior knowledge about the chip in question to determine the original concentration of sample in the chip. This information is then automatically sent via email to any valid email account and is then received by the original person who took the image regardless of where they are in the world relative to the computer that performs the image analysis. The time that elapses between the taking of the image and the receipt of email confirmation has been performed in well under 1 minute, although actual time is subject to the upload speed on the network of the cell phone and download speed on the network of the computer. This is important, because if an error is detected in the course of an analysis, such as not being able to find all 4 spots, the user needs to be quickly alerted that another image must be taken. The software has been programmed to do such, and the user typically knows in under 1 minute to take another image. Having the ability to notify by email can give the ability to notify via text. Cell phone providers can have a service that will send the body of an email as a text to specific users. Other servers that can be leveraged as SMS messengers. The analysis process can use computer automation to notify a user if the image can be used. The notification can be an SMS message, email message, phone call, web posting, or electronic message for example. In some embodiments, the amount of time from the uploading of the image until the user is notified can be referred to as the analysis process. The analysis process can take less than 5 min, 4 min, 3 min, 2 min, 1 min, 50 sec, 45 sec, 40 sec, 30 sec, 20 sec, 10 sec, 9 sec, 8 sec, 7 sec, 6 sec, 5 sec, 4 sec, 3 sec, 2 sec, 1 sec, 0.5 sec, 0.4 sec, 0.3 sec, 0.2 sec, or 0.1 sec, for example. In some embodiments, the analysis process takes less than 1 min.

In an embodiment, at least one calibration source can be provided for a calibration emission, and at least one calibration photodiode can be used for sensing the calibration emission wherein the control circuitry has a differential circuit for subtracting the calibration photodiode output from each of the detection photodiode outputs.

In an embodiment, a communication interface can be a universal serial bus (USB) connection such that the outer casing is configured as a USB drive.

In some instances the information is transmitted back to the mobile device that was used for imaging. For example an image can be obtained, sent to a separate computer for analysis, and then the image or date related to the image can be transmitted back to the mobile device. In some embodiments an image and/or a processed image and/or resulting data the user is transmitted to a separate device, e.g., a physician's mobile device can receive the information. In some instances two or sets of information are transmitted to two or more devices. The two or more sets of information can be the same information, or in some embodiments, separate data is sent to each user. For example a patient may receive some information related to an image while the patient's doctor receives information more suitable for a physician's analysis.

While offloading the analysis of images to "the cloud" provides a number of benefits, including traceability and archiving of raw data, global access, and compatibility with virtually all smartphone operating systems, it requires a wireless data connection of sufficiently high bandwidth; thus, direct on-phone analysis could be preferable in some scenarios.

6.13 Applications

An assay can be conducted in less than or equal to about: 600 minutes, 540 minutes, 480 minutes, 420 minutes, 360 minutes, 300 minutes, 240 minutes, 180 minutes, 120 minutes, 110 minutes, 100 minutes, 90 minutes, 80 minutes, 70 minutes, 60 minutes, 50 minutes, 40 minutes, 30 minutes, 20 minutes, 15 minutes, 10 minutes, 9 minutes, 8 minutes, 7 minutes, 6 minutes, 5 minutes, 4 minutes, 3 minutes, 2 minutes, or 1 minute. An assay can have an accuracy of at least about 50%, 60%, 70%, 80%, 90%, 95%, 96%, 97%, 98%, 99%, 99.9%, or 99.99%. The rates of false positives can be below 10%, below 1%, below 0.1%, below 0.01%, below 0.001%, or below 0.0001%. The rates of false negatives can be below 10%, below 1%, below 0.1%, below 0.01%, below 0.001%, or below 0.0001%.

Assays can be used for single-nucleotide polymorphism (SNP) detection.

Assays can be used for detecting copy number variations (CNVs). CNVs are a form of structural variation, alterations of the DNA of a genome that changes the number of copies of one or more sections of the DNA.

An assay can be used for quantitative detection of nucleic acids, such as Hepatitis C RNA. For example, a method can be used comprising the steps of taking a sample from the patient, accessing RNA in the sample or extracting RNA from the sample, using at least one RT-LAMP primer set to reverse transcribe and amplify the RNA in a qualitative and/or in a quantitative format, and testing for amplification to confirm presence of nucleic acids including but not limited to Hepatitis C RNA.

Assays can be used for genotyping, i.e., determining differences in the genetic make-up (genotype) of an organism or group of organisms by examining the DNA or RNA sequence and comparing it to a reference sequence. This can be used to define biological populations by use of molecular tools.

Assays can be used for detecting epigenetic marks or modifications (e.g., methylation, glycosylation, hydroxymethylation): Epigenetic modifications can comprise functionally relevant modifications to the genome that do not involve a change in the nucleotide sequence.

Assays can be used for identification of mutations, such as drug resistance mutations (DRM). Drug resistance can be achieved by multiple mechanisms, including horizontal acquisition of resistance genes (carried by plasmids or transposons), by recombination of foreign DNA into the chromosome, or by mutations in different chromosomal loci.

Assays can be used to screen for transgene integration. A transgenic organism has in its cells a foreign gene that has been inserted by laboratory techniques or inherited from a transgenic parent organism. Transgenic organisms can be produced by introducing cloned genes, composed of DNA from microbes, animals, or plants, into plant and animal cells. Transgenic technology affords methods that allow the transfer of genes between different species. Identification of a genetically modified organism (e.g., food or laboratory animals) may be accomplished using the methodologies described herein.

Analysis of other viruses (including detection, typing, subtyping, SNP detection, and other analysis) can be performed analogously. Analysis of Hepatitis viruses, including HCV, HBV, HAV, HIV, HPV, and other viruses of relevance to human health, agriculture, agricultural biotechnology, and other practical applications, can be performed. Analysis and detection of viral, archaeal, bacterial, fungal, mammalian, human, and other nucleic acids can be performed. Analysis and detection includes comparative analysis and detection, where a target nucleic acid is compared with another nucleic acid.

The methodologies described herein can be used to detect other activities in conjunction with detection and or amplification such as reactions that make or break chemical bonds, reactions that lead to formation of complexes between molecules, or reactions that lead to formation of complexed between molecules and objects such as beads and surfaces.

Assays can be used to identify drug resistance mutations (DRMs). Drug resistance can be achieved by multiple mechanisms, including but not limited to horizontal acquisition of resistance genes (carried by plasmids or transposons), by recombination of foreign DNA into the chromosome, or by mutations in different chromosomal loci.

Assays can be used for genetic testing, including fetal genetic testing.

Assays can be used for epigenetic testing for diseases and other conditions, including but not limited to Angelman syndrome, Prader-Willi syndrome, Beckwith-Wiedemann syndrome, aberrant DNA methylation associated with cancer (hypermethylation, e.g., at CpG islands in the promoter region or hypomethylation, e.g., global hypomethylation), epigenetic changes (e.g., CpG island methylation) associated with reduced expression of DNA repair genes (e.g., BRCA1, WRN, FANCF, RAD51C, MGMT, MLH1, MSH2, ERCC1, Xpf, NEIL1, FANCB, MSH4, ATM), and variant histones.

Assays can be used to identify or characterize mobile genetic elements (e.g., transposons and bacteriophages) or foreign genes inserted by laboratory techniques (e.g., genes inserted into genetically modified organisms).

Assays can be used identification of single point mutations, for example for viral genotyping. Genotyped viruses can include but are not limited to hepatitis C virus, hepatitis B virus, human immunodeficiency virus, human cytomegalovirus, norovirus and enterovirus.

Assays can be used for viral typing and subtyping. Typed or subtyped viruses can include but are not limited to human papilloma virus, avian influenza virus, human influenza virus, swine influenza virus, herpes simplex virus, foot and mouth disease virus, dengue virus and rotavirus.

Assays can be used for bacterial typing. Typed bacteria can include but are not limited to *Francisella* spp., *Escherichia* spp., *Salmonella* spp., *Mycobacterium* spp., *Bacillus* spp., *Staphylococcus* spp., *Streptococcus* spp., *Acinetobacter* spp., *Helicobacter* spp., *Bordetella* spp., *Bordetella* spp. and *Vibrio* spp.

Assays can be used to assess for the presence or absence of drug resistance mutations, in subjects including but not limited to human immunodeficiency virus, hepatitis C virus, and cancer drug resistance.

7. EXAMPLES

7.1 Example 1

7.1.1. Selection of Indicator Dye.

The method of the present invention comprises the following steps as illustrated in FIG. 2A. Single nucleic acid molecules and indicator dye are compartmentalized on a microfluidic device and followed by isothermal nucleic acid amplification. In the figure, positive reaction solutions are presented in blue; and negative reactions are presented in purple. After ratiometric image processing, positive reactions become white and negative reactions become black—an unambiguous binary result. The number of positive wells can be used to quantify the concentration of the input target.

To eliminate the need for a fluorescent readout in single-molecule amplification and produce a readout that can be imaged by any cell phone camera under various illumination conditions, one can use a nucleic acid amplification-indicator dye that changes color in response to amplification. A robust colorimetric readout balances two opposing requirements: the indicator dye must be sufficiently concentrated (or present in a large enough volume) to provide readable absorbance (i.e., smaller volumes and shorter path lengths require greater concentrations of dye for sufficient absorbance to be detected) but not so concentrated that the dye interferes with the amplification reaction. To optimize a visual readout system for single-molecule counting with an unmodified cell phone camera, we first identified the factors that contribute to hypothetical limitations of a visual readout system, including the range of reaction volumes (or path lengths) at which a particular indicator could be used to monitor amplification and the range of indicator concentrations that would not interfere with the amplification reaction. Where these ranges overlap are the optimal volumes and dye concentrations at which a reaction is not inhibited and can provide a change in absorbance that is sufficient for readout with an unmodified camera phone (dotted green region of FIG. 2B).

The process of identifying the optimal volumes and dye concentrations is further illustrated in FIG. 2B. In the figure, the green-shaded region indicates the range of acceptable dye concentrations for visualization with an unmodified cell phone camera (area labeled "Acceptable concentration range for visualization"). Concentrations to the left of the green region are too low for visualization (labeled "Concentration too low for visualization"); concentrations to the right of the green region are too high (labeled "Concentration too high for visualization"). Within this green region, the dotted area indicates dye concentrations that both enable readout with an unmodified cell phone camera and do not inhibit the amplification reaction. The area to the right of the red line indicates dye concentrations that interfere with amplification making accurate quantification based on real-time data challenging.

We validated this visual readout approach using loop-mediated isothermal amplification (LAMP) because this method has been well characterized and validated previously for single-molecule analyses. LAMP chemistry is based on an auto-cycling strand displacement reaction performed at a constant temperature to synthesize large amounts of amplified product; a LAMP reaction generate more than 109 copies of template within 1 h of incubation at 60-65° C. We used a cubic reaction volume of 8 nL (200×200×200 μm³), which is in the range of volumes used in digital experiments. We assume that an appropriate indicator of an amplification reaction will have a change in absorbance that equates to a change of extinction coefficient of ~25,000 L mol-1 cm-1 upon reaction (this number approaches the maximum achievable change in absorbance for small-molecule dyes). We use the Beer-Lambert law ($A=\varepsilon L c$, which describes the relevant parameters to consider for visualization, wherein A=absorbance; $\varepsilon$=extinction coefficient (L mol-1 cm-1); L=length of the light's path through the solution (cm); c=concentration of absorbing species (mol/L). At a path length of 0.2 mm, an estimated ~2 mM concentration of the dye is required to reach a change of absorbance of 1 unit. Given these parameters, to obtain a readout that can be captured by an unmodified mobile phone, we predicted that an appropriate indicator dye would be one that responds to each nucleotide incorporation (present in mM concentrations), as opposed to responding only to the number of produced molecules (amplicons), which would not exceed primer concentration (present in the μM range).

Colorimetric approaches to visual detection of nucleic acid amplification typically measure absolute changes in color intensity, however distinguishing color change—e.g., purple vs. blue—is difficult and therefore not an appropriate way to quantify readout under variable conditions, such as in LRS. Ratiometric measurements, which take the ratio of two independent measurements under the same conditions, improve the robustness of a colorimetric approach, converting results to a yes/no binary outcome, eliminating the need for the user to differentiate colors. We hypothesized that a cell phone camera's sensor, which reads in three color channels (red, green and blue, RGB) could provide suitable information for using a ratiometric approach to read amplification reactions at the single molecule level. The example we considered here is the back-illuminated Exmor R CMOS image sensor used on popular cell phones such as the Samsung Galaxy 4, iPhone 4S and iPhone 5, which has a sensitivity maxima of ~520 nm (green), ~459 nm (blue) and ~597 nm (red) (FIG. 3A).

To illustrate our methodology for a hardware-agnostic visual readout with a ratiometric approach, we selected eriochrome black T (EBT), a magnesium ion indicator that meets the aforementioned dye specifications and has been used previously for visualization of LAMP products. During an isothermal amplification reaction, as nucleotides are incorporated, protons and bi-product pyrophosphate ions (P2O74-) are produced and these ions can strongly bind metal ions (e.g., $Mg^{2+}$ ions) and form insoluble salts, decreasing the concentration of metal ions in the reaction solution. Before the amplification reaction, EBT is bound to magnesium ions and the reaction solution is purple. As a LAMP reaction proceeds in the presence of target nucleic acid, it is suggested that EBT is deprived of $Mg^{2+}$ bp newly generated pyrophosphate ions, and the reaction solution turns blue.

We hypothesized that EBT would be amenable to colorimetric analysis with a cell phone camera because, in RGB terms, in a positive LAMP reaction containing EBT dye, there is higher transmittance in the blue channel (blue LAMP reaction solution), while in a negative LAMP reaction transmittance remains high in the blue and red channels (purple LAMP reaction solution) (FIG. 3A). These observed changes in transmittance between positive and negative reactions can be captured by the Exmor R optical sensor (FIG. 3A), which matches well with the observed differences between positive and negative transmittance profiles of LAMP reactions containing EBT (FIG. 3A).

7.1.2. Optimization of Ratiometric Approach.

We tested whether the suitability of an indicator dye can be evaluated for a ratiometric approach prior to experimental validation by predicting the RGB values read by a cell phone camera for a positive and a negative reaction. First, we took the transmittance spectra for positive and negative amplification reactions containing EBT and convoluted them with the normalized spectral responses for each of the RGB channels in an Exmor R CMOS sensor58 providing six curves (a positive and negative for each of the three color channels). Next, we calculated the area under each curve and took its square root (to account for the standard square-root scaling with nonscientific devices used for imaging), providing the predicted RGB values (FIG. 3B) for positive (R=185, G=197 and B=209) and negative (R=219, G=190 and B=212) RT-LAMP reaction solutions in the presence of EBT at this particular concentration. These values can then be evaluated to select the optimal ratiometric approach for this particular indicator dye. In an RGB color scheme, there are three possible combinations for ratiometric analysis: G/R, B/R or G/B. The predicted RGB values for a positive and a negative reaction are used to calculate the ratios for each channel combination (FIG. 3D); the ratio with the greatest difference between positive and negative outcomes (G/R in this example) is predicted to be the most robust ratiometric analysis.

Using the approach described above, we predicted the RGB ratios for a positive and negative RT-LAMP reaction in the presence of two additional indicator dyes: hydroxynaphthol blue (HNB) and calmagite. HNB is being reported increasingly in the literature for LAMP visualization and calmagite is an analogue of EBT dye with the nitro group absent (more stable version). A side-by-side comparison showed that the greatest predicted difference between positive and negative RT-LAMP reaction, as captured by an unmodified cell phone camera, would be achieved using EBT as the indicator dye and G/R as the ratiometric combination (FIGS. 4A-F). Based on these predicted ratios, we decided to validate our methodology using EBT as the indicator dye. We confirmed the storage stability of the EBT dye stock solution in the dried state (FIG. 5), as this is a critical requirement for the use of a dye in real point-of-need diagnostic applications. EBT serves as our validation dye in this invention, however our methodology is designed to be applicable to alternative dyes.

To experimentally validate this approach to predicting an optimal ratiometric combination, we performed an RT-LAMP reaction for HCV RNA containing EBT as the indicator dye and captured an image of the readout with an unmodified camera phone (iPhone 4S) (FIG. 3C). We processed the readout image; color channels of the original image were split and all three channel ratios (G/R, B/R, G/B) were calculated to derive a ratiometric image for each ratiometric combination. These experimental ratios obtained with an unmodified cell phone camera (FIG. 3E) matched well with the predicted values (FIG. 3D) for each of the three ratiometric combinations, confirming the predictive power of this approach. The G/B ratio was identified as less appropriate for distinguishing positive and negative reactions because the values for positive and negative reactions were similar; G/R and B/R ratios were identified as suitable because there was sufficient contrast between the values for positive and negative reactions. For the G/R combination, the ratio obtained after a negative reaction was 0.91 and the ratio from a positive reaction was 1.03—a difference of 0.12 (FIG. 3E). For the B/R combination, the ratios for negative and positive reactions were 0.98 and 1.07—a difference of 0.09 (FIG. 3E). Therefore, we selected the G/R combination for our subsequent validation experiments. Counting positives is a more intuitive approach, so the B/R ratio (where the positive ratio had the greatest difference from the background) can be a useful and attractive method. However, it is generally more desirable to select a ratio that includes the green channel because most single-chip digital image sensors used in digital cameras, including cell phones, utilize a Bayer filter mosaic pattern that is composed of 50% green, 25% red and 25% blue pixels.

7.1.3. Validation of Ratiometric Approach

To test the robustness of our approach to different hardware and illumination conditions, we used HCV RNA amplified by RT-LAMP at two-fold increasing concentrations of indicator dye ranging from 10.9 µM to 1.4 mM (for a total of eight dye concentrations). After RT-LAMP amplification, 50 µL of each reaction solution were transferred to 96-well plates (path length of ~1.5 mm) and the readout was imaged with cameras from four common cell phone models: Apple iPhone 4S (FIG. 6A), HTC inspire 4G (FIG. 6B), Motorola Moto G (FIG. 6C) and Nokia 808 PureView (FIG. 6D). FIGS. 4 A-G provide enlarged and cropped color images (top two rows of each individual panel) captured by an unmodified cell phone camera from positive (+) and negative (−) RT-LAMP reactions at two-fold increases in EBT concentration from 10.9 µM to 1.4 mM (1=0.011 mM; 2=0.022 mM; 3=0.044 mM, 4=0.088 mM, 5=0.175 mM; 6=0.35 mM; 7=0.7 mM; 8=1.4 mM). Positive wells are blue and negative wells are purple. After G/R ratiometric processing (bottom two rows of each individual panel) negative wells are black. Regions I, II, III in each panel indicate the effect of dye concentration: (II) Acceptable concentration range for visualization (green regions); (I) Concentrations too low for visualization (white regions); and (III) Concentrations too high for visualization (red regions).

Under fluorescent light and using the G/R ratiometric process (green channel divided by red channel followed by a threshold adjustment to generate a binarized black and white image), we determined that EBT concentrations lower than 0.175 mM provided an insufficient color change for detection with a cell phone camera (FIG. 6, region I, white background), while concentrations of 1.4 mM inhibited the amplification reaction (FIG. 6, region III, red background). For this particular indicator dye, the range of concentrations at which color change could be detected by an unmodified cell phone camera and no inhibition was observed at the endpoint of the reaction was identified as 0.175 mM to 0.7 mM (FIG. 6, region II, green background; supporting information in FIG. 7). Some cell phone cameras were more sensitive (e.g., HTC inspire 4G was able to distinguish a positive result at EBT concentrations as low as 0.0875 mM) (FIG. 6B), but all four cell phone models distinguished a positive reaction at concentrations between 0.175-0.7 mM (FIG. 6, region II, green background). We then chose one cell phone with the most representative performance (Apple iPhone 4S) to test the robustness of the G/R approach to different lighting conditions. Under all conditions tested: incandescent light (FIG. 6E), direct sunlight (FIG. 6F) and indirect sunlight (FIG. 6G), the optimal EBT concentration range that we identified under fluorescent light (0.175-0.7 mM) could be read clearly, confirming the robustness of the ratiometric approach to variations in illumination.

7.1.4. G/R Ratiometric Process

G/R ratiometric process is described in more detail in FIG. 8 with images generated in each step of the process. In the figure, the top row of each panel (eight wells) shows a positive RT-LAMP reaction containing EBT solution at two-fold increasing concentrations from 10.9 µM to 1.4 mM (from left to right). The bottom row of each panel (eight wells) shows negative RT-LAMP reactions containing EBT solution at two-fold increasing concentrations from 10.9 µM to 1.4 mM. FIG. 8A provides a raw image acquired by a cell phone camera. The same image after white balance correction is provided in FIG. 8B. FIG. 8C shows images after red, green and blue color channels separation. Resulting image after green channel is divided by red channel as illustrated in FIG. 8D. FIG. 8E provides a binary image after a threshold correction. Positive reactions (originally blue) are white and negative reactions (originally purple) are black. Image processing was performed with Image J (ver. 1.49).

Images acquired with unmodified cell phone cameras were processed as described above and presented in FIG. 8. Original color images from the unmodified cell phone cameras show negative (bottom two rows) and positive (top two rows) RT-LAMP reactions. From left to right, EBT concentration is increased in two-fold increments between 10.9 µM to 0.088 mM (bottom row) and 0.175 mM to 1.4 mM (second row from the bottom). Positives contained HCV RNA and the same EBT concentration pattern was repeated. Negative wells are purple and positive wells are blue. Ratiometric G/R-processed images show the binary result in which the negative wells become black and the positive wells become white. FIGS. 9A-D provide images collected with four common cell phones under fluorescent light: (FIG. 9A) Apple iPhone 4S, (FIG. 9B) HTC inspire 4G, (FIG. 9C) Motorola Moto G and (FIG. 9D) Nokia 808 PureView. FIGS. 9E-G provide images collected with Apple iPhone 4S under different light conditions: (FIG. 9E) incandescent light, (FIG. 9F) direct sunlight and (FIG. 9G) indirect sunlight. Image processing was performed with ImageJ (ver. 1.49).

7.1.5. One-Step Method for Digital Visual Readout.

Microfluidic devices enable ultrasensitive digital quantification. Small well volumes are valuable because they enable faster reactions (because concentrations are high in single wells), minimize the effects of inhibitory materials (due to their isolation into wells) and expand the upper limit of the dynamic range (because single molecules can be confined from samples containing high template concentrations). However, as well volumes (and path lengths) decrease, color visualization becomes challenging for a mobile phone. To compensate, the concentration of the indicator dye can be increased, however high concentrations of some dyes inhibit amplification reactions. Thus, there are inherent physical limits to a colorimetric approach. To validate that this visual readout approach could be applied to single-molecule amplification at nanoliter volumes, we used digital LAMP (dLAMP) and phage lambda DNA (λDNA) as a target. We specifically aimed to resolve three questions: (i) Can we obtain a visual readout for amplified single molecules that can be captured by an unmodified cell phone camera? (ii) Is volume a factor in achieving a digital visual readout? (iii) Does ratiometric processing work for small volumes?

To answer these questions, we designed a multivolume rotational SlipChip device containing 1,240 wells of eight volumes ranging from 15 nL to 50 nL. (FIGS. 10-11B). We loaded these devices with LAMP reaction solution containing an appropriate target concentration in the middle of the device's dynamic range, a fluorescent DNA-detecting intercalation dye (Syto 9), and EBT dye at 0.7 mM (the highest non-inhibiting concentration identified in FIG. 4). We imaged this device with a house-built real-time fluorescence imager, with a Leica stereoscope (optimal imaging conditions) and with an Apple iPhone 4S. The number of positive counts based on fluorescence was 261, while 260 positives were counted using the indicator dye and G/R process both with the stereoscope and the cell phone (FIG. 12). This experiment showed that the G/R method could be used in place of fluorescence readout to count amplified single molecules and that the readout capture and G/R processing performed on an unmodified cell phone matched the results obtained under optimal lighting conditions (stereoscope). Additionally, using a device containing 800 wells of 27 nL, we observed excellent correlation among positive counts obtained from the stereoscope, fluorescence imager and cell phone camera (FIG. 13).

While investigating the limits that reaction volume may impose on visual readout, we observed that the estimated template concentration determined from each of the eight well volumes produced similar Most Probable Numbers (MPN) of molecules (mean 8,500±1,500 copies/mL) (FIG. 14A) (estimated concentration from all volumes are within 95% confidence interval at each volume, detailed in FIG. 15). In addition, all SlipChip devices, analyzed independently, gave similar target concentrations (8,400±500 copies/mL) (FIG. 14B), suggesting that the selected indicator dye did not impair quantification of single molecules in well sizes 15-50 nL and that these well volumes can be imaged reliably with either a stereoscope or an unmodified cell phone camera. However, the cell phone camera images of well volumes of 15 nL were less clear than those obtained from the stereoscope, suggesting that volumes of ~15 nL may approach the limit of colorimetric imaging with current camera phone sensors, although as higher quality sensors are integrated into commercial cell phones, this limit would change.

7.1.6. Two-Step Method for Digital Visual Readout.

We next developed a method to apply the visual readout approach to digital devices that contain smaller well volumes. To be able to image at small volumes (e.g., 5 nL) on a microfluidic device, one must balance the need for greater indicator color intensity for visualization with the need to keep dye concentrations below the level of inhibition (FIG. 3 region III) for an amplification reaction. High concentrations of indicator dye can completely halt an amplification reaction, and we knew from performing real-time bulk experiments that even when reactions are positive, an indicator dye can still interfere to some extent with isothermal nucleic acid amplification—for both RNA and DNA we observed delays in the time-to-positive, and this delay increased at greater concentrations of the indicator dye, even though reactions were positive. (FIG. 16). We hypothesized that we could prevent inhibition completely by decoupling the amplification step from the readout step. To do this, we designed a two-step SlipChip device (based on previous SlipChip designs, FIGS. 17-18) in which the amplification solution and the detection solution are loaded into separate wells (FIG. 19A). We validated this two-step protocol with a clinically relevant target, purified HCV RNA, using digital reverse transcription-LAMP (dRT-LAMP). First, we performed digital isothermal amplification in the set of small (5 nL) amplification wells (in the absence of the indicator dye) (FIG. 19A (i)). After amplification, a "slip" was performed and the amplification wells came into contact with a second set of larger (9.5 nL) wells, which contained the indicator dye—for a total well volume of 14.5 nL (FIG. 19A (ii)). Immediately after mixing, negative wells lacking target molecules stayed purple and wells containing positive reactions turned blue (FIG. 19A (iii)). Ratiometric image processing (G/R process) provides a single binary result (positive or negative) (FIG. 19A (iv)). Counts obtained by a house-built real-time imaging instrument (to read fluorescence), and counts obtained by G/R processing from an image captured by an unmodified cell phone camera were significantly correlated (Pearson's Con=0.9998; R2=0.9996) (FIG. 19H), showing that this two-step SlipChip-based protocol provides a suitable visual readout for digital single-molecule amplification for devices containing wells of small volumes.

Devices shown in this invention were not designed to achieve clinically relevant concentrations in the lower detection limit of quantification (LDL) because larger well volumes do not represent a challenge when imaging with a mobile phone. Instead, we studied the performance of our approach with wells of small volumes to ensure that this method meets the ULQ required for clinical relevance. The upper limit of quantification (ULQ) is determined by the total number of wells with the smallest volume. As an example, for SlipChip devices with 800 wells of 5 nL the ULQ is 1,162,413 copies/mL, while a SlipChip device with 10,000 wells of 5 nL the ULQ is 1,622,660 (calculations performed according to Kreutz, et al. 2011.

7.1.7. Summary

Here we show that single nucleic acid molecules can be detected and counted with an unmodified cell phone camera by employing microfluidic technology, sequence-specific isothermal amplification, and a judiciously chosen amplification-indicator dye. We further show that ratiometric processing of the cell phone image enables robust quantification without the need for a user to differentiate colors. The general methodology we developed can be used as a guideline to enable others to develop their own cell phone based single-molecule counting approach.

The methodology includes the following steps: First, an appropriate amplification indicator should be selected. Indicators should respond optically to each nucleotide incorporation event (as opposed to responding to number of produced molecules) resulting in a change in the transmittance profile in the wavelength range of visible light (400-700 nm). The indicator dye should have a change in absorbance matched to the spectral sensitivity of the image sensor in an unmodified cell phone; for ratiometric processing, the solution should have a large relative change in transmittance in color channels for which the camera's image sensor is most sensitive. Second, the color ratio used in the ratiometric approach is chosen based on the spectral sensitivity of the image sensor in an unmodified cell phone. This step can be done in silico to identify the dye with the ratio that provides an unambiguous binary readout of positive and negative reactions that is robust to illumination and hardware conditions. Third, the selected dye and ratiometric approach should be validated using the desired amplification chemistry. Experiments should be performed to establish the range of dye concentrations and well volumes at which an amplification reaction is not inhibited and at which imaging can be done with an unmodified cell phone. For some indicator dyes, the range of suitable well volumes and concentrations will be too narrow. In such situations, an alternative approach is to use a two-step device that separates the amplification and readout steps. Processing can be done directly on a cell phone or uploaded wirelessly to a cloud server to swiftly communicate results.

We anticipate that the capabilities of visual readout for counting single molecules will extend further as cell phone camera technology advances, as additional indicators are available (e.g. metal ions, pH indicators) and as additional types of amplification reactions are developed. Devices that integrate sample preparation, nucleic acid amplification and a visual digital readout that can be captured easily will be a critical breakthrough toward bringing quantitative, ultrasensitive measurements outside of central laboratories—a key step for in vitro diagnostics, pandemic surveillance and environmental monitoring.

7.1.8. Methods

Chemicals and Materials.

All chemicals were purchased from commercial sources. The LoopAmp® RNA amplification kit (Eiken Chemical Co., Ltd., Japan) was purchased from SA Scientific (San Antonio, Tex., USA). The LoopAmp® RNA amplification kit contains 2× Reaction Mix (RM) (40 mM Tris-HCl pH 8.8, 20 mM KCl, 16 mM MgSO4, 20 mM (NH4)2SO4, 0.2% Tween20, 1.6 M Betaine and dNTPs 2.8 mM each), Enzyme Mix (EM) (mixture of Bst DNA polymerase and AMV reverse transcriptase), and distilled water (DW). Bovine serum albumin (BSA) was purchased from Roche Diagnostics (Indianapolis, Ind., USA). Phage lambda DNA (500 µg), SUPERase In RNase Inhibitor (20 U/µL), Eriochrome Black T (EBT) dye, mineral oil (DNase, RNase, and Protease free), tetradecane, Costar™ Clear Polystyrene 96-Well Plates, Corning® Universal Optical Microplate Sealing Tape, and DEPC-treated nuclease-free water were purchased from Thermo Fisher Scientific (Hanover Park, Ill., USA). Chelex® 100 resin was purchased from Bio-Rad (Hercules, Calif., USA). Trehalose Solution (1 M) was purchased from Amersham Life Science (Cleveland, Ohio, USA). Tris-HCl buffer stock solution (1 M, pH 8.0) was purchased from Affymetrix (Santa Clara, Calif., USA). All primers were produced by Integrated DNA Technologies (Coralville, Iowa, USA). Dichlorodimethylsilane was purchased from Sigma-Aldrich (St. Louis, Mo., USA). SYTO® 9 Stain and AcroMetrix® HCV High Control were purchased from Life Technologies (Grand Island, N.Y., USA). Nucleic acid extraction kit QIAamp Viral RNA Mini kit was purchased from QIAGEN Inc. (Valencia, Calif., USA). Eppendorf Mastercycler Gradient PCR Themal Cycler was purchased from Eppendorf (Hamburg, Germany). POLARstar Omega microplate reader was purchased from BMG Labtech (Durham, N.C., USA). Leica MZ Fl III stereoscope with PLAN 0.5× lens was purchased from Leica Microsystems (Bannockburn, Ill., USA). Photomasks were designed in AutoCAD 2013 and ordered from CAD/Art Services, Inc. (Bandon, Oreg., USA). Soda-lime glass plates coated with layers of chromium and photoresist were ordered from the Telic Company (Valencia, Calif., USA).

SlipChip Device Design.

The multivolume rotational SlipChip device design was used to demonstrate the one-step method for digital visual readout; this device was composed of 1,240 microfluidic wells, with the following volumes: 160 wells×15 nL, 160× 17.5 nL, 160×20 nL, 160×22.5 nL, 160×25 nL, 160×40 nL, 160×45 nL, 120×50 nL (FIG. 10). The total combined volume of all wells was 35.6 µL. For loading, one inlet hole (in the middle ring structure) and four oil escape holes (in the outer ring structure) were drilled in the top plate. The two-step SlipChip device was used to demonstrate a two-step method for digital visual readout; this device was based on previously published SlipChip designs.[13] For the two-step SlipChip design used in this study, the device was modified in the following ways: (i) the number of each type of well was reduced to 800; (ii) Space was added between the arrays to allow for the incubation conformation; (iii) The sequence of well loading was reversed (the smaller 5 nL wells are loaded before the larger 9.5 nL wells). See FIG. 17 for more details.

SlipChip multivolume designs for HCV and HIV viral load quantification at clinically relevant dynamic ranges is provided below in Table 4.

TABLE 4

Multivolume device designs for viral load quantification.

| Volumetric step | Number of well volumes | Well volume range (nL) | Number of wells per device | LDL-ULQ (copies/mL) | DR (log) |
|---|---|---|---|---|---|
| 2 | 6 | 5-160 | 2,700 | 500-1,000,000 | 3.3 |
| 2 | 6 | 5-160 | 2,700 | 50-1,000,000 | 4.3 |
| 5 | 3 | 5-125 | 1,350 | 500-1,000,000 | 3.3 |
| 5 | 3 | 5-125 | 1,350 | 50-1,000,000 | 4.3 |
| 25 | 2 | 5-125 | 900 | 500-1,000,000 | 3.3 |
| 25 | 2 | 5-125 | 940 | 50-1,000,000 | 4.3 |

The lower detection limit (LDL) is defined as the concentration which would have a 95% probability of generating at least one positive well. The upper limit of quantification (ULQ) is defined as the concentration where the probability of all wells being positive is 5%. DR: dynamic range. Calculations were performed according to the equations and algorithms found in Kreutz J E, Munson T, Huynh T, Shen F, Du W, Ismagilov R F. "Theoretical design and analysis of multivolume digital assays with wide dynamic range validated experimentally with microfluidic digital PCR." Anal Chem. 2011 83(21):8158-68.

SlipChip Device Fabrication.

The procedure for fabricating the multivolume rotational SlipChip and two-step SlipChip devices was based on previous work (see Du, W. B., Li, L., Nichols, K. P. and Ismagilov, R. F. Slipchip. Lab Chip 2009 9, 2286-2292). The device features were etched to a depth of ~100 µm for the multivolume rotational SlipChip devices and ~67 µm for the two-step SlipChip devices. After etching and drilling access holes, both devices were subjected to the same glass silanization process, previously described (see, e.g., Shen, F., Sun, B., Kreutz, J. E., Davydova, E. K., Du, W. B., Reddy, P. L., Joseph, L. J. and Ismagilov, R. F. Multiplexed Quantification of Nucleic Acids with Large Dynamic Range Using Multivolume Digital RTPCR on a Rotational Slipchip Tested with HIV and Hepatitis C Viral Load. J. Am. Chem. Soc. 2011 133, 17705-17712.), where the glass plates were first thoroughly cleaned with piranha mix and dried sequentially with 200 proof ethanol and nitrogen gas, and then oxidized in a plasma cleaner for 2 min and immediately transferred into a vacuum desiccator for 1.5 h for silanization with dimethyldichlorosilane. After silanization, the devices were rinsed thoroughly with chloroform, acetone, and ethanol, and dried with nitrogen gas before use. When a glass SlipChip device needed to be reused, it was first cleaned with acid Piranha Solution and then subjected to the same silanization and rinsing procedure described above.

Assembling and Loading SlipChips.

The SlipChips used for both the dLAMP and the dRT-LAMP reactions were assembled under degassed oil (mineral oil: tetradecane 1:4 v/v). Both top and bottom plates were immersed in the oil phase and placed face to face. The two plates were aligned under a stereoscope (Leica, Germany) and stabilized using binder clips. Through-holes were drilled into the top plate to serve as fluid inlets and oil outlets in dead-end filling. The reagent solutions were loaded through the inlets by pipetting.

HCV Viral RNA Purification from AcroMetrix® HCV High Control.

200 µL plasma containing HCV RNA (viral load estimate provided by the company: 1.1 IU/mL-3.5 IU/mL) was extracted using the QIAamp Viral RNA Mini Kit (QIAGEN Inc, Valencia, Calif., USA) according to the manufacturer's instructions. The elution volume was 60 µL. The purified HCV viral RNA was analyzed immediately or stored at −80° C. until further analysis.

Preparation of EBT Solution.

The EBT stock solutions were prepared by dissolving EBT dye in deionized water. The aqueous solution was sonicated for 10-20 min and the free volume was filled with argon gas and mixed on a rotator at 65° C. for 1 h. To remove any potential impurities from the EBT dye, Chelex® 100 ion exchange resin was added to the resulting solution (5% w/v) and placed on rotator for 1 h. Resin was centrifuged at 3,000 rpm for 5 min and the top fraction was collected in a Falcon tube, flushed with argon and stored at room temperature for no more than 2 days. A comparison of EBT, HNB and calmagite indicator dye stock solutions before and after treatment with Chelex® 100 is provided in FIG. 20.

Storage Stability of Amplification Indicator Dyes by Drying in the Presence of Stabilizer Trehalose.

EBT, HNB and calmagite stock solutions at 0.7 mM were prepared by dissolving the dyes in 20 mM Tris-HCl buffer (pH 8.8) and adding 30 mM of trehalose. The solutions were sonicated for 10 min and mixed on a rotator at room temperature for 1 h. Chelex® 100 ion exchange resin was added (5% w/v) and placed on rotator for 1 h. Resin was centrifuged at 3,000 rpm for 5 min and the top fraction was collected in a Falcon tube. The resulting stock solutions were transferred to a Costar™ Clear Polystyrene 96-Well Plate (40 µL per well) and sealed with Corning® Universal Optical Microplate Sealing Tape before spectrophotometric analysis (time 0 h). Immediately after analysis, the sealing cover was removed and the plate was placed in a desiccator under vacuum overnight until the dye stock solutions were completely dry. Then, at 24-hour time points over the next 120 h (for a total of 5 time points), three wells of each dried amplification indicator solution were resuspended with 40 µL of deionized water and spectrophotometric analyses were performed. After each measurement, the plate was sealed again (to prevent hydration of the dried solutions in the other wells) and kept in the dark at room temperature. The absorption spectra analyses were performed by using the POLARstar Omega microplate reader with Omega Data analysis software. Absorbance in the range of 400-700 nm was recorded at 2-nm intervals. Blank solutions (20 mM Tris-HCl buffer with 30 mM Trehalose) were also loaded at time 0 h, desiccated after the first measurement, and treated as the rest of the solutions. The measured spectral absorbance from these control solutions was subtracted at each time point from the plotted data (FIG. 5).

RT-LAMP Amplification of HCV RNA in-Tube.

The purified HCV RNA described above was used for in-tube RT-LAMP amplification. The RT-LAMP mix contained the following: 20 µL of RM, 2 µL of EM, 2 µL of SYTO® 9 Stain from a 40 µM stock, 4 µL of LAMP primer mixture (20 µM BIP/FIP, 10 µM LB/LF, and 2.5 µM B3/F3; see Table 5), 1 µL of SUPERase In RNase Inhibitor (20 U/L), EBT solutions of various concentrations and with various amounts of RNA template solution, and enough nuclease-free water to bring the volume to 40 The solution was loaded into 0.2 mL PCR tubes and heated at 63° C. for 50 min and 85° C. for 5 min (heat inactivation) on an Eppendorf Mastercycler Gradient PCR Themal Cycler.

TABLE 5

Sequence of primers used in RT-LAMP experiments for detection of hepatitis c RNA: F3 (SEQ ID NO: 1), FTP (SEQ ID NO: 2), LF (SEQ ID NO: 3), B3 (SEQ ID NO: 4), BIP (SEQ ID NO: 5) and LB (SEQ ID NO: 6). I = inosine.

| primer | sequence (5'-3') |
|---|---|
| F3 | CCTCCCGGGAGAGCCATAG |
| FIP | TCCAAGAAAGGACCCIGTCTTTTTCTGCGGAACCGGTGAGTAC |
| LF | TTICCGGIAATTCCGGT |
| B3 | GCACTCGCAAGCACCITATC |
| BIP | TTGGGCGTGCCCCCGCIAGATTTTTCAGTACCACAAGGCCITTCGCIACC |
| LB | CTGCTAGCCGAGTAGIGTTG |

Spectrophotometric Analysis for Positive and Negative RT-LAMP Reactions.

Fifty-μL of positive and negative RT-LAMP reaction solutions containing 0.7 mM of EBT, HNB and calmagite dyes were transferred to a Costar™ Clear Polystyrene 96-Well Plates, the plate was sealed with a Corning® Universal Optical Microplate Sealing Tape and then used for spectrophotometric analysis. An absorption spectra analysis was performed by using the POLARstar Omega microplate reader with Omega Data analysis software. The instrument was first set to zero at 700 nm for distilled water, and absorbance in the range of 400 nm to 700 nm was recorded at 2-nm intervals. Transmittance was calculated from absorbance values using the following equation: T=10(2−A).

Prediction of RGB Values.

Predicted RGB values for a positive and negative LAMP amplification reaction containing EBT were calculated as follows: (i) The spectral response curves for a Exmor R CMOS image sensor were available only in a graphical format, so data was extracted using Plot Digitizer (ver. 2.6.6) and new plots were generated. (ii) The area under the curve for each of the three color channel spectra was normalized (selecting 1,000 arbitrary values under each curve). Uniform white-balanced light source was assumed. (iii) Convolution of the spectral transmittance spectral profiles of the indicator dye for a positive and a negative LAMP reaction solution (experimentally obtained) with the normalized spectral responses from the Exmor R CMOS image sensor was performed. We ignored the light scattering caused by pyrophosphate release during the amplification reaction. As a result, six curves were generated (a positive and negative for each of the three color channels). (iv) The area under each curve was calculated and its square root taken, providing the predicted RGB values for positive and negative RT-LAMP reaction solutions in the presence of EBT at this particular concentration.

dLAMP Amplification of Phage Lambda DNA on Multivolume Rotational SlipChip Devices.

To amplify lambda phage DNA using dLAMP method, the LAMP mix contained the following: 20 μL of RM, 2 μL of EM, 2 μL of SYTO® 9 Stain from 40 μM stock, 4 μL of primer mixture (20 μM BIP/FIP, 10 μM LB/LF, and 2.5 μM B3/F3; see Table 6), 2 μL of BSA (20 mg/mL), various amounts of DNA template solution, 4.7 μL of 6 mM EBT dye (0.7 mM final concentration) and enough nuclease-free water to bring the volume to 40 μL. The solution was loaded onto a multivolume rotational SlipChip device and heated at 63° C. for 50 min on flat block PCR machine (Eppendorf Mastercycler). Five minutes of heating at 85° C. was used to stop the reaction.

TABLE 6

Sequence of primers used in LAMP experiments for detection of phage lambda DNA: F3 (SEQ ID NO: 7), FIP (SEQ ID NO: 8), LF (SEQ ID NO: 9), B3 (SEQ ID NO: 10), BIP (SEQ ID NO: 11) and LB (SEQ ID NO: 12). I = inosine.

| primer | sequence (5'-3') |
|---|---|
| F3 | GAATGCCCGTTCTGCGAG |
| FIP | CAGCATCCCTTTCGGCATACCAGGTGGCAAGGGTAATGAGG |
| LF | GGCGGCAGAGTCATAAAGCA |
| B3 | TTCAGTTCCTGTGCGTCG |
| BIP | GGAGGTTGAAGAACTGCGGCAGTCGATGGCGTTCGTACTC |
| LB | GGCAGATCTCCAGCCAGGAACTA |

Real-Time dRT-LAMP of HCV RNA on Two-Step SlipChip Devices.

To amplify HCV viral RNA using dRT-LAMP method on house-built real-time instrument, the RT-LAMP mix contained the following: 20 μL of RM, 2 μL of EM, 2 μL of SYTO® 9 Stain from 40 μM stock, 4 μL of primer mixture (20 μM BIP/FIP, 10 μM LB/LF, and 2.5 B3/F3; see Table 5), 2 μL of BSA (20 mg/mL), 1 μL of SUPERase In RNAase inhibitor, various amounts of RNA template solution, and enough nuclease-free water to bring the volume to 40 μL. The solution was loaded into the 5 nL wells of two-step SlipChip devices. Other set of wells (9.5 nL) were loaded with 2.4 mM solution of EBT solution (1.57 mM final concentration). SlipChips were heated at 63° C. for 50 min on a house-built real-time instrument; reactions were stopped by heating to 85° C. for 5 min.

House-Built Real-Time Instrument Imaging.

Experiments were performed on a Bio-Rad PTC-200 thermocycler with a custom machined block. The block contains a flat 3"×3" portion onto which the devices are placed ensuring optimal thermal contact. The excitation light source used was a Philips Luxeon S (LXS8-PW30) 1315 lumen LED module with a Semrock filter (FF02-475). Image acquisition was performed with a VX-29MG camera and a Zeiss Macro Planar T F2-100 mm lens. A Semrock filter (FF01-540) was used as an emission filter. Images acquired were analyzed using Lab VIEW software.

House-Built Real-Time Instrument Data Analysis.

Fluorescent images were analyzed using self-developed Labview software. The data were analyzed by first creating a binary mask that defined the location of each reaction volume within the image. The masked spots were then overlaid on the stack of images collected over the course of the experiment and the average intensity of each individual masked spot was tracked over the course of the stack. Background subtraction of the real-time trace was performed by creating a least mean square fit of each individual trace. Threshold was then manually set at the half height of the averaged maximum intensity, and the time-to-positive of each reaction was then determined as the point at which the real-time curve crossed the defined threshold.

Bright-Field Image Acquisition.

A mobile phone was used to capture the readout under standard fluorescent light, using the camera's default autofocus and autoexposure settings. Photographs of the 96-well plate were also taken using alternate commercial cell phones and under different lighting conditions (FIG. 6 and FIG. 9). Stereoscope imaging was done using Leica MZ Fl III stereoscope with a PLAN 0.5× lens. The stereoscope was equipped with a Diagnostic Instruments color mosaic model 11.2 megapixel camera and images were acquired using Spot imaging software. An automatic white-balance adjustment was done for each image using Spot software. Multiple images were acquired to capture all wells in the device, and assembled to form a complete image of the device to compare with the image acquired from the cell phone camera by using the freeware Image Composite Editor (ver. 2.0).

Bright Field Image Processing and Data Analysis.

Images acquired with cell phone and stereoscope were processed using open source Image J software (ver.1.49) according to the standard procedure. Briefly: (i) white balance was corrected as needed, (ii) color channels of the original image were split and, (iii) one channel was divided by a second channel (e.g., green channel divided by the red channel in the G/R approach) to derive a ratiometric image; and (iv), automatic thresholding was applied to make a binary (black and white) image. Semi-automatic counting on the two-step Slipchip images was accomplished using a freeware Fiji image processing. Acquired bright field images for the multivolume rotational SlipChips were counted manually.

7.2 Example 2

Enhanced Visual Detection of Lambda DNA Amplification by LAMP Based on Hydroxynaphthol Blue and Image Processing.

To amplify phage lambda DNA using LAMP method in the presence of hydroxynaphthol blue (one-pot amplification reaction), the LAMP mix solution contained: 10× in-house LAMP reaction mix (Tris-HCl 200 mM pH 8.8, KCl 100 mM, MgSO4 80 mM, (NH4)2SO4 100 mM, 1% Tween20), Betaine, Bst 2.0 WarmStart DNA Polymerase, Bovine Serum Albumin, Deoxynucleotide Solution Mix, 10× primer mixture (20 µM BIP/FIP, 10 µM LB/LF, and 2.5 µM B3/F3; see Table 6), purified phage lambda DNA template solution, hydroxynaphthol blue solution at 0.3 mM final concentration, and nuclease-free water. Positive and negative solution were loaded into a 3D-printed amplification module (10 µL well) and incubated in an oven at 63° C. for 40 min. An unmodified cell phone camera was used to capture the readout immediately after amplification under standard fluorescent light, using the camera's default autofocus and autoexposure settings. Acquired image was processed using open source Image J software.

FIG. 21 shows color images obtained from the experiment. Images in the top panels show that positive wells turn blue (left), while the negative wells remain purple after amplification (right). Bottom panels show images from the image processing that increases the contrast between the two conditions. Positive wells are dark (left) while the negative wells are not distinguishable from the background (right).

7.3 Example 3

Enhanced Visual Detection of HCV RNA Amplification by RT-LAMP Based on Eriochrome Black T and Image Processing.

To amplify HCV RNA using RT-LAMP method in the presence of eriochrome black T (one-pot amplification reaction), the RT-LAMP mix solution contained: 10× in-house LAMP reaction mix (Tris-HCl 200 mM pH 8.8, KCl 100 mM, MgSO4 80 mM, (NH4)2SO4 100 mM, 1% Tween20), Betaine, Bst 2.0 WarmStart DNA Polymerase, AMV Reverse Transcriptase polymerase, Bovine Serum Albumin, Deoxynucleotide Solution Mix, 10×HCV RT-LAMP primer mixture (20 µM BIP/FIP, 10 µM LB/LF, and 2.5 µM B3/F3; see Table 5), purified HCV RNA template solution, eriochrome black T solution at 0.3 mM final concentration, and nuclease-free water. Positive and negative solution were loaded into a 3D-printed amplification module (10 µL well) and incubated in an oven at 63° C. for 40 min. An unmodified cell phone camera was used to capture the readout immediately after amplification under standard fluorescent light, using the camera's default autofocus and autoexposure settings. Acquired image was processed using open source Image J software.

Images from the experiment are provided as FIG. 22. The image on the left is an original color image from RT-LAMP amplification of HCV RNA in the presence of Ericochrome Black T. In the picture, positive wells are blue and negative wells are purple. The difference between positive and negative wells was enhanced by image processing, splitting the color channels and performing the ratio of green value over red value for each pixel. The result of this operation is shown in the right picture, in which the positive wells show a stronger signal than the negative wells. This experiment was performed with HCV RNA as the template.

7.4 Example 4

Absorbance Spectrum for LAMP Solutions Containing Eriochrome Black T: One-Pot Phage Lambda DNA Amplified by the LAMP Method in the Presence of 0.3 mM Eriochrome Black T Solution.

To amplify phage lambda DNA using LAMP method in the presence of eriochrome black T (one-pot amplification reaction), the LAMP mix solution contained: 10× in-house LAMP reaction mix (Tris-HCl 200 mM pH 8.8, KCl 100 mM, MgSO4 80 mM, (NH4)2SO4 100 mM, 1% Tween20), Betaine, Bst 2.0 WarmStart® DNA Polymerase, Bovine Serum Albumin, Deoxynucleotide Solution Mix, 10× lambda LAMP primer mixture (20 µM BIP/FIP, 10 µM LB/LF, and 2.5 µM B3/F3; see Table 6), purified phage lambda DNA solution, eriochrome black T solution at 0.6 mM final concentration, and nuclease-free water. Positive and negative solution were loaded into 0.2 mL Eppendorf tubes and heated at 63° C. for 50 min and 85° C. for 5 min (heat inactivation) on an Eppendorf Mastercycler Gradient PCR Themal Cycler. Fifty-µL of positive and negative LAMP reaction solutions containing 0.6 mM of eriochrome black T dye were transferred to a Costar™ Clear Polystyrene 96-Well Plates, the plate was sealed with a Corning® Universal Optical Microplate Sealing Tape and then used for spectrophotometric analysis. An absorption spectra analysis was performed by using the POLARstar Omega microplate reader with Omega Data analysis software. The instrument was first set to zero at 700 nm for distilled water, and absorbance in the range of 700 nm to 400 nm was recorded at 2-nm intervals. Amplification indicator solutions were prepared by dissolving each dye in deionized water. The aqueous solutions were sonicated for 10-20 min and the free volume was filled with argon gas and mixed on a rotator at 65° C. for 1 h.

Data from the absorption spectra analysis are provided in FIG. 23. The blue line shows a negative control without amplification, while the red line is the spectrum for a positive sample with amplification. The ratio of absorbance at 540 nm and 650 nm can be used to detect amplification, as it changes from 1.33 to 1.03 when amplification occurs.

7.5 Example 5

Absorbance Spectrum for RT-LAMP Solution Containing Three Different Amplification Indicators: One-Pot HCV RNA Amplified by RT-LAMP Method in the Presence of 0.7 mM Eriochrome Black T, Hydroxynaphthol Blue and Calmagite To amplify phage HCV RNA using RT-LAMP method in the presence of three different amplification indicators (one-pot amplification reaction for eriochrome Black T, hydroxynaphthol blue and calmagite), the RT-LAMP mix solution (Loopamp® RNA amplification kit) contained: 2× Reaction Mix (RM) (40 mM Tris-HCl pH 8.8, 20 mM KCl, 16 mM MgSO4, 20 mM (NH4)2SO4, 0.2% Tween20, 1.6 M Betaine and dNTPs 2.8 mM each), Enzyme Mix (EM) (mixture of Bst DNA polymerase and AMV reverse transcriptase), 10×HCV RT-LAMP primer mixture (20 µM BIP/FIP, 10 µM LB/LF, and 2.5 µM B3/F3; see Table 5), amplification indicators (eriochrome Black T, hydroxynaphthol blue and calmagite) at 0.7 mM final concentration, purified HCV RNA template solution and distilled water. The solutions were loaded into 0.2 mL Eppendorf tubes and heated at 63° C. for 50 min and 85° C. for 5 min (heat inactivation) on an Eppendorf Mastercycler Gradient PCR Themal Cycler. Fifty-µL of positive and negative RT-LAMP reaction solutions containing 0.7 mM of each dye were transferred to a Costar™ Clear Polystyrene 96-Well Plates, the plate was sealed with a Corning® Universal Optical Microplate Sealing Tape and then used for spectrophotometric analysis. An absorption spectra analysis was performed by using the POLARstar Omega microplate reader with Omega Data analysis software. The instrument was first set to zero at 700 nm for distilled water, and absorbance in the range of 700 nm to 400 nm was recorded at 2-nm intervals. Amplification indicator solutions were prepared by dissolving each dye in deionized water. The aqueous solutions were sonicated for 10-20 min and the free volume was filled with argon gas and mixed on a rotator at 65° C. for 1 h. Chelex-100 ion exchange resin was added to the resulting solution (5% w/v of) and placed on rotator for 1 h. Resin was centrifuged at 3,000 rpm for 5 min and the top fraction was collected in a Falcon tube, flushed with argon and stored at room temperature for no more than 2 days.

Figure 24:
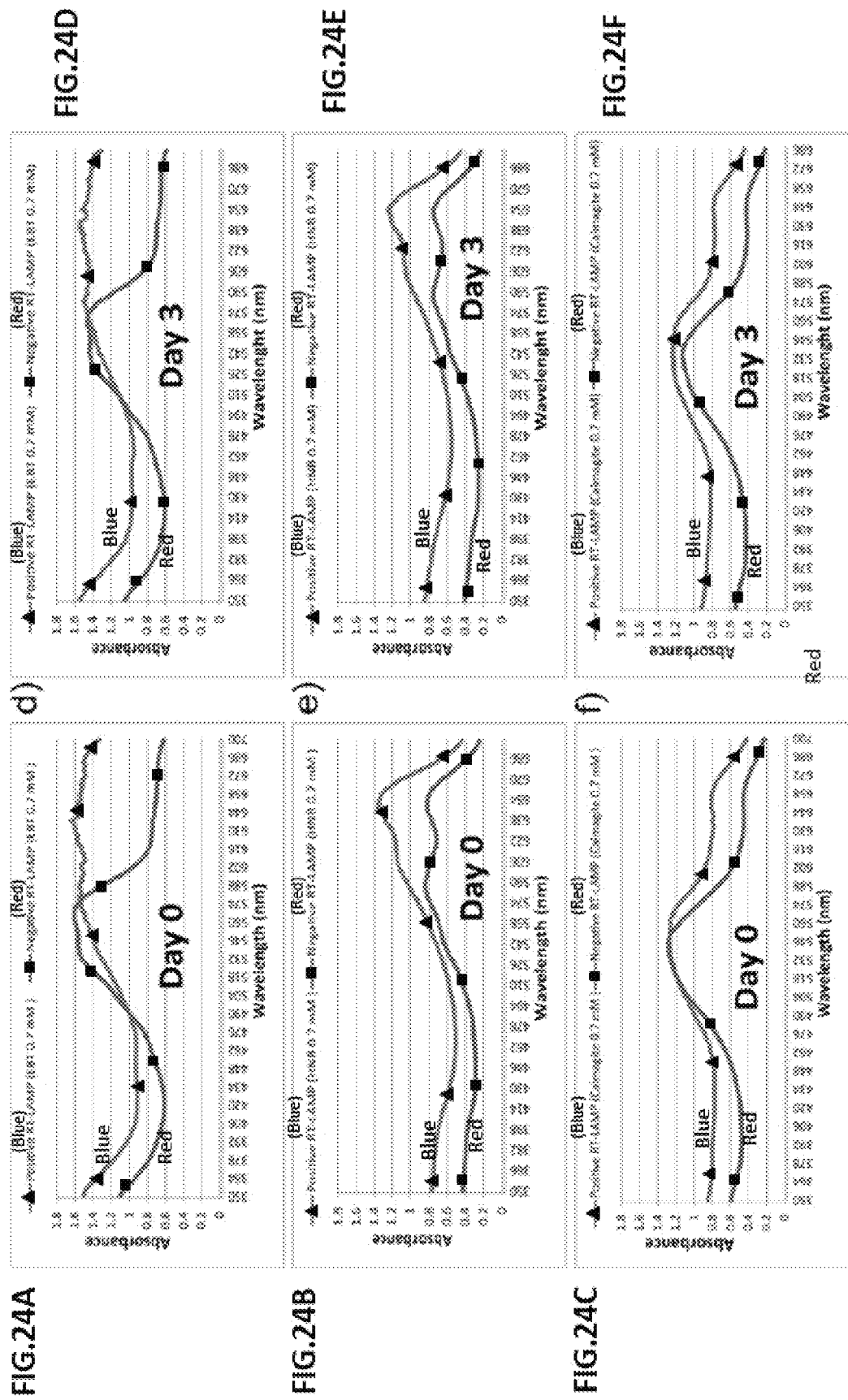

FIG. 24 provides measured spectral absorbance over the wavelength range of visible light (400-700 nm) for positive (solid blue line with solid triangles) and negative (solid red line with solid rectangles) RT-LAMP reaction solutions, each containing 0.7 mM of each amplification indicator: (A and D) Eriochrome Black T; (B and E) hydroxynaphthol blue; (C and F) calmagite. Absorbance spectrum of A, B and C were measured right after amplification reaction was performed (day 0) while D, E and F were measured 72 hours after (day 3).

7.6 Example 6

One-Step Method for Digital Visual Readout: Visual Detection and Enhancement of Single Phage Lambda DNA Molecules Amplified by LAMP Method in the Presence of 0.7 mM Eriochrome Black T, Images Acquired with Stereoscope.

All techniques for visual readout and image processing can be used for detection of amplification in digital-single molecule platforms, such as SlipChip Devices. In this example we used image processing to increase signal contrast for a digital-single molecule experiment in a multivolume SlipChip device using eriochrome black T as visual readout indicator. The FIG. 25 provides an original image of the SlipChip device on the left, with positive wells (blue, labeled "B") and negative wells (purple, not labeled). After image processing by splitting the color channels and dividing the green channel by the red channel, the resulting image is shown on the right of the FIG. 25. The positive wells are clearly detectable as white, while the negative wells look dark.

Experimental Details

To amplify phage lambda DNA using LAMP method in the presence of eriochrome black T (one-pot amplification reaction), the LAMP mix solution was prepared as follow: 10 µL of reaction mix (Tris-HCl 200 mM pH 8.8, KCl 100 mM, MgSO4 80 mM, (NH4)2SO4 100 mM, Tween20 1%), 16 µL of Betaine (5M stock), 5 µL of Bst 2.0 WarmStart® DNA Polymerase (8,000 units/mL), 5 µL of Bovine Serum Albumin (20 mg/mL), 14 µL of Deoxynucleotide Solution Mix (10 mM each nt), 10 µL of LAMP primer mixture (20 µM BIP/FIP, 10 µM LB/LF, and 2.5 µM B3/F3; Table 6), 10 µL of DNA phage lambda (100 genomic copies per µL), 14 µL of Eriochrome black T solution (5 mM stock, final concentration of eriochrome black t was 0.7 mM), and enough nuclease-free water to bring the volume to 100 µL. The solution was loaded into multivolume SlipChip microfluidic device (Jason E. Kreutz, Todd Munson, Toan Huynh, Feng Shen, Wenbin Du, and Rustem F. Ismagilov, "Theoretical Design and Analysis of Multivolume Digital Assays with Wide Dynamic Range Validated Experimentally with Microfluidic Digital PCR," Analytical Chemistry 2011 83: 8158-8168) and heated at 63° C. for 50 min and 85° C. for 5 min (heat inactivation) on an Eppendorf Mastercycler Gradient PCR Themal Cycler. Stereoscope imaging was done using Leica MZ Fl III stereoscope with a PLAN 0.5× lens. The stereoscope was equipped with a Diagnostic Instruments color mosaic model 11.2 megapixel camera and images were acquired using Spot imaging software. An automatic white-balance adjustment was done for each image using Spot software. Multiple images were acquired to capture all wells in the device, and assembled to form a complete image of the device to compare with the image acquired from the cell phone camera by using the freeware Image Composite Editor 2.0 (Microsoft Research 2014). Images acquired with stereoscope were processed using open source Image J software. Briefly: (i) white balance was corrected as needed, (ii) color channels of the original image were split and, (iii) one channel was divided by a second channel (e.g., green channel divided by the red channel in the G/R approach) to derive a ratiometric image. In this case, the green channel was divided by the red channel. The eriochrome black T stock solutions were prepared by dissolving eriochrome black T dye in deionized water. The aqueous solution was sonicated for 10-20 min and the free volume was filled with argon gas and mixed on a rotator at 65° C. for 1 h.

7.7 Example 7

One-Step Method for Digital Visual Readout: Visual Detection and Enhancement by Image Processing of Single Phage Lambda DNA Molecules Amplified by LAMP Method in the Presence of 0.7 mM Eriochrome Black T, Images Acquired with Unmodified Cell Phone Camera.

In this example we used image processing to increase signal contrast for a digital single-molecule amplification experiment in a multivolume rotational SlipChip device (modified from Jason E. Kreutz, Todd Munson, Toan Huynh, Feng Shen, Wenbin Du, and Rustem F. Ismagilov, "Theoretical Design and Analysis of Multivolume Digital Assays with Wide Dynamic Range Validated Experimentally with Microfluidic Digital PCR," Analytical Chemistry 2011 83: 8158-8168) using eriochrome black T as amplification indicator and an unmodified cell phone to acquire images. FIG. 26A shows the original raw cell phone image, with positive wells (blue) and negative wells (purple). FIG. 26B shows the result after image processing by splitting the color channels and dividing the green channel by the red channel. The positive wells are clearly detectable as white, while the negative wells look dark. Finally, the image is converted to B/W (binarized) image by using thresholding adjustment and provided in FIG. 26C. These devices contained 1,240 wells of eight volumes ranging from 15 nL to 50 nL.

Experimental Details

To amplify lambda DNA using LAMP method in the presence of eriochrome black T (one-pot amplification reaction), the LAMP mix solution was prepared as follows: 20 µL of RM, 2 µL of EM, 2 µL of SYTO® 9 Stain from a 40 µM stock, 4 µL of lambda LAMP primer mixture (20 µM BIP/FIP, 10 µM LB/LF, and 2.5 µM B3/F3; see Table 6), 5.6 µL of Eriochrome black T solution (5 mM stock, final concentration of eriochrome black t was 0.7 mM), purified lambda DNA sample and enough nuclease-free water to bring the volume to 40 µL. The solution was loaded into multivolume rotational SlipChip microfluidic device similar to Jason E. Kreutz, Todd Munson, Toan Huynh, Feng Shen, Wenbin Du, and Rustem F. Ismagilov, "Theoretical Design and Analysis of Multivolume Digital Assays with Wide Dynamic Range Validated Experimentally with Microfluidic Digital PCR," Analytical Chemistry 2011 83: 8158-8168 and heated at 63° C. for 50 min and 85° C. for 5 min (heat inactivation) on an Eppendorf Mastercycler Gradient PCR Themal Cycler. The image was acquired by a cell phone camera. Images acquired with cellphone were processed using open source Image J software. Briefly: (i) white balance was corrected as needed, (ii) color channels of the original image were split and, (iii) one channel was divided by a second channel (e.g., green channel divided by the red channel in the G/R approach) to derive a ratiometric image, (iv) image was binarized by thresholding. In this case, the green channel was divided by the red channel. The eriochrome black T stock solutions were prepared by dissolving eriochrome black T dye in deionized water. The aqueous solution was sonicated for 10-20 min and the free volume was filled with argon gas and mixed on a rotator at 65° C. for 1 h, Chelex-100 ion exchange resin was added to the resulting solution (5% w/v of) and placed on rotator for 1 h. Resin was centrifuged at 3,000 rpm for 5 min and the top fraction was collected in a Falcon tube, flushed with argon and stored at room temperature for no more than 2 days.

7.8 Example 8

One-Pot Method for Digital Visual Readout in 27 nL Well Device: Visual Detection, Enhancement by Image Processing and Comparison with Fluorescent Detection of Single Phage Lambda DNA Molecules Amplified by LAMP Method in the Presence of 0.7 mM Eriochrome Black T, Images Acquired with Stereoscope.

In this example we used one-pot method to visualize digital-single molecule amplification reactions in a 27 nL wells using fluorescence contrast and bright field contrast. SYTO 60® was used for fluorescence and eriochrome black T solution was used as a amplification indicator for visual readout. FIG. 27A shows the fluorescence image (SYTO 60®) acquired with house-built real-time instrument, where positive wells are bright and negative wells are dark. FIG. 27B shows an image of the same area captured with the stereoscope, where positive wells are blue and negative wells are purple. FIG. 27C shows the result after image processing, by splitting the color channels and then dividing the green channel by the red channel. Here, the negative wells look dark and positive wells are similar to the background.

Experimental Details

To amplify phage lambda DNA using LAMP method in the presence of eriochrome black T (one-pot amplification reaction), the LAMP mix solution was prepared as follow: 10 µL of reaction mix (Tris-HCl 200 mM pH 8.8, KCl 100 mM, MgSO4 80 mM, (NH4)2SO4 100 mM, 1% Tween20), 16 µL of Betaine (5M stock), 5 µL of Bst 2.0 WarmStart® DNA Polymerase (8,000 units/mL), 5 µL of Bovine Serum Albumin (20 mg/mL), 14 µL of Deoxynucleotide Solution Mix (10 mM each nt), 10 µL of 10× lambda LAMP primer mixture (20 µM BIP/FIP, 10 µM LB/LF, and 2.5 µM B3/F3; see Table 6), 10 µL of DNA phage lambda (100 genomic copies per 10 µL of SYTO® 60 red fluorescent nucleic acid stain (20 µM stock), 14 µL of Eriochrome black T solution (5 mM stock, final concentration of eriochrome black t was 0.7 mM), and enough nuclease-free water to bring the volume to 100 µL. The amplification solution containing the amplification indicator dye (and fluorescent dye) was loaded into SlipChip microfluidic device (Feng Shen, Elena K. Davydova, Wenbin Du, Jason E. Kreutz, Olaf Piepenburg, and Rustem F. Ismagilov, "Digital Isothermal Quantification of Nucleic Acids via Simultaneous Chemical Initiation of Recombinase Polymerase Amplification Reactions on SlipChip," Analytical Chemistry 2011 83:3533-3540), two sets of 10 nL and 17 nL wells were loaded from both sides of the SlipChip and the device slipped to combine both sets into 800 wells of 27 nL volume each.

The device was heated at 63° C. for 50 min and 85° C. for 5 min (heat inactivation) on a house-built real-time instrument and fluorescence image was acquired. Stereoscope imaging was done using Leica MZ Fl III stereoscope with a PLAN 0.5× lens. The stereoscope was equipped with a diagnostic Instruments color mosaic model 11.2 megapixel camera and images were acquired using Spot imaging software. An automatic white-balance adjustment was done for each image using Spot software. Images acquired with stereoscope were processed using open source Image J software.

The image processing was done by the following steps: (i) color channels of the original image were split and, (ii) one channel was divided by a second channel (e.g., green channel divided by the red channel in the G/R approach) to derive a ratiometric image. In this case, the green channel was divided by the red channel. The eriochrome black T stock solutions were prepared by dissolving eriochrome black T dye in deionized water. The aqueous solution was sonicated for 10-20 min and the free volume was filled with argon gas and mixed on a rotator at 65° C. for 1 h.

7.9 Example 9

Two-Step Method for Digital Visual Readout in Amplification Reactions Performed in 17 nL Wells: Visual Detection with an Unmodified Cell Phone Camera, Automatic Single-Molecule Counting and Comparison with Fluorescent Detection and Quantification of Single Phage Lambda DNA Molecules Amplified by LAMP Method.

In this example we used two-step method to visualize digital-single molecule amplification reactions ran in 17 nL wells using fluorescence contrast (achieved by calcein fluorescence) and bright field contrast (achieved by using eriochrome black T solution as amplification indicator). First, we performed digital isothermal amplification in the large set amplification wells in the absence of the imaging dye (17 nL wells). After amplification, a "slip" was performed and the amplification wells came into contact with a second set smaller wells (10 nL), which contained the indicator dye—for a total well volume of 27 nL. Images were acquired immediately after mixing both set of wells. FIG. 28A shows the fluorescence image acquired using house-built real-time instrument where positive wells are bright and negative wells are dark. FIG. 28B shows image of the same area acquired with an unmodified cell phone camera (Apple iPhone 4S) where positive wells are blue (with a dot) and negative wells are purple (without a dot). FIG. 28C provides a plot showing the correlation between fluorescent and bright field single-molecule counts acquired by fluorescence microscopy and unmodified cell phone (after image processing), respectively. Single-molecule counting was automatically performed for both approaches. Counts obtained by a house-built real-time imaging instrument (to read fluorescence), and counts obtained by G/R processing from an image captured by an unmodified cell phone camera were significantly correlated (Correlation=0.9834).

Experimental Details

To amplify phage lambda DNA using LAMP method the mix solution (Loopamp® RNA amplification kit) contained: 2× Reaction Mix (RM) (40 mM Tris-HCl pH 8.8, 20 mM KCl, 16 mM MgSO4, 20 mM (NH4)2SO4, 0.2% Tween20, 1.6 M Betaine and dNTPs 2.8 mM each), Enzyme Mix (EM) (mixture of Bst DNA polymerase and AMV reverse transcriptase), 10× phage lambda LAMP primer mixture (20 µM BIP/FIP, 10 µM LB/LF, and 2.5 µM B3/F3; see Table 6), purified phage lambda DNA template solution and distilled water. Amplification indicator was previously prepared as follows: the eriochrome black T stock solutions were prepared by dissolving eriochrome black T dye in deionized water. The aqueous solution was sonicated for 10-20 min and the free volume was filled with argon gas and mixed on a rotator at 65° C. for 1 h. Then, both solutions were loaded into two-step microfluidic SlipChip device (Feng Shen, Elena K. Davydova, Wenbin Du, Jason E. Kreutz, Olaf Piepenburg, and Rustem F. Ismagilov, "Digital Isothermal Quantification of Nucleic Acids via Simultaneous Chemical Initiation of Recombinase Polymerase Amplification Reactions on SlipChip," Analytical Chemistry 2011 83:3533-3540). LAMP reaction solution was loaded into large set of amplification wells in the absence of the imaging dye (17 nL wells), whereas amplification indicator (in this example eriochrome black T solution) was loaded into second set of smaller wells (10 nL wells). Then, the device was heated at 63° C. for 30 min and 85° C. for 5 min (heat inactivation) on an Eppendorf Mastercycler Gradient PCR Themal Cycler. After amplification was complete, a "slip" was performed and the amplification wells came into contact with a second set smaller wells (10 nL), which contained the indicator dye—for a total well volume of 27 nL. Fluorescent image was acquired on house-built real-time instrument and bright field image was acquired with an unmodified cell phone camera (Apple iPhone 4S).

7.10 Example 10

Two-Step Method for Digital Visual Readout in Amplification Reactions Performed in 5 nL Wells: Visual Detection with an Unmodified Cell Phone Camera, Automatic Single-Molecule Counting and Comparison with Fluorescent Detection of Single HCV RNA Molecules Amplified by RT-LAMP Method.

In this example we used one-pot method to visualize digital-single molecule amplification reactions in a 5 nL wells using fluorescence contrast and bright field contrast, SYTO 9® was used for fluorescence and eriochrome black T solution was used as a amplification indicator for visual readout. FIG. 29A shows the fluorescence image (SYTO 9®) acquired with house-built real-time instrument, where positive wells are bright and negative wells are dark. FIG. 29B provides an image of the same area captured with the stereoscope, where positive wells are blue (with a dot) and negative wells are purple (without a dot). FIG. 29C shows the result after image processing, by splitting the color channels and then dividing the green channel by the red channel. Here, the negative wells look dark and positive wells are similar to the background. In this example we used two-step method to visualize digital-single molecule amplification reactions in a 5 nL wells using fluorescence contrast achieved by SYTO 9® Green Fluorescent Nucleic Acid Stain and Eriochrome black T solution as a amplification indicator added by slipping 9.5 nL wells.

Experimental Details

To amplify HCV RNA using RT-LAMP method the LAMP mix solution was prepared as follows: 20 µL of RM, 2 µL of EM, 2 µL of SYTO® 9 Stain from a 40 µM stock, 4 µL of HCV LAMP primer mixture (20 µM BIP/FIP, 10 µM LB/LF, and 2.5 µM B3/F3; see Table 5), 1 µL of SUPERase In RNase Inhibitor (20 U/µL), purified HCV RNA sample and enough nuclease-free water to bring the volume to 40 µL. Amplification indicator was previously prepared as follows: the eriochrome black T stock solutions were prepared by dissolving eriochrome black T dye in deionized water. The aqueous solution was sonicated for 10-20 min and the free volume was filled with argon gas and mixed on a rotator at 65° C. for 1 h, Chelex-100 ion exchange resin was added to the resulting solution (5% w/v of) and placed on rotator for 1 h. Resin was centrifuged at 3,000 rpm for 5 min and the top fraction was collected in a Falcon tube, flushed with argon and stored at room temperature for no more than 2 days. Then, both solutions were loaded into two-step microfluidic SlipChip device based on the design published by Feng Shen, Elena K. Davydova, Wenbin Du, Jason E. Kreutz, Olaf Piepenburg, and Rustem F. Ismagilov, "Digital Isothermal Quantification of Nucleic Acids via Simultaneous Chemical Initiation of Recombinase Polymerase Amplification Reactions on SlipChip," Analytical Chemistry 2011 83:3533-3540. LAMP reaction solution was loaded into small set of wells in the absence of the indicator dye (5 nL wells), whereas amplification indicator (in this example eriochrome black T solution) was loaded into second set of larger wells (9.5 nL wells). Then, the device was heated at 63° C. for 30 min and 85° C. for 5 min (heat inactivation) on an Eppendorf Mastercycler Gradient PCR Themal Cycler. After amplification was complete, a "slip" was performed and the amplification wells came into contact with a second set smaller wells (10 nL), which contained the indicator dye (final concentration of 1.5 mM after mixing)—for a total well volume of 14.5 nL. Fluorescent image was acquired on house-built real-time instrument and bright field image was acquired with an unmodified cell phone camera (Apple iPhone 4S). Images acquired with cellphone were processed using open source Image J software. Briefly: (i) white balance was corrected as needed, (ii) color channels of the original image were split and, (iii) one channel was divided by a second channel (e.g., green channel divided by the red channel in the G/R approach) to derive a ratiometric image. In this case, the green channel was divided by the red channel.

7.11 Example 11

Two-Step Visual Detection of Phage Lambda DNA Based on LAMP Method and Hematoxylin-Based Amplification Indicator.

FIG. 30 provides an original image of two tubes with LAMP amplification reaction in the presence of hematoxylin-based amplification indicator. The left tube shows positive solution, in which reaction causes change color to yellow-green. Negative reaction on a right remains red. Phage lambda DNA detection was accomplished by using Hematoxylin-based solution described below, some metal ions were added for color enhancement.

Experimental Details

To amplify Lambda DNA using LAMP method the mix contained: 10× in-house LAMP reaction mix (Tris-HCl 200 mM pH 8.8, KCl 100 mM, MgSO4 80 mM, (NH4)2SO4 100 mM, 1% Tween20), Betaine, Bst 2.0 WarmStart DNA Polymerase, AMV Reverse Transcriptase polymerase, Bovine Serum Albumin, Deoxynucleotide Solution Mix, 10× Lambda LAMP primer mixture (20 µM BIP/FIP, 10 µM LB/LF, and 2.5 µM B3/F3; see Table 6), phage lambda DNA template solution, and nuclease-free water. The solution was loaded into 0.2 Eppedorf PCR tubes and heated at 63° C. for 30 min and 85° C. for 5 min (heat inactivation) on an Eppendorf Mastercycler Gradient PCR Themal Cycler. After amplification was completed, hematoxylin-based amplification indicator solution was added in 1:2 ratio to the tube with LAMP reaction mix (5 µL of this hematoxylin-based solution and 10 µL of LAMP reaction mix). Image was acquired with unmodified cell phone camera (Apple Iphone 4S). Hematoxylin-based amplification indicator solution was prepared according to following protocol: hemotoxilin, Isopropanol 96%, glycerol, potassium alum (KAl(SO4)2·12H2O), acetic anhydride ((CH3CO)2O), potassium iodate (KIO3), Cobalt(II) nitrate (Co(NO3)2), aluminium chloride (AlCl3), potassium permanganate (KMnO4), tris (2-carboxyethyl) phosphine (TCEP), hydroquinone and distilled water.

7.12 Example 12

Two-Step Digital Visual Detection of Phage Lambda DNA Based on LAMP Method and Hematoxylin-Based Amplification Indicator.

FIG. 31 (left) shows fluorescent digital pattern of a SlipChip device with LAMP amplification of phage lambda DNA in the presence of hematoxylin-based amplification indicator. FIG. 31 (right) shows bright field digital pattern of the same area. Colors were enhanced in bright field image for clarity.

Experimental Details

To amplify Lambda DNA using LAMP method the mix contained: the mix contained: 10× in-house LAMP reaction mix (Tris-HCl 200 mM pH 8.8, KCl 100 mM, MgSO4 80 mM, (NH4)2SO4 100 mM, 1% Tween20), Betaine, Bst 2.0 WarmStart DNA Polymerase, Bovine Serum Albumin, Deoxynucleotide Solution Mix, calcein, 10× lambda LAMP primer mixture (20 µM BIP/FIP, 10 µM LB/LF, and 2.5 µM B3/F3; see Table 6), phage lambda DNA template solution, and nuclease-free water. The solution was loaded into microfluidic SlipChip device (Feng Shen, Elena K. Davydova, Wenbin Du, Jason E. Kreutz, Olaf Piepenburg, and Rustem F. Ismagilov, "Digital Isothermal Quantification of Nucleic Acids via Simultaneous Chemical Initiation of Recombinase Polymerase Amplification Reactions on SlipChip," Analytical Chemistry 2011 83:3533-3540) and heated at 63° C. for 30 min and 85° C. for 5 min (heat inactivation) on an Eppendorf Mastercycler Gradient PCR Themal Cycler. The LAMP solution was loaded into the 6 nL wells and the hematoxylin-based amplification indicator solution was loaded into 3 nL wells (total volume after mixing was 9 nL). After amplification was completed, hematoxylin-based amplification indicator solution was mixed in 1:2 ratio wells containing LAMP reaction mix. Fluorescent image was acquired on house-built real-time instrument and bright field image was acquired with unmodified cell phone camera (Apple Iphone 4S). Hematoxylin-based amplification indicator solution contained (this protocol was modified from protocol described on example 10): hemotoxilin, ethanol, hydrogen peroxide (H2O2), potassium iodate (KIO3), Cobalt(II) nitrate (Co(NO3)2), aluminium chloride (AlCl3), potassium permanganate (KMnO4), tris (2-carboxyethyl) phosphine (TCEP), hydroquinone and distilled water. The solution was added in 1:2 ratio to the tube with LAMP reaction mix (5 µL of this hematoxylin-based solution and 10 µL of LAMP reaction mix) and heated at 63° C. for 30 min and 85° C. for 5 min (heat inactivation) on an Eppendorf Mastercycler Gradient PCR Themal Cycler.

7.13 Example 13

Two-Step Digital Visual Detection of Phage Lambda DNA Based on LAMP Method and Toluidine O-Based Amplification Indicator.

FIG. 32A is a fluorescent image of a SlipChip with LAMP amplification of phage lambda DNA in the presence of Toluidine O-based amplification indicator. This image was taken before slipping of the SlipChip device. FIG. 32B is a bright field digital pattern of the same area acquired with stereoscope after slipping and FIG. 32C is a callout from bright field image. Positive wells show bright florescence signal in FIG. 32A and clear precipitate on bright field contrast in FIGS. 32B and C.

Experimental Details

To amplify phage lambda DNA using LAMP method the mix solution (Loopamp® RNA amplification kit) contained: 2× Reaction Mix (RM) (40 mM Tris-HCl pH 8.8, 20 mM KCl, 16 mM MgSO4, 20 mM (NH4)2SO4, 0.2% Tween20, 1.6 M Betaine and dNTPs 2.8 mM each), Enzyme Mix (EM)

(mixture of Bst DNA polymerase and AMV reverse transcriptase), 10× phage lambda LAMP primer mixture (20 μM BIP/FIP, 10 LB/LF, and 2.5 μM B3/F3, see Table 6), purified phage lambda DNA template solution and distilled water. The solution was loaded into two-step microfluidic SlipChip device (Feng Shen, Wenbin Du, Elena K. Davydova, Mikhail A. Karymov, Janmajay Pandey, and Rustem F. Ismagilov, "Nanoliter Multiplex PCR Arrays on a SlipChip," Analytical Chemistry 2010 82:4606-4612) and heated at 63° C. for 50 min and 85° C. for 5 min (heat inactivation) on an Eppendorf Mastercycler Gradient PCR Themal Cycler. The LAMP solution was loaded into the 26 nL wells and the Toluidine 0-based amplification indicator solution was loaded into another set of 26 nL wells (total volume after mixing was 52 nL). After amplification was completed, Toluidine 0-based amplification indicator solution was mixed in 1:1 ratio wells containing LAMP reaction mix. Fluorescent image was acquired on house-built real-time instrument and bright field image was acquired with stereoscope. Toluidine 0-based amplification indicator solution contained 50 mM polyethylenimine (PEI) solution and 1 mg/mL of toluidine O in water.

7.14 Example 14

SlipChip Device.

Glass embodiments were made with standard photolithographic and wet chemical etching techniques. Soda-lime glass plates with chromium and photoresist coating were obtained from Telic Company (Valencia, Calif.). The glass plate with photoresist coating was aligned with a photomask containing the design of the microducts and areas using a Karl Suss, MJBB3 contact aligner. The photomask may also contain marks to align the mask with the plate. The glass plate and photomask were then exposed to UV light for 1 min. The photomask was removed, and the glass plate was developed by immersing it in 0.1 mol/L NaOH solution for 2 min. Only the areas of the photoresist that were exposed to the UV light dissolved in the solution. The exposed underlying chromium layer was removed using a chromium etchant (a solution of 0.6:0.365 M $HClO_4/(NH_4)_2Ce(NO_3)_6$). The plate was rinsed with Millipore water and dried with nitrogen gas, and the back of the glass plate was taped with PVC sealing tape (McMaster-Carr) to protect the back side of glass. The taped glass plate was then carefully immersed in a plastic container with a buffered etching agent composed of 1:0:0.75 mol/L $HF/NH_4F/HNO_3$ to etch the soda-lime glass at the temperature of 40° C. The etching speed was controlled by the etching temperature, and the area and duct depth was controlled by the etching time. After etching, the tape was removed from the plates. The plate was then thoroughly rinsed with Millipore water and dried with nitrogen gas. The remaining photoresist was removed by rinsing with ethanol, and the remaining chromium coating was removed by immersing the plate in the chromium etchant. The surface of the glass plate were rendered hydrophobic by silanization with tridecafluoro-1,1,2,2-tetrahydrooctyl-1-trichlorosilane (United Chemical Technologies, Inc.). Access holes were drilled with a 0.76 mm diameter diamond drill bit.

One method to establish fluidic communication between two or more areas of the SlipChip includes the use of a channel with at least one cross-sectional dimension in the nanometer range, a nanochannel, which can be embedded in the SlipChip. The nanochannels can be embedded into multilayer SlipChip. The height of nanochannel can be varied with nanometer scale resolution. The height of the nanochannedl can prohibit transfer of micron sized cells between the wells, but enable transfer of proteins, vesicles, micelles, genetic material, small molecules, ions, and other molecules and macromolecules, including cell culture media and secreted products. The width, length, and tortuosity of the nanochannels can also be manipulated in order to control transport dynamics between wells. Nanochannels can be fabricated as described in Bacterial metapopulations in nanofabricated landscapes, Juan E. Keymer, Peter Galajda, Cecilia Muldoon, Sungsu Park, and Robert H. Austin, PNAS Nov. 14, 2006 vol. 103 no. 46 17290-17295, or by etching nanochannels in the first glass piece and bringing it in contact with the second glass piece, optionally followed by a bonding step. Applications include filtration, capturing of cells and particles, long term cell culture, and controlling interactions among cells and cellular colonies and tissues.

SlipChip devices of the PDMS/Glass type was also made using soft lithography, similarly as described previously. The device used contains two layers, each layer was composed of a thin membrane of PDMS with ducts and areas, and a 1 mm thick microscope glass slides with size of 75 mm×25 mm. To make the device, the glass slides were cleaned and subjected to an oxygen plasma treatment. Dow-Corning Sylgard 184 A and B components were mixed at a mass ratio of 5:1, and poured onto the mold of the SlipChip. A glass slide was placed onto the PDMS before cure. A glass bottom with iron beads were place onto the glass slides to make the PDMS membrane thinner. The device were precured for 7 hour at room temperature, then move to 60° C. oven and cured overnight. After cure, the device were peeled off the mold and silanized with tridecafluoro-1,1,2,2-tetrahydrooctyl-1-trichlorosilane. Access holes were drilled with a 0.76 mm diameter diamond drill bit.

8. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

The present application incorporates the following applications by reference in their entireties for any and all purposes: U.S. Application 61/516,628, "Digital Isothermal Quantification of Nucleic Acids Via Simultaneous Chemical Initiation of Recombinase Polymerase Amplification (RPA) Reactions on Slip Chip," filed on Apr. 5, 2011; U.S. Application 61/518,601, "Quantification of Nucleic Acids With Large Dynamic Range Using Multivolume Digital Reverse Transcription PCR (RT-PCR) On A Rotational Slip Chip Tested With Viral Load," filed on May 9, 2011; U.S. application Ser. No. 13/257,811, "Slip Chip Device and Methods," filed on Sep. 20, 2011; International application PCT/US2010/028316, "Slip Chip Device and Methods," filed on Mar. 23, 2010; U.S. Application 61/262,375, "Slip Chip Device and Methods," filed on Nov. 18, 2009; U.S. Application 61/162,922, "Sip Chip Device and Methods," filed on Mar. 24, 2009; U.S. Application 61/340,872, "Slip Chip Device and Methods," filed on Mar. 22, 2010; U.S. application Ser. No. 13/440,371, "Analysis Devices, Kits, And Related Methods For Digital Quantification Of Nucleic Acids And Other Analytes," filed on Apr. 5, 2012; U.S. application Ser. No. 13/467,482, "Multivolume Devices, Kits, and Related Methods for Quantification and Detection of Nucleic Acids and Other Analytes," filed on May 9, 2012; U.S. application Ser. No. 14/433,602, "Methods and Systems for Microfluidics Imaging and Analysis," filed on Oct. 4, 2013; Selck et al., "Increased Robustness of Single-Molecule Counting with Microfluidics, Digital Isothermal Amplification, and a Mobile Phone versus Real-Time Kinetic Measurements, Analytical Chemistry, 85: 11129-36 (2013); and Rodriquez-Manzano et al. "Reading Out Single-Molecule Digital RNA and DNA Isothermal Amplification in Nanoliter Volumes with Unmodified Camera Phones, ACS Nano, 10(3): 3102-13 (2016).

9. EQUIVALENTS

While various specific embodiments have been illustrated and described, the above specification is not restrictive. It will be appreciated that various changes can be made without departing from the spirit and scope of the invention(s). Many variations will become apparent to those skilled in the art upon review of this specification.

10. SEQUENCE LISTING

| Description | 5'-3' sequence | SEQ ID NO: |
|---|---|---|
| F3 primer for detection of Hepatitis C RNA | cctcccggga gagccatag | SEQ ID NO: 1 |
| FIP primer for detection of Hepatitis C RNA | tccaagaaag gacccigtct ttttctgcgg aaccggtgag tac | SEQ ID NO: 2 |
| LF primer for detection of Hepatitis C RNA | tticcggiaa ttccggt | SEQ ID NO: 3 |
| B3 primer for detection of Hepatitis C RNA | gcactcgcaa gcaccitatc | SEQ ID NO: 4 |
| BIP primer for detection of Hepatitis C RNA | ttgggcgtgc ccccgciaga tttttcagta ccacaaggcc ittcgciacc | SEQ ID NO: 5 |
| LB primer for detection of Hepatitis C RNA | ctgctagccg agtagigttg | SEQ ID NO: 6 |
| F3 primer for detection of phage lambda DNA | gaatgcccgt tctgcgag | SEQ ID NO: 7 |
| FIP primer for detection of phage lambda DNA | cagcatccct ttcggcatac caggtggcaa gggtaatgag g | SEQ ID NO: 8 |
| LF primer for detection of phage lambda DNA | ggcggcagag tcataaagca | SEQ ID NO: 9 |
| B3 primer for detection of phage lambda DNA | ttcagttcct gtgcgtcg | SEQ ID NO: 10 |
| BIP primer for detection of phage lambda DNA | ggaggttgaa gaactgcggc agtcgatggc gttcgtactc | SEQ ID NO: 11 |
| LB primer for detection of phage lambda DNA | ggcagatctc cagccaggaa cta | SEQ ID NO: 12 | i = inosine

The invention claimed is:

1. A method of visually detecting a target nucleic acid in a sample, comprising the steps of:
dividing the sample into a plurality of compartments;
performing an amplification reaction on the divided sample to generate a reaction product;
exposing the reaction product to an amplification indicator, wherein the amplification indicator changes its extinction coefficient more than 3% responsive to nucleic acid amplification;
obtaining a color image of the reaction product in the plurality of compartments;
determining a plurality of first intensities for a first color of the color image, wherein the plurality of first intensities corresponds to the plurality of compartments;
determining a plurality of second intensities for a second color of the color image, wherein the plurality of second intensities corresponds to the plurality of compartments; and
determining a ratio between the first color intensity and the second color intensity for a compartment, wherein the ratio is indicative of the presence or absence of amplified target in the compartment.

2. The method of claim 1, further comprising the step of applying a threshold to the ratio to generate a binary readout of positive and negative reactions.

3. The method of claim 2, further comprising the step of determining a presence or an absence of the target nucleic acid within the compartment based on the binary readout.

4. The method of claim 2, further comprising the step of generating a binary image using the binary readout.

5. The method of claim 1, further comprising the step of identifying one or more pixels corresponding to each of the plurality of compartments in the color image, optionally wherein the first color intensity and the second color intensity are an average of color intensities corresponding to a plurality of pixels within one of the plurality of compartments.

6. The method of claim 5, wherein the step of determining the ratio between the first color intensity and the second color intensity is done for each of the plurality of compartments to generate a plurality of compartment color ratios, wherein each of the compartment color ratios correspond to each of the plurality of compartments.

7. The method of claim 1, further comprising the step of generating a binary readout of positive and negative reactions for each of the plurality of compartments to generate a plurality of compartment binary readouts, wherein each of the compartment binary readouts corresponds to each of the plurality of compartments.

8. The method of claim 7, further comprising a step of determining a concentration of the target nucleic acid within the sample based on a distribution of the compartment binary readouts.

9. The method of claim 7, wherein each of the plurality of compartments includes no or less than five molecules of the target nucleic acid.

10. The method of claim 1, wherein the step of obtaining the color image comprises obtaining an unprocessed color image and updating the unprocessed color image to generate the color image.

11. The method of claim 1, wherein the color image or the unprocessed color image is obtained with an unmodified camera, optionally wherein the unmodified camera is a cell phone camera.

12. The method of claim 1, wherein the step of determining the first color intensity and the second color intensity is done using a Red-Green-Blue (RGB) color scheme, a Cyan, Yellow, Magenta and Key (CYMK) color scheme, or a Lightness-A-B (L-A-B) color scheme.

13. The method of claim 1, wherein the step of obtaining the color image of the reaction product comprises detecting light absorbance, light reflection, or light transmission of the reaction product at a plurality of different wavelengths, optionally wherein the amplification indicator changes light absorbance, light reflection, or light transmission responsive to nucleic acid amplification.

14. The method of claim 1, wherein the amplification indicator changes its extinction coefficient more than 5%, more than 10%, more than 20%, more than 30%, or more than 40% responsive to nucleic acid amplification, optionally wherein the amplification indicator is a metal ion indicator, a pH indicator, a redox indicator or an oxidation-reduction indicator.

15. The method of claim 1, wherein the step of amplification reaction is done in a housing selected from the group consisting of a tube, a capillary tube, a droplet, a microfluidic device, a well, a well plate, a microplate, a microfluidic well, a microfluidic droplet, an emulsion, a solid support, a microchip, or a gel, optionally wherein the microfluidic device is a SlipChip device.

16. The method of claim 15, wherein the housing is a microfluidic device, wherein the microfluidic device comprises a plurality of compartments, each having a volume ranging from 500 nL to 1 µL, 250 nL to 500 nL, 125 nL to 250 nL, 25 nL to 125 nL, 5 nL to 25 nL, 1 nL to 5 nL, or 0.1 nL to 1 nL.

17. A non-transitory computer-readable medium comprising stored instructions, wherein the instructions when executed by a processor cause the processor to:

obtain a color image of the amplification reaction product wherein the amplification reaction product is generated by performing an amplification reaction on a sample and exposing a mixture for the amplification reaction to an amplification indicator, wherein the amplification indicator changes its extinction coefficient more than 3% responsive to nucleic acid amplification;
determine a first color intensity of the color image;
determine a second color intensity of the color image;
determine a ratio between the first color intensity and the second color intensity, wherein the ratio is indicative of the presence or absence of an amplified target in the amplification reaction product.

18. The computer-readable medium of claim 17, wherein the instructions further cause the processor to apply a threshold to the ratio to generate a binary readout of positive and negative reactions.

19. The computer-readable medium of claim 18, wherein the instructions further cause the processor to determine a presence or an absence of the target nucleic acid within the sample based on the binary readout.

20. The computer-readable medium of claim 17, wherein the color image comprises images of a plurality of compartments.

21. The computer-readable medium of claim 17, wherein the instructions further cause the processor to identify pixels corresponding to each image of the plurality of compartments in the color image.

22. The computer-readable medium of claim 20, wherein the instructions cause the processor to determine the first color intensity and the second color intensity for each of the plurality of compartments.

23. The computer-readable medium of claim 20, wherein the instructions cause the processor to determine the ratio between the first color intensity and the second color intensity for each of the plurality of compartments to generate a plurality of compartment color ratios, wherein each of the compartment color ratios corresponds to each of the plurality of compartments.

24. The computer-readable medium of claim 20, wherein the instructions cause the processor to generate a binary readout for each of the plurality of compartments to generate a plurality of compartment binary readouts, wherein each of the compartment binary readouts corresponds each of the plurality of compartments.

25. The computer-readable medium of claim 24, wherein the instructions further cause the processor to generate a binary image using the compartment binary readouts, optionally wherein the instructions further cause the processor to determine a presence or an absence of the target nucleic acid within the sample based on the binary image.

26. The computer-readable medium of claim 24, wherein the instructions further cause the processor to determine a concentration of the target nucleic acid within the sample based on the distribution of the compartment binary readouts.

27. The computer-readable medium of claim 17, wherein the instructions further cause the processor to generate a report related to a composition of the sample.

28. A system for visually detecting amplification of a target nucleic acid, comprising:
an amplification reactor comprising one or more compartments configured to perform an amplification reaction on a sample, wherein (i) the sample has a volume ranging from 1 pL to 1 µL, or (ii) each compartment has an optical path length less than 1 mm;
an unmodified camera configured to obtain a color image of a reaction product resulting from the amplification reaction;
a processor; and
a computer-readable medium of claim 17.

* * * * *

SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
cctcccggga gagccatag                                                19

<210> SEQ ID NO 2

```
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(16)
<223> OTHER INFORMATION: inosine

<400> SEQUENCE: 2
tccaagaaag gacccngtct ttttctgcgg aaccggtgag tac            43

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: inosine
<220> FEATURE:
<221> NAME/KEY: modified_base
<222> LOCATION: (8)..(8)
<223> OTHER INFORMATION: inosine

<400> SEQUENCE: 3
ttnccggnaa ttccggt                                          17

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(16)
<223> OTHER INFORMATION: inosine

<400> SEQUENCE: 4
gcactcgcaa gcaccntatc                                       20

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(17)
<223> OTHER INFORMATION: inosine
<220> FEATURE:
<221> NAME/KEY: modified_base
<222> LOCATION: (41)..(41)
<223> OTHER INFORMATION: inosine
<220> FEATURE:
<221> NAME/KEY: modified_base
<222> LOCATION: (47)..(47)
<223> OTHER INFORMATION: inosine

<400> SEQUENCE: 5
ttgggcgtgc ccccgcnaga tttttcagta ccacaaggcc nttcgcnacc      50
```

```
<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(16)
<223> OTHER INFORMATION: inosine

<400> SEQUENCE: 6
ctgctagccg agtagngttg                                                   20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaatgcccgt tctgcgag                                                     18

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cagcatccct ttcggcatac caggtggcaa gggtaatgag g                           41

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggcggcagag tcataaagca                                                   20

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttcagttcct gtgcgtcg                                                     18

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
```

```
ggaggttgaa gaactgcggc agtcgatggc gttcgtactc                                40

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcagatctc cagccaggaa cta                                                  23
```